(12) United States Patent
Hansen et al.

(10) Patent No.: US 7,553,953 B2
(45) Date of Patent: *Jun. 30, 2009

(54) CHIMERIC, HUMAN AND HUMANIZED ANTI-CSAP MONOCLONAL ANTIBODIES

(75) Inventors: Hans J. Hansen, Picayune, MS (US); David M. Goldenberg, Mendham, NJ (US)

(73) Assignee: Immunomedics, Inc., Morris Plains, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 12/042,063

(22) Filed: Mar. 4, 2008

(65) Prior Publication Data

US 2008/0193451 A1    Aug. 14, 2008

Related U.S. Application Data

(60) Continuation of application No. 11/070,697, filed on Mar. 3, 2005, now Pat. No. 7,414,121, which is a division of application No. 10/116,116, filed on Apr. 5, 2002, now Pat. No. 7,387,772, which is a continuation-in-part of application No. 09/823,746, filed on Apr. 3, 2001, now Pat. No. 6,962,702, which is a continuation-in-part of application No. 09/337,756, filed on Jun. 22, 1999, now Pat. No. 7,074,405.

(60) Provisional application No. 60/090,142, filed on Jun. 22, 1998, provisional application No. 60/104,156, filed on Oct. 14, 1998.

(51) Int. Cl.
*A61K 39/395* (2006.01)
*C07H 21/04* (2006.01)

(52) U.S. Cl. ............... 536/23.53; 424/133.1; 424/136.1; 424/138.1; 424/156.1; 435/69.6; 435/69.7

(58) Field of Classification Search ........................ None
See application file for complete search history.

(56) References Cited

U.S. PATENT DOCUMENTS

| | | | |
|---|---|---|---|
| 4,331,647 A * | 5/1982 | Goldenberg | ............... 424/1.37 |
| 4,468,457 A | 8/1984 | Goldenberg et al. | |
| 4,735,210 A | 4/1988 | Goldenberg | |
| 4,737,453 A | 4/1988 | Primus | |
| 4,792,521 A | 12/1988 | Shochat | |
| 4,818,709 A | 4/1989 | Primus | |
| 4,863,713 A | 9/1989 | Goodwin et al. | |
| 4,971,792 A | 11/1990 | Stephewski et al. | |
| 5,078,998 A | 1/1992 | Bevan et al. | |
| 5,101,827 A | 4/1992 | Goldenberg | |
| 5,128,119 A | 7/1992 | Griffiths | |
| 5,183,756 A | 2/1993 | Schlom | |
| 5,225,541 A | 7/1993 | Hackett et al. | |
| 5,274,076 A | 12/1993 | Barbet et al. | |
| 5,328,679 A | 7/1994 | Hansen et al. | |
| 5,469,854 A | 11/1995 | Unger et al. | |
| 5,502,037 A | 3/1996 | Kondratyer | |
| 5,503,987 A | 4/1996 | Wagner | |
| 5,534,254 A | 7/1996 | Huston | |
| 5,535,254 A | 7/1996 | Huston et al. | |
| 5,591,828 A | 1/1997 | Bosslet et al. | |
| 5,683,694 A | 11/1997 | Bagshawe et al. | |
| 5,693,762 A | 12/1997 | Queen et al. | |
| 5,697,902 A | 12/1997 | Goldenberg | |
| 5,716,595 A | 2/1998 | Goldenberg | |
| 5,746,996 A | 5/1998 | Govindan et al. | |
| 5,753,206 A | 5/1998 | McBride et al. | |
| 5,772,981 A | 6/1998 | Govindan et al. | |
| 5,776,093 A | 7/1998 | Goldenberg | |
| 5,776,094 A | 7/1998 | Goldenberg | |
| 5,776,095 A | 7/1998 | Goldenberg | |
| 5,837,242 A | 11/1998 | Holliger et al. | |
| 5,837,243 A | 11/1998 | Deo et al. | |
| 5,851,527 A | 12/1998 | Hansen | |
| 5,959,083 A | 9/1999 | Bosslet et al. | |
| 6,010,680 A | 1/2000 | Govindan et al. | |
| 6,077,499 A * | 6/2000 | Griffiths et al. | ............. 424/1.49 |
| 6,096,289 A * | 8/2000 | Goldenberg | ................ 424/1.49 |
| 6,121,424 A | 9/2000 | Whitlow et al. | |
| 6,126,916 A | 10/2000 | McBride | |
| 6,187,284 B1 | 2/2001 | Griffiths | |
| 6,962,702 B2 | 11/2005 | Hansen | |
| 7,074,405 B1 | 7/2006 | Hansen | |
| 7,091,321 B2 | 8/2006 | Gillies et al. | |
| 7,387,772 B1 * | 6/2008 | Hansen et al. | ............. 424/1.49 |

(Continued)

FOREIGN PATENT DOCUMENTS

EP        0263046        4/1988

(Continued)

OTHER PUBLICATIONS

Krishnan et al, Suppl. to Cancer, vol. 80, 2667-2674, 1997.*

(Continued)

*Primary Examiner*—David A Saunders
(74) *Attorney, Agent, or Firm*—Richard A. Nakashima

(57) ABSTRACT

The present invention provides humanized, chimeric and human anti-CSAp antibodies and anti-CSAp antibody fusion proteins that are useful for the treatment and diagnosis of various cancers, including colon cancer.

23 Claims, 9 Drawing Sheets

U.S. PATENT DOCUMENTS

| | | | |
|---|---|---|---|
| 7,414,121 B2* | 8/2008 | Hansen et al. | 536/23.4 |
| 2002/0006379 A1 | 1/2002 | Hansen et al. | |

FOREIGN PATENT DOCUMENTS

| | | |
|---|---|---|
| EP | 0511011 A | 10/1992 |
| EP | 0517024 A2 | 12/1992 |
| EP | 0623675 | 11/1994 |
| IE | 921782 | 12/1992 |
| JP | 03173900 | 7/1991 |
| WO | 9604313 | 2/1996 |
| WO | 9741898 | 11/1997 |
| WO | 9808875 | 3/1998 |
| WO | 9966951 | 12/1999 |
| WO | 00/34317 | 6/2000 |

OTHER PUBLICATIONS

McGuinness et al. Phage diabody repertoires for selection of large numbers of bispecific antibody fragments, Nature Biotechnology. 14:1149-1154 (1996).

Olafsen et al., "1gM secretory tailpiece drives multimerisation of bivalent scFv fragments in eukaryotic cells," Immunotechnology, 4(2):141-153 (1998).

Kipriyanov et al. "Bispecific tandem diabody for tumor therapy with improved antigen binding and pharmacokinetics," J. Mol. Biol., 293(1):41-56 (1999).

Karacay et al., "Studies on a humanized anti-CEA x murine anti-(In-DTPA) bispecific antibody construct for radioimmunotherapy of CEA-positive tumors," Proceedings of the American Association for Cancer Research Annual Meeting, vol. 40, p. 644, (Mar. 1999).

Karacay et al., "Pretargeting studies with a humanized anti-CEAX murine anti-(In- DTPA) bispecific antibody construct and Tc-99m/Re-188 labeled peptide," Journal of Nuclear Medicine, vol. 40, No. 5 Suppl.,p. 225 (May 1999).

Gautherot et al., "Delivery of therapeutic doses of radioiodine using bispecific antibody—targeted bivalent haptens," Journal of Nuclear Medicine, vol. 39 (11), pp. 1937-43 (Nov. 1998).

Bodere et al. "Phase I/II total of two-step radioimmunotherapy in medullary thyroid cancer (MTC) using bispecific anti-CEA/anti-DTPA—in antibody and iodine-131-labeled bivalent hapten," Journal of Nuclear Medicine, vol. 39, No. 5 Suppl, p. 246 (May 1998).

Bardies et al., "Bispecific antibody and iodine-131-labeled bivalent hapten dosimetry in patients with medullary thyroid or small-cell lung cancer," Journal of Nuclear Medicine, vol. 37, pp. 1853-1859 (Nov. 1996).

Hosono et al., "Biodistribution and dosimetric study in medullary thyroid cancer xenograft using bispecific antibody and iodine-125-labeled bivalent hapten." Journal of Nuclear Medicine, vol. 39 (9), pp. 1608-13 (Sep. 1998).

Kranenborg et al., "Development and characterization of and-renal cell carcinoma x antichelate bispecific monoclonal antibodies for two-phase targeting of renal cell carcinoma," Cancer Research, vol. 55(23 Suppl.), pp. 55643-5867S (Dec. 1, 1995).

Kranenborg et al. Two-step radio-immunotargeting of renal-cell carcinoma xenografts in nude mice with anti-renal-cell-carcinoma X anti-DTPA bispecific monoclonal antibodies, International Journal of Cancer, vol. 75 (1), pp. 74-80 (Jan. 5, 1998).

Gautherot "Therapy for colon carcinoma xenografts with bispecific antibody—targeted, iodine-131-labeled bivalent hapten," Cancer, vol. 80, No. Suppl. 12, pp. 2618-2623 (Dec. 15, 1997).

Bosslet et al., "Generation of bispecific monoclonal antibodies for two phase radioimmunotherapy," British Journal of Cancer, vol. 63/5, pp. 681-686 (1991).

Manetti et al., "Intracellular uptake and catabolism of anti-IgM antibodies and bi-specific antibody-targeted hapten by B-lymphoma cells," Int. J. Cancer, vol. 63(2), pp. 250-6 (1995).

Barbet et al., "Radioimmunotherapy of LS174T colon carcinoma in nude mice using an iodine-131-labeled bivalent hapten combined with an anti-CEAX anti-indium-DTPA bispecific antibody," Tumor Biology, vol. 18, No. Suppl. 2, p. 31 (Sep. 1997).

Goodwin et al. "Pre-Targeted Immunoscintigraphy of Murine Tumors with Indium-111-Labeled Bifunctional Haptens," J. Nucl., Med. vol. 29, pp. 226-234. 1998.

Stickney et al., "Bifunctional Antibody. A Binary Radiopharmaceutical Delivery System for Imaging Colorectal Carcinoma," Cancer Research, vol. 51, pp. 6650-6655, Dec. 15, 1991.

Gautherot et al. "Therapy for Colon Carcinoma Xenografts with Bispecific Antibody-Targeted, Iodine-131-Labeled Bivalent Hapten." Cancer Supplement, vol. 80, pp. 2616-2623, 1997.

Barbet et al., "Radioimmunodetection of Medullary Thyroid Carcinoma Using Indium-ill Bivalent Hapten and Anti-CEA X Anti-DTPA-Indium," The Journal of Nuclear Medicine, vol. 39, No. 7, Jul. 1998.

Schuhmacher et al., "Multistep Tumor Targeting in Nude ice Using Bispecific Antibodies and a Gallium Chelate Suitable for Immunoscintigraphy with Positron Emission Tomography," Cancer Research, vol. 55, pp. 115-123, Jan. 1, 1995.

Karacay, el al., "Experimental Pretargeting Studies of Cancer with a Humanized anti-CEA x Murine anti-(in-DTPA) Bispecific Antibody Construct and a 99mTc-/188 Re-Labeled Peptide" Bioconjugate Chem. 2000, 11, 842-854 pgs.

Karacay, H., et al. "Pretargeting Studies with a Murine Anti-Colon Specific Antigen-P (CSAp) X Chimeric Anti-[Indium-DPTA] Bispecific Antibody and Technetium-99m-Labeled Peptide," Cancer Biotherapy and Radiopharmaceuticals, vol. 15, No. 4, 2000, p. 412.

Communication from the European Patent Office, Jul. 10, 2006, supplementary partial European search report for EP 02725484 (6 pages).

Pluckthun et al., "New protein engineering approaches to Multivalent and bispecific antibody fragments," Immunotechnology 3 (1997) 83-105.

Pack et al., "Tetravalent Miniantibodies with High Avidity Assembling in Escherichia Coli." J. Mol. Biol. (1995) 246, 28-34.

Sharkey et al., "A Universal Pretargeting System for Cancer Detection and Therapy Using Bispecific Antibody." Cancer Research 63, 354-363 (Jan. 15, 2003).

Arano, Yasushi, et al., "Reassessment of Diethylenetriaminepentaacetic Acid (DTPA) as a Chelating Agent for Indium-111 Labeling of Polypeptides Using a Newly Synthesized Monoreactive DTPA Derivative," J Med. Chem, vol. 39, pp. 3451-3460, 1996.

Bamias, A., et al., "Two-Step Strategies for the Diagnosis and Treatment of Cancer with Bioconjugates." Antibody. Immunoconjugates, Radiopharm., vol. 5, No. 4, pp. 385-395, 1992.

BOS. EBO S., et al., "In Vitro Evaluation of DNA-DNA Hybridization as a Two-Step Approach in Radioimmunotherapy of Cancer," Cancer Research, vol. 54, pp. 3479-3486, 1994.

Greenwood, F. C., et al., "The Preparation of 131I-Labelled Human Growth Hormone of High Specific Radioactivity," The Biochemical Journal, vol. 89, pp. 114-123; 1963.

Kaneko. T., "New Hydrazone Derivative of Adriamycin and Their Immunoconjugates-a Correlation between Acid Stability and Cytotoxlcity," Bloconjugate Chem., vol. 2, No. 3, pp. 133-141, 1991.

Losman, M. J., et al., "Generation and Monitoring of Cell Lines Producing Humanized Antibodies." Clin. Cancer Research, vol. 5, (10 Suppl ) pp. 3101s-3105s, 1999.

Penefsky, Harvey S., "A Centrifuged-Column Procedure for the Measurement of Ligand Binding by Beef Heart F.," Methods in Enzymology, Part G, vol. 56, pp. 527-530, 1979.

Wang, Shing-Ming, et al., "Specific Activation of Glucuronide Prodrugs by Antibody-targeted Enzyme Conjugates for Cancer Therapy," Cancer Res., vol. 52, pp. 4484-4491, 1992.

De Jonge, Jan, et al., "Production and Characterization of Bispecific Single-Chain Antibody Fragments," Molecular Immunology, vol. 32, No. 17/18, pp. 1405-1412, 1995.

Boden, V., et al., "Preliminary Study of the Metal Binding Site of an Anti-DTPA Indium Antibody by Equilibrium Binding Immunoassays and Immobilzed Metal Ion Affinity Chromatography," Bioconjugate Chem. vol. 6, pp. 373-379, 1995.

Gold et al., Cancer Research, 50 6405-6409, 1990.

Van Spriel, et al., "Immunotherapeutic Perspective for Bispecific Antibodies" Immunology Today, 21, 391-396, 2000.

Kontermann, Roland E., "Intracellular and Cell Surface Displayed Single-chain Diabodies" Journal of Immunological Methods 226 (1999) 179-188.

Dubel, S., "Reconstitution of human pancreatic RNase from two separate fragments fused to different single chain antibody fragments: on the way to binary immunotoxins" Tumor Targeting (1999) 4, 37-46.

Hayden, M., "Single-chain mono- and bispecific antibody derivatives with novel biological properties and antitumour activity from a COS cell transient expression sytem" Therapeutic Immunology, 1994, 1, 3-15.

Yang "A Genetically Engineered Single-Chain FV/TNF Molecule Possesses the Anti-Tumor Immunoreactivity of FV as well as the Cytotoxic Activity of Tumor Necrosis Factor" Molecular Immunology vol. 32, No. 12, pp. 873-881, 1995.

Alt et al. "Novel Tetravalent and Bispecific lgG-like Antibody Molecules Combining Single-Chain Diabodies with the Immunoglobulin Gamma1 Fc or CH3 Region" FEBS Lett. Jul. 2, 1999; 454(1-2):90-4.

Kraeber-Bodere et al. "Bispecific Antibody and Bivalent Hapten Radioimmunotherapy in CEA-Producing Medullary Thyroid Cancer Xenograft" J. Nucl. Med. 1999; 40:198-204.

Hawkins et al. "Delivery of Radionuclides to Pretargeted Monoclonal Antibodies Using Dihydrofolate Reductase and Methotrexate in an Affinity System" Cancer Res. 53(10):2368-73 (1993).

Chatziioannou et al. "MicroPET I: Performance Evaluation of a Very High Resolution PET Scanner for Imaging Small Animals" J. Nucl. Med. 1997; 38(5):7P-8P.

Sharkey et al. "Development of a Streptavidin-Anti-Carcinoembryonic Antigen Antibody, Radiolabeled Biotin Pretargeting Method for Radioimmunotherapy of Colorectal Cancer. Studies in a Human Colon Cancer Xenograft Model" Bioconjugate Chem. 1997, 8(4):595-604.

Hillairet De Boisferon et al. "Enhanced Targeting Specificity to Tumor Cells by Simultaneous Recognition of Two Antigens" Bioconjugate Chem. 2000, 11:452-460.

Barbet et al. "Radioimmunotherapy of LS174T Colon Carcinoma in Nude Mice Using an Iodine-131-Labeled Bivalent Hapten Combined with an Anti-CEA x Anti-Indium-DTPA Bispecific Antibody" Tumor Biol., vol. 18, No. Suppl. 2, p. 31 (Sep. 1997).

* cited by examiner

Mu9VH

```
AGGTGCAGCTGCAGGAGTCAGGACCTGAGCTGGTGAAGCCTGGGGCTTCAGTGAAGATGTCCTGCAGGGCTTCTGGATACACCTTCACT      89
        2                               10                              20                              30
        V  Q  L  Q  E  S  G  P  E  L  V  K  P  G  A  S  V  K  M  S  C  R  A  S  G  Y  T  F  T

GAGTATGTTATTACCTGGGTAAAACAGAGGACAGGGCCTTGAGTGGATTGGAGAGATTATCCTGGAAGTGGTAGTACTTCCTAC             179
                          40                              50    52 A
        E  Y  V  I  T  W  V  K  Q  R  T  G  Q  G  L  E  W  I  G  E  I  Y  P  G  S  G  S  T  S  Y
        CDR1                                                    CDR2

AATGAAAAGTTCAAGGGCAAGGCCACACTGACTGCAGACAAATCCTCCAACACAGCCTACATGCACCTCAGCAGCCTGACATCTGAGGAC       269
        60                              70                              80    82 A  B  C
        N  E  K  F  K  G  K  A  T  L  T  A  D  K  S  S  N  T  A  Y  M  H  L  S  S  L  T  S  E  D

TCTGCGGTCTATTTCTGTACAAGAGAGGATCTTGGGGGCCAAGGGACTCTGGTCACTGTCTCTTCA                              335
        90                  97 103                      110     113
        S  A  V  Y  F  C  T  R  E  D  L  G  G  Q  G  T  L  V  T  V  S  S
                                CDR3
```

```
GCTGTTTTGATGACCCAAACTCCACTCTCCCTGCCTGTCAGTCTTGGAGATCAAGCCTCCATCTCTTGCAGAGCATTGTC    90
  1               10                  20                  27 A B C
  A  V  L  M  T  Q  T  P  L  S  L  P  V  S  L  G  D  Q  A  S  I  S  C  R  S  S  Q  S  I  V
                                                                        CDR1

CATAGTAATGGCAACACCTATTTAGAATGGTACCTGCAGAAACCAGGCCAGTCTCCAAAGCTCCTGATCTACAAAGTTTCCAACCGATTT  180
              30                  40                  50
  D  E  H  S  N  G  N  T  Y  L  E  W  Y  L  Q  K  P  G  Q  S  P  K  L  L  I  Y  K  V  S  N  R  F
         CDR1                                                              CDR2

TCTGGGGTCCCAGACAGGTTCAGTGGCACTGGATCAGGGACAGATTTCACAGTCAGGATCAGCAGAGTGAGGCTGAGGATCTGGGACTT    270
              60                  70                  80
  S  G  V  P  D  R  F  S  G  T  G  S  G  T  D  F  T  V  R  I  S  R  V  E  A  E  D  L  G  L

TATTACTGCTTTCAAGGTTCACGTGTTCCGTACACGTTCGGAGGGGGGACCAAGCTGGAAATAAAA                          336
              90                 100           107
  Y  Y  C  F  Q  G  S  R  V  P  Y  T  F  G  G  G  T  K  L  E  I  K
           CDR3
```

Figure 1B.

cMu9VH

```
        PstI
CAGGTCCAACTGCAGGAGTCAGGACCTGAGCTGGTGAAGCCTGGGGCTTCAGTGAAGATGTCCTGCAGGGCTTCTGATACACCTTCACT    90
  1                  10                  20                  30
  Q   V   Q   L   Q   E   S   G   P   E   L   V   K   P   G   A   S   V   K   M   S   C   R   A   S   G   Y   T   F   T

GAGTATGTTATTACCTGGGTAAAACAGAGGACAGGGCCTTGAGTGAGTTGGAGAGATTTATCCTGGATGTGGAAGTGGTAGTACTTCCTAC   180
                  40                  50    52 A            CDR2
  E   Y   V   I   T   W   V   K   Q   R   T   G   Q   G   L   E   W   I   G   E   I   Y   P   G   S   S   T   S   Y
  ─────CDR1─────

AATGAAAAAGTTCAAGGGCAAGGCCACACTGACTGCAGACAAATCCTCCAACACAGCCTACATGCACCTCAGCAGCCTGACATCTGAGGAC   270
 60                  70                  80    82 A B C
  N   E   K   F   K   G   K   A   T   L   T   A   D   K   S   S   N   T   A   Y   M   H   L   S   S   L   T   S   E   D

BstEII
TCTGCGGGTCTATTTCTGTACAAGAGAGGATCTTGGGGGCCAAGGGACTCTGGTCACCGTCTCCTCA                          336
                  90    97  103                    110       113
  S   A   V   Y   F   C   T   R   E   D   L   G   G   Q   G   T   L   V   T   V   S   S
                          ───CDR3───
```

Figure 2A.

cMu9Vk

```
         PvuII
     GACATCCTGCAGACCCAGACTCCACTCTCCCTGCCTGTCAGTCTTGGAGATCTTCCATCTCTTGCAGAGATCTAGTCAGAGCATTGTC          90
      1                              10                              20                   27 A B C
      D  I  L  Q  T  Q  T  P  L  S  L  P  V  S  L  G  D  Q  A  S  I  S  C  R  S  S  Q  S  I  V
                                                                                 CDR1

CATAGTAATGGCAACACCTATTTAGAATGGTACCTGCAGAAACCAGGCCAGTCCTCCAAAGCTCCTGATCTACAAAGTTTCCAACCGATTT        180
      D  E     30                          40                              50
      D  E  H  S  N  G  N  T  Y  L  E  W  Y  L  Q  K  P  G  Q  S  P  K  L  L  I  Y  K  V  S  N  R  F
            CDR1                                                                CDR2

TCTGGGGTCCCAGACAGGTTCAGTGGCAGTGGATCAGGGACAGATTTCACAGTCAGGATCAGCAGAGTGGAGGCTGAGGATCTGGGACTT       270
                      60                              70                              80
      S  G  V  P  D  R  F  S  G  S  G  S  G  T  D  F  T  V  R  I  S  R  V  E  A  E  D  L  G  L

BglII/BclI
     TATTACTGCTTTCAAGGTTCACGTGTTCCGTACACGTTCGGAGGGGGACCAAGCTGGAGATCAAACGT                              339
                      90                              100             108
      Y  Y  C  F  Q  G  S  R  V  P  Y  T  F  G  G  G  T  K  L  E  I  K  R
                  CDR3
```

Figure 2B.

```
                  1                  10        20        30        40
EUVH              PVQLVQSGAEVKKPGSSVKVSCKASGGTFSRSAIIWVRQA
Mu9VH             -VQLQE··P···A···M··R···Y··TEYV·T···K·R
hMu9VH            QVQLQ···················Y··TEYV·T···K·R 50 52 A                  60        70
EUVH              PGQGLEWMGGIVPMFGPPNYAQKFQGRVTITADESTNTAY
Mu9VH             T····I·E·Y·GS·STS·NE··K·KA·L···K·S······
hMu9VH            ··········I·E·Y·GS·STS·NE··K·KA········

80 82 A B C              90       100       110
EUVH              MELSSLRSEDTAFYFCAGGYGIYSPEEYNGGLVTVS
Mu9VH             ·H·····T····S·V···TREDL-----
hMu9VH            ·············TREDL-----

103        110  113
NEWMVH            WGQGSLVTVSS
Mu9VH             G···T··TVSS
hMu9VH            G·····TVSS
```

Figure 3A.

```
             1                    10                  20            27 A B C D E         30
WOLVk        E I V L T Q S P G T L S L S P G E R A T L S C R A S Q S - - - - V S S G Y L G W
Mu9Vk        A V L M · · T · L S · P V · L · D Q · S I · · · S · · · I V H S N G N T · · E ·
hMu9Vk       D I Q L · · · · · · · · · · · · · · · · · · · · · · · S · · · I V H S N G N T · · E ·

40                 50                 60                 70
WOLVk        Y Q Q K P G Q A P R L L I Y G A S S R A T G I P D R F S G S G S G T D F T L T I
Mu9Vk        · L · · · · · · · · · · · · · · · S · K · · · K V · N · F S · V · · · · · T · · · · · V R ·
hMu9Vk       · L · · · · · · · · · · · · · · · · · · · · · K V · N · F S · V · · · · · · · · · · · · · · ·

80                 90                100         108
WOLVk        S R L E P E D F A V Y Y C Q Q Y G S L G R T F G Q G T K V E I K R
Mu9Vk        · · V · A · L G L · · · · F · G S R V P Y · · · G · · · L E I K -
hMu9Vk       · · · · · · · · · · · · · · · F · G S R V P Y · · · G · · · · E I K R
```

Figure 3B.

hMu9VH

```
              PstI
CAGGTCCAACTGCAGCAGTCAGGAGCTGAGGTGAAAAAGCCTGGGAGCTCAGTGAAGGTCTCCTGCAAGGCTTCTGGATACACCTTCACT
  1                              10                          20                          30
  Q  V  Q  L  Q  Q  S  G  A  E  V  K  K  P  G  S  S  V  K  V  S  C  K  A  S  G  Y  T  F  T

GAGTATGTTATTACCTGGGTAAAACAGAGACCTGGATAAAACAGAGACCTGGACAGGGTCTAGAGTGGATTGGAGAGATTTATCCTGGAAGTGGTAGTACTTCCTAC
                         40                     50      52 A                            Y
  E  Y  V  I  T  W  V  K  Q  R  P  G  Q  G  L  E  W  I  G  E  I  Y  P  G  S  G  S  T  S  Y
  ───CDR1───                                              ─────────────CDR2

AATGAAAAGTTCAAGGGCAAGGCCACAATCACTGCTGACAAATCCACTAACACAGCCTACATGGAGCTCAGCAGCCTGAGATCTGAGGAC
  60                          70                      80      82 A B C
  N  E  K  F  K  G  K  A  T  I  T  A  D  K  S  T  N  T  A  Y  M  E  L  S  S  L  R  S  E  D
  ─────────                                                       BstEII

ACTGCGTTCTATTTCTGTACAAGAGAGGATCTTGGGGGCCAAGGGGTCTCTGGTCACCGTCTCCTCA
               90          97 103                    110           113
  T  A  F  Y  F  C  T  R  E  D  L  G  G  Q  G  S  L  V  T  V  S  S
                          ─────CDR3
```

hMu9Vk

```
          PvuII
GACATCCAGCTGACCCAGTCCCCAAGCCACCCTGTCCCTCAGTCCTGGAGAGGCGAGCCACTCTGTCTTGCAGGTCTAGTCAGAGCATTGTG    90
         1               10              20          27 A B C
         D  I  Q  L  T  Q  S  P  G  T  L  S  L  S  P  G  E  R  A  T  L  S  C  R  S  S  Q  S  I  V
CATAGTAATGGCAACACCTATTTAGAATGGTACCTGCAGAAACCAGGCCAGGCTCCAAGGCTCCTGATCTACAAAGTTTCCAACCGATTT    180
     30                              40                  50
   H  S  N  G  N  T  Y  L  E  W  Y  L  Q  K  P  G  Q  A  P  R  L  L  I  Y  K  V  S  N  R  F
   CDR1                                                                  CDR2
TCCGGAGTCCCAGACAGGTTCAGTGGCTCTGGATCAGGGACAGATTTCACACTTACTATCAGCAGACTGGAGCCTGAGGATTTTGCTGTG    270
          60                      70                   80
   S  G  V  P  D  R  F  S  G  S  G  S  G  T  D  F  T  L  T  I  S  R  L  E  P  E  D  F  A  V
                                               BglII/BclI
TATTACTGCTTTCAAGGTTCACGTGTTCCGTACACGTTCGGAGGGGGGACCAAGGTGGAGATCAAAACGT                        336
            90                      100          108
   Y  Y  C  F  Q  G  S  R  V  P  Y  T  F  G  G  G  T  K  V  E  I  K  R
            CDR3
```

CHIMERIC, HUMAN AND HUMANIZED ANTI-CSAP MONOCLONAL ANTIBODIES

This application is a continuation of U.S. patent application Ser. No. 11/070,697, filed Mar. 3, 2005, (now issued U.S. Pat. No. 7,414,121), which is a divisional of U.S. patent application Ser. No. 10/116,116, filed Apr. 5, 2002, (now issued U.S. Pat. No. 7,387,772), which is a continuation-in-part of U.S. patent application Ser. No. 09/823,746, filed Apr. 3, 2001, (now issued U.S. Pat. No. 6,962,702), which is a continuation-in-part of U.S. patent application Ser. No. 09/337,756, filed Jun. 22, 1999, (now issued U.S. Pat. No. 7,074,405), which claims the benefit under 35 U.S.C. 119(e) of U.S. Provisional Patent Application Ser. Nos. 60/104,156, filed Oct. 14, 1998, (now expired) and 60/090,142, filed Jun. 22, 1998, (now expired) the contents of each of which are incorporated herein by reference in their entirety.

BACKGROUND OF THE INVENTION

1. Field of the Invention

The invention relates to immunological reagents for therapeutic use, for example, in radioimmunotherapy (RAIT) and chemoimmunotherapy, and detection and/or diagnostic uses, for example, in radioimmunodetection (RAID), ultrasonography, and magnetic resonance imaging (MRI). In particular, the invention relates to naked antibodies (unconjugated) and directly-conjugated antibodies, as well as bi-specific antibodies (bsAbs) and bi-specific antibody fragments (bsFabs) which have at least one arm which is reactive against a targeted tissue and at least one other arm which is reactive against a linker moiety. Further, the invention relates to monoclonal antibodies that have been raised against specific immunogens, being human, humanized and chimeric monoclonal antibodies, as well as human, humanized and chimeric bi-specific antibodies and antibody fragments having at least one arm which is reactive against a targeted tissue and at least one other arm which is reactive against a linker moiety, DNAs that encode such antibodies and antibody fragments, and vectors for expressing the DNAs.

The present invention also relates to humanized, chimeric and human anti-CSAp antibodies, particularly monoclonal antibodies (mAbs), therapeutic and detection/diagnostic conjugates of humanized, chimeric and human anti-CSAp antibodies and methods of diagnosing/detecting or treating a malignancy using humanized, chimeric and human anti-CSAp antibodies. The present invention also relates to antibody fusion proteins or fragments thereof comprising at least two anti-CSAp mAbs or fragments thereof or at least one anti-CSAp mAb or fragment thereof and at least one second mAb or fragment thereof, other than the anti-CSAp mAb or fragment thereof. The humanized, chimeric and human anti-CSAp mAbs, fragments thereof, antibody fusion proteins thereof, or fragments thereof may be administered alone, as a therapeutic conjugate or in combination with a therapeutic immunoconjugate, with other naked antibodies, or with other therapeutic agents or as a diagnostic/detection conjugate. The present invention also provides DNA sequences encoding humanized, chimeric and human anti-CSAp antibodies, and antibody fusion proteins, vectors and host cells containing the DNA sequences, and methods of making the humanized, chimeric and human anti-CSAp antibodies.

2. Related Art

An approach to cancer therapy and detection/diagnosis involves directing antibodies or antibody fragments to disease tissues, wherein the antibody or antibody fragment can target a detection/diagnostic agent or therapeutic agent to the disease site. One approach to this methodology that has been under investigation involves the use of bi-specific monoclonal antibodies (bsAbs) having at least one arm that is reactive against a targeted diseased tissue and at least one other arm that is reactive against a low molecular weight hapten. In this methodology, a bsAb is administered and allowed to localize to target, and to clear normal tissue. Some time later, a radiolabeled low molecular weight hapten is given, which being recognized by the second specificity of the bsAb, also localizes to the original target. The same technology can be used to target therapeutic isotopes, drugs and toxins selectively to diseased tissues, particularly cancers against which the bsAb is targeted, or non-radioactive diagnostic agents for improved diagnosis and detection of pathological lesions expressing the target antigen.

Although low MW haptens used in combination with bsAbs possess a large number of specific imaging and therapy uses, it is impractical to prepare individual bsAbs for each possible application. Further, the application of a bsAb/low MW hapten system has to contend with several other issues. First, the arm of the bsAb that binds to the low MW hapten must bind with high affinity, since a low MW hapten is designed to clear the living system rapidly, when not bound by bsAb. Second, the non-bsAb-bound low MW hapten actually needs to clear the living system rapidly to avoid non-target tissue uptake and retention. Third, the detection and/or therapy agent must remain associated with the low MW hapten throughout its application within the bsAb protocol employed.

Of interest with this approach are bsAbs that direct chelators and metal chelate complexes to cancers using Abs of appropriate dual specificity. The chelators and metal chelate complexes used are often radioactive, using radionuclides such as cobalt-57 (Goodwin et al., U.S. Pat. No. 4,863,713), indium-111 (Barbet et al., U.S. Pat. No. 5,256,395 and U.S. Pat. No. 5,274,076, Goodwin et al., *J. Nucl. Med.* 33:1366-1372 (1992), and Kranenborg et al. *Cancer Res (suppl.)* 55:5864s-5867s (1995) and *Cancer (suppl.)* 80:2390-2397 (1997)) and gallium-68 (Boden et al., *Bioconjugate Chem.* 6:373-379, (1995) and Schuhmacher et al. *Cancer Res.* 55:115-123 (1995)) for radioimmuno-imaging. Because the Abs were raised against the chelators and metal chelate complexes, they have remarkable specificity for the complex against which they were originally raised. Indeed, the bsAbs of Boden et al. have specificity for single enantiomers of enantiomeric mixtures of chelators and metal-chelate complexes. This great specificity has proven to be a disadvantage in one respect, in that other nuclides such as yttrium-90 and bismuth-213, useful for radioimmunotherapy (RAIT), and gadolinium, useful for MRI, cannot be readily substituted into available reagents for alternative uses. As a result, iodine-131, a non-metal, has been adopted for RAIT purposes by using an I-131-labeled indium-metal-chelate complex in the second targeting step. A second disadvantage to this methodology requires that antibodies be raised against every agent desired for diagnostic or therapeutic use.

Thus, there is a continuing need for an immunological agent which can be directed to diseased tissue and is reactive with a subsequently administered linker moiety which is bonded to or associated with a therapeutic or diagnostic/detection metal chelate complex or a therapeutic or diagnostic/detection chelator.

The present invention relates to recombinantly produced chimeric, humanized and human monoclonal antibodies directed against cancers, including colorectal, pancreatic, and ovarian cancers. Chimeric, humanized and human monoclonal antibodies cause less production of human anti-mouse antibodies than completely murine antibodies. Additionally, when the antibodies are covalently conjugated to a diagnostic or therapeutic reagent, they retain their binding characteristics. Further, if the human, humanized or chimeric antibodies have human constant regions that can be immunologically functional in patients, such as is the case for IgG$_1$, then these can also be active against such tumors as naked, or unconjugated, antibodies, and as such may also potentiate the antitumor effects of other therapeutic modalities, such as chemotherapy and radiation.

Colorectal, pancreatic, and ovarian cancers remain important contributors to cancer mortality. Their response to traditional chemotherapy and radiation therapy is mixed, however. Furthermore, these conventional forms of therapy have toxic side effects that limit their utility.

The use of monoclonal antibodies offers an alternative to traditional chemotherapy and radiation therapy. Tumor-specific and tumor-associated monoclonal antibodies can function alone (naked antibody therapy) or as conjugates in treatment regimens. The use of targeting monoclonal antibodies conjugated to radionuclides or other cytotoxic agents offers the possibility of delivering such agents directly to the tumor site, thereby limiting the exposure of normal tissues to toxic agents (Goldenberg, Semin. Nucl. Med., 19: 332 (1989); Goldenberg, D M, Radioimmunotherapy, in: Nuclear Medicine Annual 2001, L. Freeman, ed., Lippincott, William & Wilkins, Philadelphia, 2001, pp. 167-206). In recent years, the potential of antibody-based therapy and its accuracy in the localization of tumor-associated antigens have been demonstrated both in the laboratory and clinical studies (see, e.g., Thorpe, TIBTECH, 11: 42 (1993); Goldenberg, Scientific American, Science & Medicine, 1: 64 (1994); Baldwin et al., U.S. Pat. Nos. 4,923,922 and 4,916,213; Young, U.S. Pat. No. 4,918,163; U.S. Pat. No. 5,204,095; Irie et al., U.S. Pat. No. 5,196,337; Hellstrom et al., U.S. Pat. Nos. 5,134,075 and 5,171,665, Thorpe et al., U.S. Pat. No. 6,342,221, and Epstein et al., U.S. Pat. Nos. 5,965,132, 6,004,554, 6,071,491, 6,017,514, 5,882,626 and 5,019,368. In general, the use of radiolabeled antibodies or antibody fragments against tumor-associated markers for localization of tumors has been more successful than for therapy, in part because antibody uptake by the tumor is generally low, ranging from only 0.01% to 0.001% of the total dose injected (Vaughan et al., Brit. J. Radiol., 60: 567 (1987)). Increasing the concentration of the radiolabel to increase the dosage to the tumor is generally counterproductive, as this also increases exposure of healthy tissue to radioactivity.

Mu-9 is a murine monoclonal antibody of the IgG$_1$ subtype, directed against the colon-specific antigen-p mucin (CSAp). CSAp is a tumor-associated antigen that is present in a high percentage of colorectal, as well as pancreatic and ovarian cancers. (Gold et al., Cancer Res., 50: 6405 (1990), and references cited therein). In pre-clinical and clinical testing, the antibody has shown excellent tumor targeting ability (Blumenthal et al., Int. J. Cancer, 22: 292 (1989); Sharkey et al., Cancer, 73(suppl): 864 (1994)). Mu-9 has an advantage over other antibodies that target tumor antigens because it recognizes an epitope, which is not present in the circulation (Pant et al., Cancer, 50: 919 (1982)). Circulating antigen can alter the delivery of antibody therapy because the antibody forms circulating immune complexes, which in turn could affect tumor targeting and antibody pharmacokinetics and biodistribution.

As with most other promising non-human antibodies, the clinical use of murine Mu-9 may be limited by the development in humans of anti-mouse antibody (HAMA) responses. This can limit the diagnostic/detection and therapeutic usefulness of the antibodies, not only because of the potential anaphylactic problem, but also because a major portion of the circulating antibody may be complexed to and sequestered by the circulating anti-mouse antibodies. The production of HAMA may also affect the accuracy of murine antibody-based immunoassays. Thus, HAMA responses in general pose a potential obstacle to realizing the full diagnostic and therapeutic potential of the Mu-9 antibody.

In order to maximize the value of the Mu-9 antibody as a therapeutic or diagnostic/detection modality and to increase its utility in multiple and continuous administration modalities and settings, an object of this invention is to provide a mouse-human chimeric mAb (cMu-9), a fully human, and a humanized mAb (hMu-9) that relate to Mu-9 by retaining the antigen-binding specificity of Mu-9, but that elicit reduced HAMA or other immune responses in a subject receiving the same.

Another object of this invention is to provide DNA sequences that encode the amino acid sequences of the variable regions of the light and heavy chains of the cMu-9, human Mu-9, and hMu-9 mAbs, including the complementarity-determining regions (CDRs).

A further object of this invention is to provide conjugates of the hMu-9, human Mu-9, and cMu-9 mAbs containing therapeutic or diagnostic/detection modalities.

Another object of this invention is to provide combinations of antibodies with CSAp antibody or antibodies with other carcinoma-targeting antibodies, wherein said antibodies can be used as naked immunoglobulins or as conjugates with drugs, toxins, isotopes, cytokines, enzymes, enzyme-inhibitors, hormones, hormone antagonists, and other therapy-enhancing moieties.

Yet another object of this invention is to provide methods of therapy and diagnosis/detection that utilize the humanized, chimeric and fully human MAbs of the invention.

SUMMARY OF THE INVENTION

The present invention provides a monoclonal (MAb) antibody or fragment thereof that binds to a colon-specific antigen-p mucin (CSAp) antigen. Preferably, the monoclonal antibody or fragment thereof binds the Mu-9 epitope. Still preferred, the monoclonal antibody or fragment thereof is humanized, chimerized or fully human.

The invention also provides a humanized Mu-9 (hMu-9) monoclonal antibody (mAb) or a fragment thereof. The hMu-9 antibody or fragment contains the complementarity-determining regions (CDRs) of the light and heavy chain variable regions of a non-human Mu-9 antibody, which are joined to the framework (FR) regions of the light and heavy chain variable regions of a human antibody, which are subsequently joined to the light and heavy chain constant regions of a human antibody. This humanized antibody or fragment retains the CSAp antigen specificity of the parental Mu-9 antibody, but is less immunogenic in a human subject.

In another aspect, the invention provides a chimeric Mu-9 (cMu-9) monoclonal antibody or fragment thereof. The cMu-9 antibody or fragment contains the light and heavy chain variable regions of a non-human Mu-9 antibody, which are joined to the light and heavy chain constant regions of a human antibody. This chimeric antibody retains the CSAp antigen specificity of the parental Mu-9 antibody, but is less immunogenic in a human subject.

Also contemplated in the present invention is a fully human Mu-9 antibody and fragments thereof.

Also contemplated in the present invention is a humanized antibody or fragment thereof comprising the complementarity-determining regions (CDRs) of a murine anti-CSAp MAb and the framework (FR) regions of the light and heavy chain variable regions of a human antibody and the light and heavy chain constant regions of a human antibody, wherein the CDRs of the light chain variable region of the humanized anti-CSAp MAb comprises CDR1 comprising an amino acid sequence of RSSQSIVHSNGNTYLE; CDR2 comprising an amino acid sequence of KVSNRFS and CDR3 comprising an amino acid sequence of FQGSRVPYT; and the CDRs of the heavy chain variable region of the humanized anti-CSAp MAb comprises CDR1 comprising an amino acid sequence of EYVIT; CDR2 comprising an amino acid sequence of EIYPGSGSTSYNEKFK and CDR3 comprising an amino acid sequence of EDL.

The present invention further provides a CDR-grafted humanized heavy chain comprising the complementarity-determining regions (CDRs) of a murine anti-CSAp MAb and the framework region of the heavy chain variable region of a human antibody and the heavy chain constant region of a human antibody, wherein the CDRs of the heavy chain variable region of the humanized anti-CSAp MAb comprises CDR1 comprising an amino acid sequence of EYVIT; CDR2 comprising an amino acid sequence of EIYPGSGSTSYN-EKFK and CDR3 comprising an amino acid sequence of EDL.

In a related vein, the present invention provides a CDR-grafted humanized light chain comprising the complementarity determining regions (CDRs) of a murine anti-CSAp MAb and the framework region of the light chain variable region of a human antibody and the light chain constant region of a human antibody, wherein the CDRs of the light chain variable region of the humanized anti-CSAp MAb comprises CDR1 comprising an amino acid sequence of RSSQSIVHSNGN-TYLE; CDR2 comprising an amino acid sequence of KVS-NRF and CDR3 comprising an amino acid sequence of FQG-SRVPYT.

The invention further relates to a diagnostic/detection immunoconjugate comprising an antibody component comprising an anti-CSAp MAb or fragment thereof or an antibody fusion protein or fragment thereof of any one of anti-CSAp antibodies described herein, wherein the antibody component is bound to at least one diagnostic/detection agent. Preferably, the diagnostic/detection immunoconjugate comprises at least one photoactive diagnostic/detection agent. More preferably, the photoactive diagnostic/detection agent comprises a chromagen or dye. Still preferred, the diagnostic/detection agent is a radionuclide with an energy between 20 and 2,000 keV.

In a related vein, the invention further provides a therapeutic immunoconjugate comprising an antibody component comprising an anti-CSAp MAb or fragment thereof or an antibody fusion protein or fragment thereof of any one of anti-CSAp antibodies described herein, wherein the antibody component is bound to at least one therapeutic agent. In a preferred embodiment, the therapeutic agent is a radionuclide, boron, gadolinium or uranium atoms, an immunomodulator, a cytokine, a hormone, a hormone antagonist, an enzyme, an enzyme inhibitor, a photoactive therapeutic agent, a cytotoxic drug, a toxin, an angiogenesis inhibitor, a second, different antibody, and a combination thereof. When the therapeutic immunoconjugate is a radionuclide, the energy is preferably between 20 and 10,000 keV.

The invention further provides multivalent, multispecific antibody or fragment thereof comprising one or more antigen binding sites having affinity toward a CSAp target antigen and one or more hapten binding sites having affinity towards hapten molecules.

The invention also relates to an antibody fusion protein or fragment thereof comprising at least two anti-CSAp MAbs or fragments thereof, as described herein. Similarly, the invention contemplates an antibody fusion protein or fragment thereof that comprises at least one first anti-CSAp MAb or fragment thereof, as described herein, and at least one second MAb or fragment thereof, other than the anti-CSAp antibodies of the present invention.

The invention also provides a method of treating a malignancy in a subject, comprising the step of administering to said subject a therapeutically effective amount of an anti-CSAp antibody or fragment thereof, formulated in a pharmaceutically acceptable vehicle.

Similarly, the present invention provides for a method of treating or diagnosing/detecting a malignancy in a subject, comprising (i) administering to a subject in need thereof the antibody or fragments thereof of the present invention; (ii) waiting a sufficient amount of time for an amount of the non-binding protein to clear the subject's bloodstream; and (iii) administering to said subject a carrier molecule comprising a diagnostic agent, a therapeutic agent, or a combination thereof, that binds to a binding site of the antibody.

The invention also provides for a DNA sequence comprising a nucleic acid encoding a anti-CSAp MAb or fragment thereof selected from the group consisting of (a) an anti-CSAp MAb or fragment thereof as described herein;

(b) an antibody fusion protein or fragment thereof comprising at least two of the MAbs or fragments thereof;

(c) an antibody fusion protein or fragment thereof comprising at least one first anti-CSAp MAb or fragment thereof comprising said MAb or fragment thereof of any one of the anti-CSAp antibodies of the present invention and at least one second MAb or fragment thereof, other than the MAb or fragment thereof of the present invention; and (d) an antibody fusion protein or fragment thereof comprising at least one first MAb or fragment thereof comprising said MAb or fragment thereof of any one of the antibodies described herein and at least one second MAb or fragment thereof, other than the MAb or fragment thereof of any one of the antibodies described herein, wherein said second MAb is selected from the group consisting of CEA, EGP-1, EGP-2, MUC-1, MUC-2, MUC-3, MUC-4, PAM-4, KC4, TAG-72, EGFR, HER2/neu, BrE3, Le-Y, A3, KS-1, CD40, VEGF antibody, and the antibody A33, and a combination thereof.

The invention also relates to a method of delivering a diagnostic/detection agent, a therapeutic agent, or a combination thereof to a target, comprising: (i) administering to a subject the antibody or fragments thereof of any one the anti-CSAp antibodies of the present invention; (ii) waiting a sufficient amount of time for an amount of the non-binding protein to clear the subject's blood stream; and (iii) administering to said subject a carrier molecule comprising a diagnostic/detection agent, a therapeutic agent, or a combination thereof, that binds to a binding site of said antibody.

Described herein is also a method of treating a malignancy in a subject comprising administering to said subject a therapeutically effective amount of an antibody or fragment thereof or an antibody fusion protein or fragment thereof comprising at least two MAbs or fragments thereof, wherein at least one anti-CSAp MAb or fragment thereof or fusion proteins or fragments thereof as described herein, formulated in a pharmaceutically suitable excipient.

The present invention further relates to a method of treating a cancer in a subject comprising (i) administering to said subject a therapeutically effective amount of a composition comprising a naked anti-CSAp MAb or fragment thereof or a naked antibody fusion protein or fragment thereof of any one of the anti-CSAp antibodies of the present invention (ii) formulating the naked CSAp MAb or fragment thereof or antibody fusion protein or fragment thereof in a pharmaceutically suitable excipient.

In an additional aspect, the invention provides conjugates in which the hMu-9, human Mu-9, or cMu-9 is bonded to a diagnostic/detection or therapeutic reagent.

In a further aspect, the invention provides that unconjugated (naked) hMu-9, human Mu-9, or cMu-9 is administered in combination with other traditional as well as experimental therapy modalities, such as radiation, chemotherapy and surgery, or even with conjugates involving other, non-CSAp antibodies, and that the combination(s) may be given simultaneously or at different times in the therapy cycle.

In still another aspect, the invention provides methods of diagnosing/detecting or treating a malignancy that include administering an effective amount of the aforementioned antibodies or conjugates. The antibodies or conjugates may be formulated in a pharmaceutically acceptable vehicle.

In a further aspect, the invention provides isolated polynucleotides that comprise DNA sequences encoding the amino acid sequences of the CDRs of the light and heavy chain variable regions of the hMu-9, human Mu-9, or cMu-9 mAbs. Similarly, the invention provides isolated polynucleotides that comprise DNA sequences encoding the amino acid sequence of the light and heavy chain variable regions of the hMu-9, human Mu-9, or cMu-9 mAbs.

In yet another aspect, the invention provides amino acid sequences of the CDRs of the light and heavy chain variable regions of a Mu-9 antibody.

The present invention also seeks to provide inter alia a bi-specific antibody or antibody fragment having at least one arm that specifically binds a targeted tissue and at least one other arm that specifically binds a targetable conjugate that can be modified for use in a wide variety of diagnostic and therapeutic applications.

The present inventors have discovered that it is advantageous to raise bsAbs against a targetable conjugate that is capable of carrying one or more diagnostic/detection or therapeutic agents. By utilizing this technique, the characteristics of the chelator, metal chelate complex, therapeutic agent or diagnostic/detection agent can be varied to accommodate differing applications, without raising new bsAbs for each new application. Further, by using this approach, two or more distinct chelators, metal chelate complexes or therapeutic agents can be used with the inventive bsAb.

Provided in the present invention is a method of treating or identifying diseased tissues in a subject, comprising:

(A) administering to a subject a bi-specific antibody or antibody fragment having at least one arm that specifically binds a targeted tissue and at least one other arm that specifically binds a targetable conjugate, wherein the arm that specifically binds a targeted tissue is a Mu-9 antibody;

(B) optionally, administering to the subject a clearing composition, and allowing said composition to clear non-localized antibodies or antibody fragments from circulation;

(C) administering to the subject a first targetable conjugate which comprises a carrier portion which comprises or bears at least one epitope recognizable by said at least one other arm of said bi-specific antibody or antibody fragment, and one or more conjugated therapeutic or diagnostic agents; and (D) when said therapeutic agent is an enzyme, further administering to the subject
1) a prodrug, when said enzyme is capable of converting said prodrug to a drug at the target site; or
2) a drug which is capable of being detoxified in said subject to form an intermediate of lower toxicity, when said enzyme is capable of reconverting said detoxified intermediate to a toxic form, and, therefore, of increasing the toxicity of said drug at the target site, or
3) a prodrug which is activated in said subject through natural processes and is subject to detoxification by conversion to an intermediate of lower toxicity, when said enzyme is capable of reconverting said detoxified intermediate to a toxic form, and, therefore, of increasing the toxicity of said drug at the target site, or
4) a second targetable conjugate which comprises a carrier portion which comprises or bears at least one epitope recognizable by said at least one other arm of said bi-specific antibody or antibody fragment, and a prodrug, when said enzyme is capable of converting said prodrug to a drug at the target site.

The invention further provides a targetable conjugate that comprises at least two HSG haptens.

Also contemplated herein is a method for detecting or treating tumors expressing CSAp in a mammal, comprising:

(A) administering an effective amount of a bispecific antibody or antibody fragment comprising at least one arm that specifically binds a targeted tissue and at least one other arm that specifically binds a targetable conjugate, wherein the one arm that specifically binds a targeted tissue is a Mu-9 antibody or fragment thereof; and (B) administering a targetable conjugate selected from the group consisting of
(i) DOTA-Phe-Lys(HSG)-D-Tyr-Lys(HSG)-NH$_2$;
(ii) DOTA-Phe-Lys(HSG)-Tyr-Lys(HSG)-NH$_2$;
(iii) Ac-Lys(HSG)D-Tyr-Lys(HSG)-Lys(Tscg-Cys)-NH$_2$;

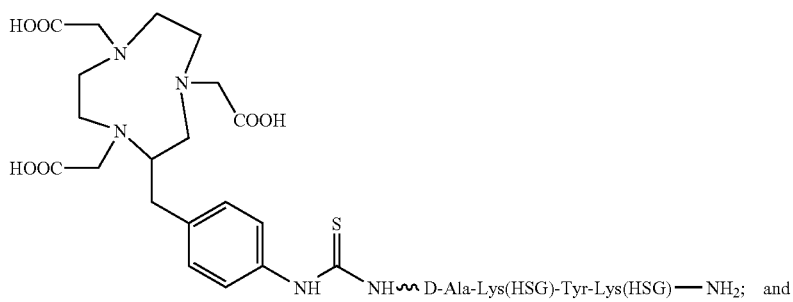

(iv)

D-Ala-Lys(HSG)-Tyr-Lys(HSG)—NH$_2$; and

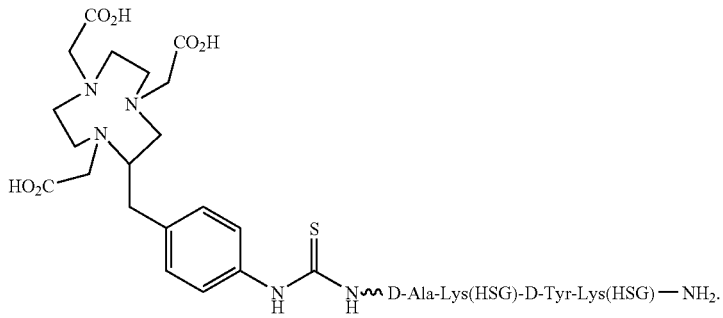

D-Ala-Lys(HSG)-D-Tyr-Lys(HSG)—NH₂.

(v)

This method optionally comprises administering to the subject a clearing composition, and allowing the composition to clear non-localized antibodies or antibody fragments from circulation.

Further, the invention provides a kit useful for treating or identifying diseased tissues in a subject comprising:

(A) a bi-specific antibody or antibody fragment having at least one arm that specifically binds a targeted tissue and at least one other arm that specifically binds a targetable conjugate, wherein said one arm that specifically binds a targeted tissue is a Mu-9 antibody or fragment thereof, (B) a first targetable conjugate which comprises a carrier portion which comprises or bears at least one epitope recognizable by said at least one other arm of said bi-specific antibody or antibody fragment, and one or more conjugated therapeutic or diagnostic agents; and (C) optionally, a clearing composition useful for clearing non-localized antibodies and antibody fragments; and (D) optionally, when the therapeutic agent conjugated to said first targetable conjugate is an enzyme, 1) a prodrug, when said enzyme is capable of converting said prodrug to a drug at the target site; or 2) a drug which is capable of being detoxified in said subject to form an intermediate of lower toxicity, when said enzyme is capable of reconverting said detoxified intermediate to a toxic form, and, therefore, of increasing the toxicity of said drug at the target site, or 3) a prodrug which is activated in said subject through natural processes and is subject to detoxification by conversion to an intermediate of lower toxicity, when said enzyme is capable of reconverting said detoxified intermediate to a toxic form, and, therefore, of increasing the toxicity of said drug at the target site, or 4) a second targetable conjugate which comprises a carrier portion which comprises or bears at least one epitope recognizable by said at least one other arm of said bi-specific antibody or antibody fragment, and a prodrug, when said enzyme is capable of converting said prodrug to a drug at the target site.

As described herein, the targetable conjugate may consist of:

(i) DOTA-Phe-Lys(HSG)-D-Tyr-Lys(HSG)-NH₂;
(ii) DOTA-Phe-Lys(HSG)-Tyr-Lys(HSG)-NH₂;
(iii) Ac-Lys(HSG)D-Tyr-Lys(HSG)-Lys(Tscg-Cys)-NH₂;

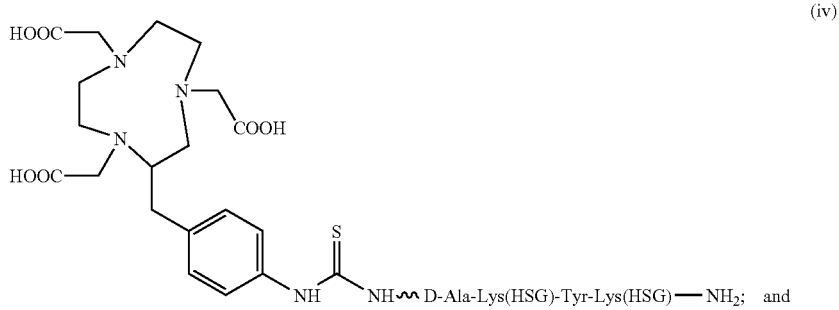

D-Ala-Lys(HSG)-Tyr-Lys(HSG)—NH₂; and (iv)

-continued

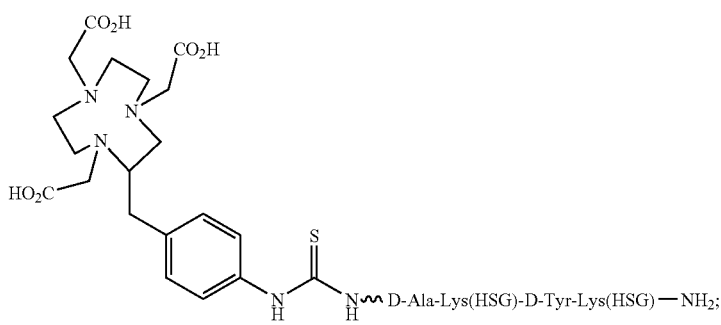

(v)

The invention also relates to a method of screening for a targetable conjugate comprising:

(A) contacting the targetable construct with a bi-specific antibody or antibody fragment having at least one arm that specifically binds a targeted tissue and at least one other arm that specifically binds said targetable conjugate to give a mixture, wherein the one arm that specifically binds a targeted tissue is a Mu-9 antibody or fragment thereof; and (B) optionally incubating said mixture; and (C) analyzing said mixture.

The invention further provides a method for imaging malignant tissue or cells in a mammal expressing CSAp, comprising:

(A) administering an effective amount of a bispecific antibody or antibody fragment comprising at least one arm that specifically binds a targeted tissue and at least one other arm that specifically binds a targetable conjugate, wherein the one arm that specifically binds a targeted tissue is a Mu-9 antibody or fragment thereof; and (B) administering a targetable conjugate selected from the group consisting of
(i) DOTA-Phe-Lys(HSG)-D-Tyr-Lys(HSG)-NH$_2$;
(ii) DOTA-Phe-Lys(HSG)-Tyr-Lys(HSG)-NH$_2$;
(iii) Ac-Lys(HSG)D-Tyr-Lys(HSG)-Lys(Tscg-Cys)-NH$_2$;

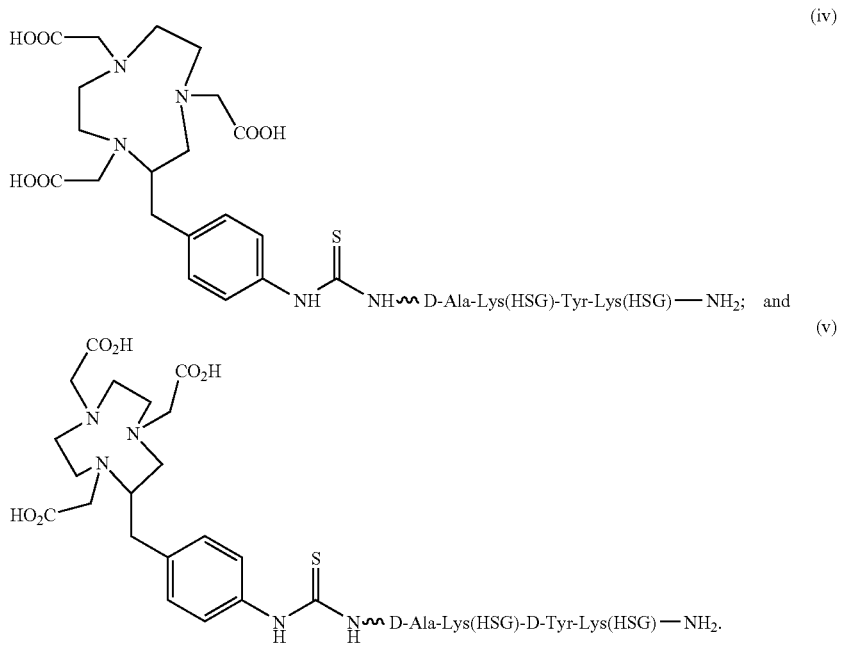

The invention also provides a method of intraoperatively, endoscopically and intravascularly identifying/disclosing diseased tissues expressing CSAp in a subject, comprising the administration of a detectable amount of a CSAp-labeled antibody, preferably a fragment or subfragment, whereby the label is detected by a suitable probe or miniature camera within 48 hours of said labeled CSAp antibody/fragment administration, without the need of a clearing agent for non-targeted, labeled antibody or fragment.

In a related vein, the invention provides a method of intraoperatively identifying/disclosing diseased tissues expressing CSAp, in a subject, comprising:

(A) administering an effective amount of a bispecific antibody or antibody fragment comprising at least one arm that specifically binds a targeted tissue expressing CSAp and at least one other arm that specifically binds a targetable conjugate, wherein the one arm that specifically binds a targeted tissue is a Mu-9 antibody or fragment thereof; and (B) administering a targetable conjugate selected from the group consisting of (i) DOTA-Phe-Lys(HSG)-D-Tyr-Lys(HSG)-NH$_2$;

(ii) DOTA-Phe-Lys(HSG)-Tyr-Lys(HSG)-NH$_2$;

(iii) Ac-Lys(HSG)D-Tyr-Lys(HSG)-Lys(Tscg-Cys)-NH$_2$;

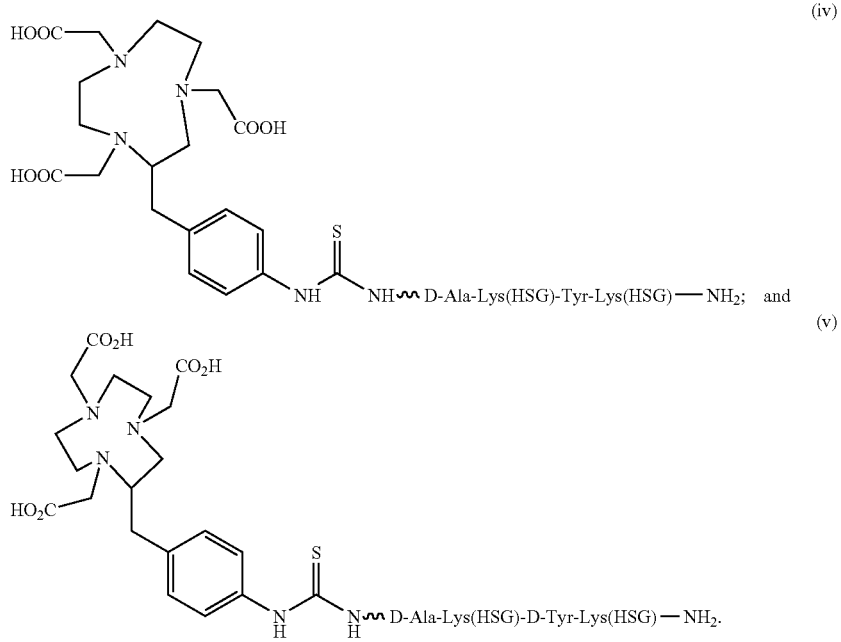

(iv)

(v)

The invention further relates to a method for the endoscopic identification of diseased tissues expressing CSAp, in a subject, comprising:

(A) administering an effective amount of a bispecific antibody or antibody fragment comprising at least one arm that specifically binds a targeted tissue expressing CSAp and at least one other arm that specifically binds a targetable conjugate wherein the one arm that specifically binds a targeted tissue is a Mu-9 antibody or fragment thereof; and (B) administering a targetable conjugate selected from the group consisting of (i) DOTA-Phe-Lys(HSG)-D-Tyr-Lys(HSG)-NH$_2$;

(ii) DOTA-Phe-Lys(HSG)-Tyr-Lys(HSG)-NH$_2$;

(iii) Ac-Lys(HSG)D-Tyr-Lys(HSG)-Lys(Tscg-Cys)-NH$_2$;

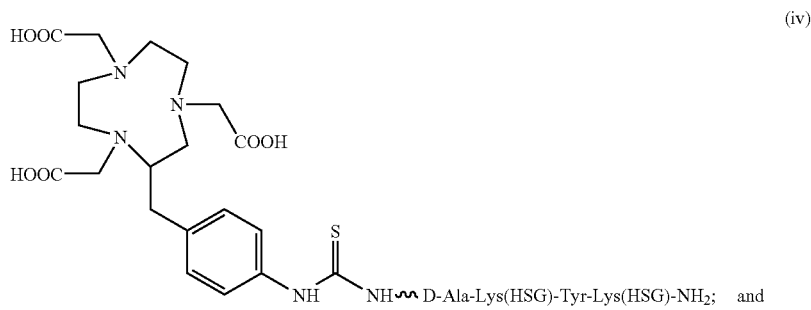

(iv)

-continued (v)

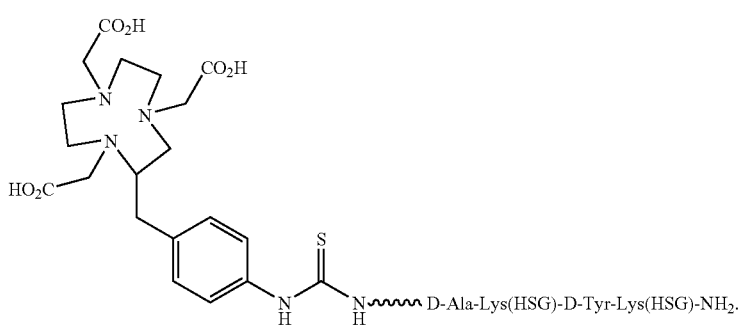

Also provided herein is a method for the intravascular identification of diseased tissues expressing CSAp, in a subject, comprising:

(A) administering an effective amount of a bispecific antibody or antibody fragment comprising at least one arm that specifically binds a targeted tissue expressing CSAp and at least one other arm that specifically binds a targetable conjugate wherein the one arm that specifically binds a targeted tissue is a Mu-9 antibody or fragment thereof; and (B) administering a targetable conjugate selected from the group consisting of
(i) DOTA-Phe-Lys(HSG)-D-Tyr-Lys(HSG)-NH$_2$;
(ii) DOTA-Phe-Lys(HSG)-Tyr-Lys(HSG)-NH$_2$;
(iii) Ac-Lys(HSG)D-Tyr-Lys(HSG)-Lys(Tscg-Cys)-NH$_2$;

ing site which specifically binds to a CSAp antigen, and has a second antibody binding site which specifically binds to a hapten, and permitting the antibody fragment to accrete at target sites;

(b) optionally clearing non-targeted antibody fragments using a galactosylated anti-idiotype clearing agent if the bispecific fragment is not largely cleared from circulation within about 24 hours of injection, and injecting a bivalent labeled hapten, which quickly localizes at the target site and clears through the kidneys;

(c) detecting the presence of the hapten by close-range detection of elevated levels of accreted label at the target sites with detection means, within 48 hours of the first injection,

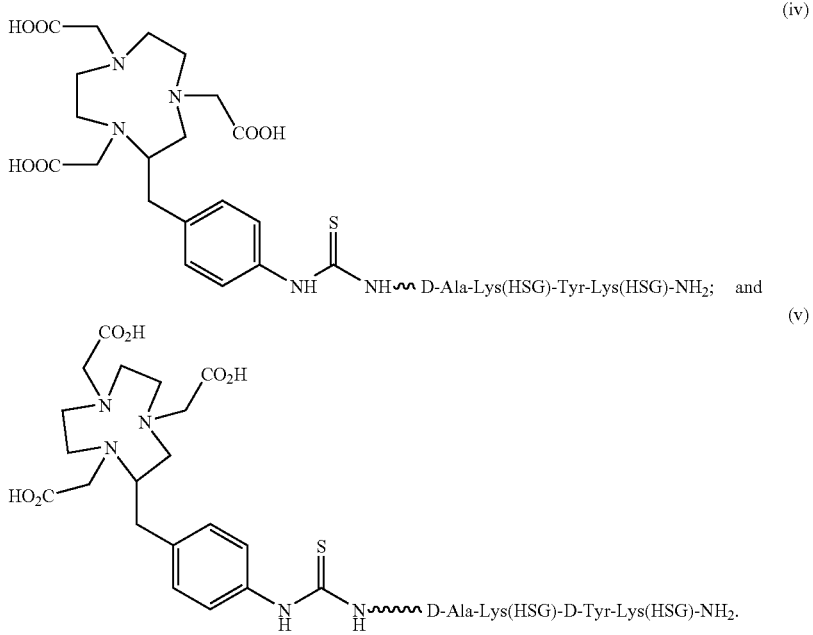

The invention also relates to a method of detection of lesions during an endoscopic, laparoscopic, intravascular catheter, or surgical procedure, wherein the method comprises:

(a) injecting a subject who is to undergo such a procedure with a bispecific antibody F(ab)$_2$ or F(ab')$_2$ fragment, wherein the bispecific antibody or fragment has a first antibody, bindand conducting said procedure, wherein said detection is performed without the use of a contrast agent or subtraction agent.

In a preferred embodiment, the hapten is labeled with a diagnostic radioisotope, a MRI image enhancing agent or a fluorescent label.

The invention further relates to a method for close-range lesion detection, during an operative, intravascular, laparoscopic, or endoscopic procedure, wherein the method comprises:

(a) injecting a subject to such a procedure parenterally with an effective amount of a Mu-9 immunoconjugate or fragment thereof;

(b) conducting the procedure within 48 hours of the injection;

(c) scanning the accessed interior of the subject at close range with a detection means for detecting the presence of said labeled antibody or fragment thereof; and (d) locating the sites of accretion of said labeled antibody or fragment thereof by detecting elevated levels of said labeled antibody or fragment thereof at such sites with the detection means.

In the above examples of intraoperative, endoscopic and intravascular uses, the label attached to the diagnostic compound is capable of being detected by a suitable instrument or probe, including miniature cameras, which are made for said label detection (e.g., a gamma-detecting probe when a gamma-emitting isotope is the diagnostic/detection conjugate) (see Goldenberg, U.S. Pat. Nos. 5,716,595, 6,096,289 and U.S. application Ser. No. 09/348,818, incorporated herein by reference in their entirety.

These and other aspects and embodiments of the invention will become apparent by reference to the following specification and appended claims.

BRIEF DESCRIPTION OF THE FIGURES

FIG. 1 shows the DNA and amino acid sequences of the murine Mu-9 heavy and light chain variable regions. FIG. 1A shows the DNA and amino acid sequences of the Mu-9VH obtained by RT-PCR. FIG. 1B shows the DNA and amino acid sequences of the functional Mu-9Vk (Vk2) obtained by cDNA screening. Amino acid sequences encoded by the corresponding DNA sequences are given as one letter codes below the nucleotide sequence. Numbering of the nucleotide sequence is on the right side. The amino acid residues in the CDR regions are shown in bold and underlined. Kabat's Ig molecule numbering is used for amino acid residues as shown by the numbering above the amino acid residues. The residues numbered with a letter only are the insertion residues defined by Kabat numbering scheme and have the same preceding digits as the previous one. For example, residues 82, 82A, 82B, and 82C in FIG. 1A are indicated as 82, A, B, and C, respectively.

FIG. 2 shows the DNA and amino acid sequences of the chimeric Mu-9 (cMu-9) heavy and light chain variable regions expressed in Sp2/0 cells. FIG. 2A shows the DNA and amino acid sequences of the cMu-9VH. FIG. 2B shows the double-stranded DNA and amino acid sequences of the cMu-9Vk. Amino acid sequences encoded by the corresponding DNA sequences are given as one letter codes. The amino acid residues in the CDR regions are shown in bold and underlined. Numbering of the nucleotide sequence is on the right side. The numbering of amino acids is same as that in FIG. 1. The restriction sites used for constructing the cMu-9 are underlined and indicated.

FIG. 3 shows the alignment of the amino acid sequences of heavy and light chain variable regions of a human antibody, Mu-9 and hMu-9. FIG. 3A shows the VH amino acid sequence alignment of the human antibody EU (FR1-3) and NEWM (FR4) with Mu-9 and hMu-9 and FIG. 3B shows the Vκ amino acid sequence alignment of the human antibody WOL with Mu-9 and hMu-9. Dots indicate the residues in Mu-9 that are identical to the corresponding residues in the human antibodies. Boxed regions represent the CDR regions. Both N- and C-terminal residues (underlined) of hMu-9 are fixed by the staging vectors used and not compared with the human antibodies. Kabat's Ig molecule number scheme is used to number the residues as in FIG. 1.

FIG. 4 shows the DNA and amino acid sequences of the humanized Mu-9 (hMu-9) heavy and light chain variable regions expressed in Sp2/0 cells. FIG. 4A shows the DNA and amino acid sequences of the hMu-9VH and FIG. 4B shows the DNA and amino acid sequences of the hMu-9Vκ. Numbering of the nucleotide sequence is on the right side. Amino acid sequences encoded by the corresponding DNA sequences are given as one letter codes. The amino acid residues in the CDR regions are shown in bold and underlined. Kabat's Ig molecule numbering scheme is used for amino acid residues as in FIG. 1 A and FIG. 1B.

DETAILED DESCRIPTION

I. Overview

Figure 5:
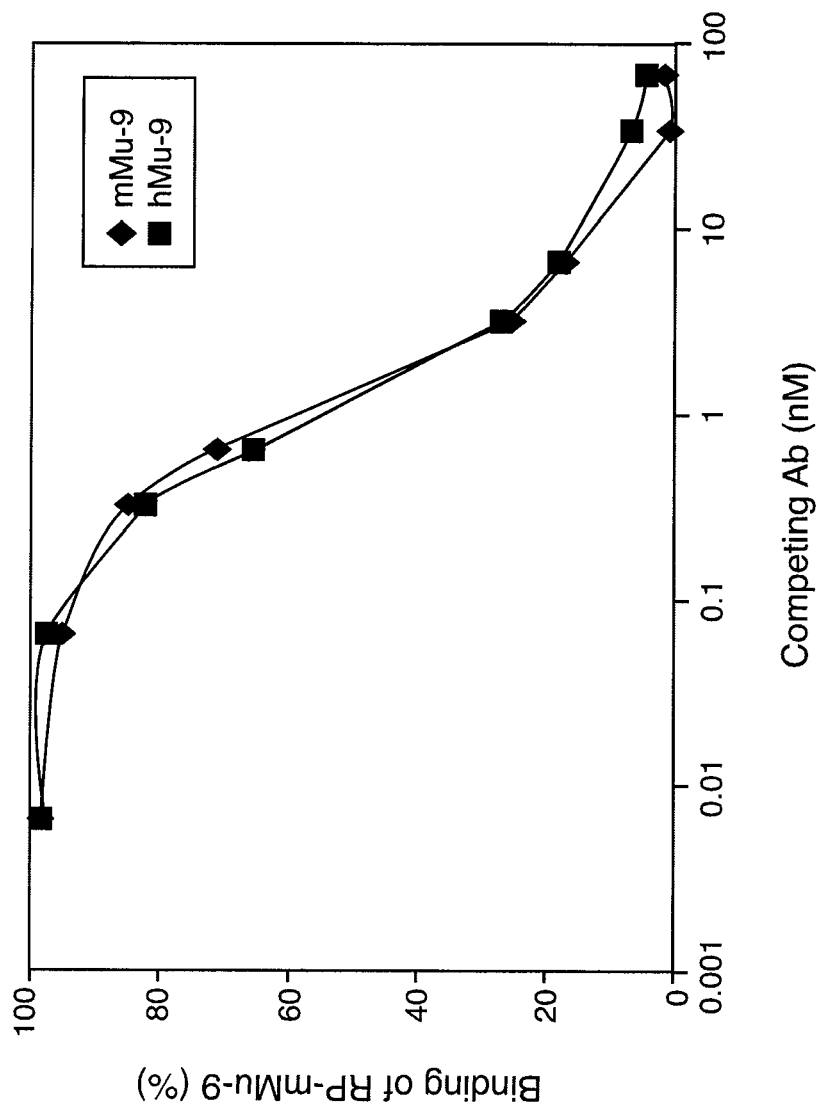
FIG. 5 shows a comparison of mMu-9 and hMu-9 in competitive binding assays. Varying concentrations of competing Abs were used to compete with the binding of a constant amount of HRP-mMu-9 to the antigen coated wells. hMu-9 showed comparable blocking activity as that of mMu-9. A comparison of mMu-9 and cMu-9 can be found in the publication by Krishnan et al. (Cancer, 80:2667-2674 (1997)).

The present invention encompasses antibodies and antibody fragments. The antibody fragments are antigen binding portions of an antibody, such as $F(ab')_2$, $F(ab)_2$, Fab', Fab, and the like. The antibody fragments bind to the same antigen that is recognized by the intact antibody. For example, an anti-CSAp monoclonal antibody fragment binds to an epitope of CSAp.

The term "antibody fragment" also includes any synthetic or genetically engineered protein that acts like an antibody by binding to a specific antigen to form a complex. For example, antibody fragments include isolated fragments, "Fv" fragments, consisting of the variable regions of the heavy and light chains, recombinant single chain polypeptide molecules in which light and heavy chain variable regions are connected by a peptide linker ("sFv proteins"), and minimal recognition units consisting of the amino acid residues that mimic the "hypervariable region." Three of these so-called "hypervariable" regions or "complementarity-determining regions" (CDR) are found in each variable region of the light or heavy chain. Each CDR is flanked by relatively conserved framework regions (FR). The FR are thought to maintain the structural integrity of the variable region. The CDRs of a light chain and the CDRs of a corresponding heavy chain form the antigen-binding site. The "hypervariability" of the CDRs accounts for the diversity of specificity of antibodies.

Also contemplated in the present invention are human, chimeric and humanized anti-CSAp antibodies and fragments thereof. The human anti-CSAp antibody of the present invention is preferably against the Mu-9 antigen. A fully human antibody is an antibody obtained, for example, from transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13 (1994), Lonberg et al., *Nature* 368:856 (1994), and Taylor et al., *Int. Immun.* 6:579 (1994). A fully human antibody also can be constructed by genetic or chromosomal transfection methods, as well as phage display technology, all of which are known in the art. See, for example, McCafferty et al., *Nature* 348:552-553 (1990) for the production of human antibodies and fragments thereof in vitro, from immunoglobulin variable domain gene repertoires from unimmunized donors. In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for their review, see e.g. Johnson and Chiswell, *Current Opinion in Structural Biology* 3:5564-571 (1993).

Human antibodies may also be generated by in vitro activated B cells. See U.S. Pat. Nos. 5,567,610 and 5,229,275, which are incorporated in their entirety by reference.

The present invention also provides a chimeric anti-CSAp monoclonal antibody or fragment thereof. The chimeric anti-CSAp antibody or fragment contains a light and heavy chain variable region of a non-human anti-CSAp antibody, which are joined to the light and heavy chain constant regions of a human antibody. Preferably, the light and heavy chain variable regions come from a murine anti-CSAp antibody. In a preferred embodiment, the anti-CSAp antibody binds a Mu-9 epitope on the CSAp antigen. Accordingly, a Mu-9 antibody is an anti-CSAp antibody that binds to the Mu-9 epitope.

The process for making cMu-9 is described in detail below. Briefly, cDNAs encoding the Vκ and $V_H$ regions of the Mu-9 mAb have been isolated and separately recombinantly subcloned into mammalian expression vectors that contain the genes a human κ light chain constant region sequence and a human γ1 chain sequence, respectively. Cotransfection of mammalian cells with these two recombinant DNAs resulted in expression of a cMu-9 mAb that, like the parent Mu-9 mAb, bound avidly to the CSAp antigen.

In a preferred embodiment, the light chain variable region of the cMu-9 antibody comprises the amino acids of SEQ. ID NO: (FIG. 2B) or the heavy chain variable region of the cMu-9 antibody comprises the amino acids of SEQ. ID NO: (FIG. 2A). Still preferred, the light chain variable region of the cMu-9 antibody comprises the amino acids of SEQ. ID NO: (FIG. 2B) and the heavy chain variable region of the cMu-9 antibody comprises the amino acids of SEQ. ID NO: (FIG. 2A).

The present invention further provides a humanized Mu-9 (hMu-9) monoclonal antibody (mAb) or a fragment thereof. The hMu-9 antibody or fragment contains the complementarity-determining regions (CDRs) of the light and heavy chain variable regions of a non-human Mu-9 antibody, which are joined to the framework (FR) regions of the light and heavy chain variable regions of a human antibody, which are subsequently joined to the light and heavy chain constant regions of a human antibody. This humanized antibody or fragment retains the CSAp antigen specificity of the parental Mu-9 antibody, but is less immunogenic in a human subject.

Methods for making hMu-9 are described in detail below. Briefly, however, to make hMu-9, the CDRs of the Vκ and $V_H$ DNAs have been recombinantly linked to the framework (FR) sequences of the human Vκ and $V_H$ regions, respectively, which are subsequently linked, respectively, to the human kappa and γ1 constant regions, so as to express in mammalian cells as described above hMu-9.

In another embodiment of the present invention, hMu-9, the CDRs of the light chain variable region comprise CDR1 comprising amino acids 24 to 34 of SEQ ID NO: (FIG. 2B), CDR2 comprising amino acids 50 to 56 of SEQ ID NO: (FIG. 2B), and CDR3 comprising amino acids 89 to 97 of SEQ ID NO: (FIG. 2B); and the CDRs of the heavy chain variable region comprise CDR1 comprising amino acids 31 to 35 of SEQ ID NO: (FIG. 2A), CDR2 comprising amino acids 50 to 64 of SEQ ID NO: (FIG. 2A), and CDR3 comprising amino acids 95 to 97 of SEQ ID NO: (FIG. 2A).

Other preferred embodiments of the invention include anti-CSAp antibody fragments comprising the light chain variable region of SEQ ID NO: (FIG. 4B) and/or the heavy chain variable region of SEQ ID NO: (FIG. 4A).

In this specification, the expressions "cMu-9" or "cMu-9 mAb" are intended to refer to the chimeric monoclonal antibody constructed by joining or subcloning the non-human Vκ and VH regions to the human constant light and heavy chains, respectively. The expressions "hMu-9" or "hMu-9 mAb" are intended to refer to the humanization of the chimeric monoclonal antibody by replacing the non-human FR sequences in cMu-9 with that of human framework regions. Preferably, the anti-CSAp humanized antibodies and fragments thereof of the present invention comprise framework region sequences where at least one amino acid of the corresponding non-human light or heavy chain framework regions is retained. Preferably, an amino acid from the murine antibody FR is retained in the same position of the corresponding humanized antibody.

A chimeric antibody is a recombinant protein that contains the variable domains including the complementarity determining regions (CDRs) of an antibody derived from one species, preferably a rodent antibody, while the constant domains of the antibody molecule is derived from those of a human antibody. For veterinary applications, the constant domains of the chimeric antibody may be derived from that of other species, such as a cat or dog.

A humanized antibody is a recombinant protein in which the CDRs from an antibody from one species; e.g., a rodent antibody, is transferred from the heavy and light variable chains of the rodent antibody into human heavy and light variable domains. The constant domains of the antibody molecule is derived from those of a human antibody.

The present invention also contemplates anti-CSAp antibody fragments. The antibody fragments are antigen binding portions of an antibody, such as F(ab')$_2$, F(ab)$_2$, Fab', Fab, and the like. The antibody fragments contain one or more CDRs of the intact antibody and bind to the same antigen that is recognized by the intact antibody. For example, an anti-colon-specific antigen-p (CSAp) monoclonal antibody fragment binds to an epitope of colon-specific antigen-p.

Also, the present invention provides a bi-specific antibody or antibody fragment having at least one arm that is reactive against a targeted tissue and at least one other arm that is reactive against a targetable construct. The targetable construct is comprised of a carrier portion and at least 2 units of a recognizable hapten. Examples of recognizable haptens include, but are not limited to, histamine succinyl glycine (HSG) and fluorescein isothiocyanate. The targetable construct may be conjugated to a variety of agents useful for treating or identifying diseased tissue. Examples of conjugated agents include, but are not limited to, chelators, metal chelate complexes, drugs, toxins (e.g., ricin, abrin, ribonuclease, DNase I, *Staphylococcal* enterotoxin-A, pokeweed antiviral protein, gelonin, diphtherin toxin, *Pseudomonas* exotoxin, *Pseudomonas* endotoxin) and other effector molecules. Additionally, enzymes useful for activating a prodrug or increasing the target-specific toxicity of a drug can be conjugated to the targetable construct. Thus, the use of bsAb which are reactive to a targetable construct allows a variety of therapeutic and diagnostic/detection applications to be performed without raising new bsAb for each application.

Additionally, the present invention encompasses a method for detecting or treating target diseased cells or tissues in a mammal, comprising administering an effective amount of a bispecific antibody or antibody fragment comprising at least one arm that specifically binds a targeted tissue and at least one other arm that specifically binds a targetable conjugate.

Antibodies that do not target the CSAp antigen can be used in this invention. For example, antibodies against other antigens associated with carcinomas, particularly carcinomas of the gastrointestinal system (colon, rectum, pancreas tumors) and ovarian cancer, can be combined with CSAp antibodies and also used as fusion partners with CSAp antibodies. Antibodies against intracellular and other antigens associated with necrosis, angiogenesis factors, immune response factors (e.g., CD40), as well as products of oncogenes, may also be used in combination with CSAp antibodies and as fusion partners for CSAp antibodies. Anti-necrosis antibodies are described in Epstein et al., U.S. Pat. Nos. 6,071,491, 6,017,514, 5,019,368 and 5,882,626, and are incorporated by reference.

Immunoconjugates between chimeric, humanized and human anti-CSAp antibodies or fragments thereof and a diagnostic or therapeutic reagent, formulated in pharmaceutically acceptable vehicles (see, e.g., Remington's Pharmaceutical Sciences, 18$^{th}$ ed., Mack Publishing Co., Easton, Pa., 1990) can be prepared. An immunoconjugate is a conjugate of an antibody component with a therapeutic or diagnostic agent. As random (non-specific) conjugation often results in products with reduced binding activity, it is preferred to use conjugates in which the reagent is site-specifically bound to the antibody through, for example, carbohydrate moieties, such as through oxidized carbohydrate derivatives. Carbohydrate moieties can be introduced into an antibody by site-specific mutagenesis without altering the immunoreactivity. Methods for the production of such conjugates and their use in diagnostics and therapeutics are provided, for example in Shih et al., U.S. Pat. No. 5,057,313; Shih et al., Int. J. Cancer 41: 832 (1988); and Hansen et al., U.S. Pat. No. 5,443,953, the contents of which are incorporated herein by reference. Direct linkage of the reagent to oxidized carbohydrate without the use of a polymeric carrier is described in McKearn et al., U.S. Pat. No. 5,156,840, which is also incorporated by reference.

A wide variety of diagnostic/detection and therapeutic reagents can be advantageously conjugated to the antibodies of the invention. These include, but are not limited to, different classes of chemotherapeutic agents, such as anthracyclines, antibiotics, alkylating agents, anti-mitotic agents, anti-angiogenesis agents, plant alkaloids, COX-inhibitors, antimetabolites (e.g., methotrexate), doxorubicin, CPT-11, oxaliplatin, taxol and other taxanes, and the like; chelators, such as DTPA, to which detectable labels such as fluorescent molecules or cytotoxic agents, such as heavy metals or radionuclides can be complexed; and toxins such as *Pseudomonas* exotoxin, RNAse, gelonin, and the like.

A therapeutic agent is a molecule or atom which is administered separately, concurrently or sequentially with an antibody moiety or conjugated to an antibody moiety, i.e., antibody or antibody fragment, or a subfragment, and is useful in the treatment of a disease. Examples of therapeutic agents include antibodies, antibody fragments, drugs, toxins, enzymes, enzyme-inhibitors, nucleases, hormones, hormone antagonists, immunomodulators, chelators, boron compounds, uranium atoms, photoactive agents or dyes and radionuclides. Radionuclides in therapeutic agents, which substantially decay by beta-particle emission include, but are not limited to: P-32, P-33, Sc-47, Fe-59, Cu-64, Cu-67, Se-75, As-77, Sr-89, Y-90, Mo-99, Rh-105, Pd-109, Ag-111, I-125, I-131, Pr-142, Pr-143, Pm-149, Sm-153, Th-161, Ho-166, Er-169, Lu-177, Re-186, Re-188, Re-189, Ir-194, Au-198, Au-199, Pb-211, Pb-212, and Bi-213. Maximum decay energies of useful beta-particle-emitting nuclides are preferably 20-5,000 keV, more preferably 100-4,000 keV, and most preferably 500-2,500 keV. Also preferred are radionuclides that substantially decay with Auger-emitting particles. For example, Co-58, Ga-67, Br-80m, Tc-99m, Rh-103m, Pt-109, In-111, Sb-119, I-125, Ho-161, Os-189m and Ir-192. Decay energies of useful Auger-particle-emitting nuclides are preferably <1,000 keV, more preferably <100 keV, and most preferably <70 keV. Also preferred are radionuclides that substantially decay with generation of alpha-particles. Such radionuclides include, but are not limited to: Dy-152, At-211, Bi-212, Ra-223, Rn-219, Po-215, Bi-211, Ac-225, Fr-221, At-217, Bi-213 and Fm-255. Decay energies of useful alpha-particle-emitting radionuclides are preferably 2,000-10,000 keV, more preferably 3,000-8,000 keV, and most preferably 4,000-7,000 keV.

Enzymes are also useful therapeutic agents. For example, alkaline phosphatase for use in combination with phosphate-containing prodrugs (U.S. Pat. No. 4,975,278); arylsulfatase for use in combination with sulfate-containing prodrugs (U.S. Pat. No. 5,270,196), peptidases and proteases, such as serratia protease, thermolysin, subtilisin, carboxypeptidase (U.S. Pat. Nos. 5,660,829; 5,587,161; 5,405,990) and cathepsins (including cathepsin B and L), for use in combination with peptide-based prodrugs; D-alanylcarboxypeptidases for use in combination with D-amino acid-modified prodrugs; carbohydrate-cleaving enzymes such as beta-galactosidase and neuraminidase for use in combination with glycosylated prodrugs (U.S. Pat. Nos. 5,561,119; 5,646,298); .beta.-lactamase for use in combination with beta-lactam-containing prodrugs; penicillin amidases, such as penicillin-V-amidase (U.S. Pat. No. 4,975,278) or penicillin-G-amidase, for use in combination with drugs derivatized at their amino nitrogens with phenoxyacetamide or phenylacetamide groups; and cytosine deaminase (U.S. Pat. Nos. 5,338,678; 5,545,548) for use in combination with 5-fluorocytosine-based prodrugs (U.S. Pat. No. 4,975,278), are suitable therapeutic agents for the present invention.

Anti-angiogenic agents (or angiogenesis inhibitors) suitable for use in combination therapy or for conjugating to antibodies include angiostatin, endostatin, vasculostatin, canstatin and maspin.

Other useful therapeutic agents include metals, such as those as part of a photodynamic therapy, and nuclides, such as those valuable in therapies based on neutron capture procedures. Specifically, zinc, aluminum, gallium, lutetium and palladium are useful for photodynamic therapy and B-10, Gd-157 and U-235 are useful for neutron capture therapy.

A diagnostic/detection agent is a molecule or atom which is administered conjugated to an antibody moiety, i.e., antibody or antibody fragment, or subfragment, and is useful in diagnosing/detecting a disease by locating the cells containing the disease-associated antigen. Useful diagnostic/detection agents include, but are not limited to, radioisotopes, dyes (such as with the biotin-streptavidin complex), radiopaque materials (e.g., iodine, barium, gallium, and thallium compounds and the like), contrast agents, fluorescent compounds or molecules and enhancing agents (e.g., paramagnetic ions) for magnetic resonance imaging (MRI). U.S. Pat. No. 6,331,175 describes MRI technique and the preparation of antibodies conjugated to a MRI enhancing agent and is incorporated in its entirety by reference. Preferably, the diagnostic/detection agents are selected from the group consisting of radioisotopes for nuclear imaging, intraoperative and endoscopic detection; enhancing agents for use in magnetic resonance imaging or in ultrasonography; radiopaque and contrast agents for X-rays and computed tomography; and fluorescent compounds for fluoroscopy, including endoscopic fluoroscopy. Fluorescent and radioactive agents conjugated to antibodies or used in bispecific, pretargeting methods, are particularly useful for endoscopic, intraoperative or intravascular detection of the targeted antigens associated with diseased tissues or clusters of cells, such as malignant tumors, as disclosed in Goldenberg U.S. Pat. Nos. 5,716,595, 6,096,289 and U.S. application Ser. No. 09/348,818, incorporated herein by reference in their entirety, particularly with gamma-, beta-, and positron-emitters. Radionuclides useful for positron emission tomography include, but are not limited to: F-18, Mn-51, Mn-52m, Fe-52, Co-55, Cu-62, Cu-64, Ga-68, As-72, Br-75, Br-76, Rb-82m, Sr-83, Y-86, Zr-89, Tc-94m, In-110, I-120, and I-124. Total decay energies of useful positron-emitting radionuclides are preferably <2,000 keV, more preferably under 1,000 keV, and most preferably <700 keV. Radionuclides useful as diagnostic agents utilizing gamma-ray detection include, but are not limited to: Cr-51, Co-57, Co-58, Fe-59, Cu-67, Ga-67, Se-75, Ru-97, Tc-99m, In-111, In-114m, I-123, I-125, I-131, Yb-169, Hg-197, and Tl-201. Decay energies of useful gamma-ray emitting radionuclides are preferably 20-2000 keV, more preferably 60-600 keV, and most preferably 100-300 keV.

Paramagnetic ions suitable for the present invention include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred.

Ions useful in other contexts, such as X-ray imaging, include but are not limited to lanthanum (III), gold (III), lead (II), and especially bismuth (III). Fluorescent labels include rhodamine, fluorescein and renographin. Rhodamine and fluorescein are often linked via an isothiocyanate intermediate.

Metals are also useful in diagnostic agents, including those for magnetic resonance imaging techniques. These metals include, but are not limited to: Gadolinium, manganese, iron, chromium, copper, cobalt, nickel, dysprosium, rhenium, europium, terbium, holmium and neodymium. In order to load an antibody component with radioactive metals or paramagnetic ions, it may be necessary to react it with a reagent having a long tail to which are attached a multiplicity of chelating groups for binding the ions. Such a tail can be a polymer such as a polylysine, polysaccharide, or other derivatized or derivatizable chain having pendant groups to which can be bound chelating groups such as, e.g., ethylenediaminetetraacetic acid (EDTA), diethylenetriaminepentaacetic acid (DTPA), porphyrins, polyamines, crown ethers, bis-thiosemicarbazones, polyoximes, and like groups known to be useful for this purpose. Chelates are coupled to the peptide antigens using standard chemistries. The chelate is normally linked to the antibody by a group which enables formation of a bond to the molecule with minimal loss of immunoreactivity and minimal aggregation and/or internal cross-linking. Other, more unusual, methods and reagents for conjugating chelates to antibodies are disclosed in U.S. Pat. No. 4,824,659 to Hawthorne, entitled "Antibody Conjugates," issued Apr. 25, 1989, the disclosure of which is incorporated herein in its entirety by reference. Particularly useful metal-chelate combinations include 2-benzyl-DTPA and its monomethyl and cyclohexyl analogs, used with diagnostic isotopes in the general energy range of 20 to 2,000 keV. The same chelates, when complexed with non-radioactive metals, such as manganese, iron and gadolinium are useful for MRI, when used along with the antibodies of the invention. Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates such as macrocyclic polyethers, which are of interest for stably binding nuclides, such as $^{223}$Ra for RAIT are encompassed by the invention.

Radiopaque and contrast materials are used for enhancing X-rays and computed tomography, and include iodine compounds, barium compounds, gallium compounds, thallium compounds, etc. Specific compounds include barium, diatrizoate, ethiodized oil, gallium citrate, iocarmic acid, iocetamic acid, iodamide, iodipamide, iodoxamic acid, iogulamide, iohexyl, iopamidol, iopanoic acid, iprocemic acid, iosefamic acid, ioseric acid, iosulamide meglumine, iosemetic acid, iotasul, iotetric acid, iothalamic acid, iotroxic acid, ioxaglic acid, ioxotrizoic acid, ipodate, meglumine, metrizamide, metrizoate, propyliodone, and thallous chloride.

As used herein, the term "subject" refers to any animal (i.e., vertebrates and invertebrates) including, but not limited to humans and other primatesbovines (e.g., cattle), ovines (e.g., sheep), caprines (e.g., goats), porcines (e.g., swine), equines (e.g., horses), canines (e.g., dogs), felines (e.g., cats), etc. It is not intended that the term be limited to a particular age or sex. Thus, adult and newborn subjects, as well as fetuses, whether male or female, are encompassed by the term.

II. Preparation of Antibodies

Monoclonal antibodies (MAbs) are a homogeneous population of antibodies to a particular antigen and the antibody comprises only one type of antigen binding site and binds to only one epitope on an antigenic determinant. Rodent monoclonal antibodies to specific antigens may be obtained by methods known to those skilled in the art. See, for example, Kohler and Milstein, *Nature* 256: 495 (1975), and Coligan et al. (eds.), CURRENT PROTOCOLS IN IMMUNOLOGY, VOL. 1, pages 2.5.1-2.6.7 (John Wiley & Sons 1991) [hereinafter "Coligan"]. Briefly, monoclonal antibodies can be obtained by injecting mice with a composition comprising an antigen, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

MAbs can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METH- ODS IN MOLECULAR BIOLOGY, VOL. 10, pages 79-104 (The Humana Press, Inc. 1992).

Abs to peptide backbones are generated by well-known methods for Ab production. For example, injection of an immunogen, such as (peptide)$_n$-KLH, wherein KLH is keyhole limpet hemocyanin, and n=1-30, in complete Freund's adjuvant, followed by two subsequent injections of the same immunogen suspended in incomplete Freund's adjuvant into immunocompetent animals, is followed three days after an i.v. boost of antigen, by spleen cell harvesting. Harvested spleen cells are then fused with Sp2/0-Ag14 myeloma cells and culture supernatants of the resulting clones analyzed for anti-peptide reactivity using a direct-binding ELISA. Fine specificity of generated Abs can be analyzed for by using peptide fragments of the original immunogen. These fragments can be prepared readily using an automated peptide synthesizer. For Ab production, enzyme-deficient hybridomas are isolated to enable selection of fused cell lines. This technique also can be used to raise antibodies to one or more of the chelates comprising the linker, e.g., In(III)-DTPA chelates. Monoclonal mouse antibodies to an In(III)-di-DTPA are known (Barbet '395 supra).

The antibodies used in the present invention are specific to a variety of cell surface or intracellular tumor-associated antigens as marker substances. These markers may be substances produced by the tumor or may be substances which accumulate at a tumor site, on tumor cell surfaces or within tumor cells, whether in the cytoplasm or in various organelles or sub-cellular structures, or even as part of the endothelium of vessels nourishing tumors or elaborated by the tumor vasculature. Among such tumor-associated markers are those disclosed by Herberman, "Immunodiagnosis of Cancer," in Fleisher ed., "The Clinical Biochemistry of Cancer," page 347 (American Association of Clinical Chemists, 1979) and in U.S. Pat. Nos. 4,150,149; 4,361,544; and 4,444,744.

Tumor-associated markers have been categorized by Herberman, supra, in a number of categories including oncofetal antigens, placental antigens, oncogenic or tumor virus associated antigens, tissue associated antigens, organ associated antigens, ectopic hormones and normal antigens or variants thereof. Occasionally, a sub-unit of a tumor-associated marker is advantageously used to raise antibodies having higher tumor-specificity, e.g., the beta-subunit of human chorionic gonadotropin (HCG) or the gamma region of carcino embryonic antigen (CEA), which stimulate the production of antibodies having a greatly reduced cross-reactivity to non-tumor substances as disclosed in U.S. Pat. Nos. 4,361,644 and 4,444,744.

After the initial raising of antibodies to the immunogen, the antibodies can be sequenced and subsequently prepared by recombinant techniques. Humanization and chimerization of murine antibodies and antibody fragments are well known to those skilled in the art. For example, humanized monoclonal antibodies are produced by transferring mouse complementary determining regions from heavy and light variable chains of the mouse immunoglobulin into a human variable domain, and then, substituting human residues in the framework regions of the murine counterparts. In a preferred embodiment, some human residues in the framework regions of the humanized anti-CSAp antibody or fragments thereof are replaced by their murine counterparts. It is also preferred that a combination of framework sequences from 2 different human antibodies are used for $V_H$. Still preferred, the two human antibodies are EU and NEWM. The constant domains of the antibody molecule is derived from those of a human antibody. The use of antibody components derived from humanized monoclonal antibodies obviates potential problems associated with the immunogenicity of murine constant regions.

A human antibody can be recovered from a transgenic mouse possessing human immunoglobulin loci. The mouse humoral immune system is humanized by inactivating the endogenous immunoglobulin genes and introducing human immunoglobulin loci. The human immunoglobulin loci are exceedingly complex and comprise a large number of discrete segments which together occupy almost 0.2% of the human genome. To ensure that transgenic mice are capable of producing adequate repertoires of antibodies, large portions of human heavy- and light-chain loci must be introduced into the mouse genome. This is accomplished in a stepwise process beginning with the formation of yeast artificial chromosomes (YACs) containing either human heavy- or light-chain immunoglobulin loci in germline configuration. Since each insert is approximately 1 Mb in size, YAC construction requires homologous recombination of overlapping fragments of the immunoglobulin loci. The two YACs, one containing the heavy-chain loci and one containing the light-chain loci, are introduced separately into mice via fusion of YAC-containing yeast spheroblasts with mouse embryonic stem cells. Embryonic stem cell clones are then microinjected into mouse blastocysts. Resulting chimeric males are screened for their ability to transmit the YAC through their germline and are bred with mice deficient in murine antibody production. Breeding the two transgenic strains, one containing the human heavy-chain loci and the other containing the human light-chain loci, creates progeny which produce human antibodies in response to immunization.

Unrearranged human immunoglobulin genes also can be introduced into mouse embryonic stem cells via microcell-mediated chromosome transfer (MMCT). See, e.g., Tomizuka et al., Nature Genetics, 16: 133 (1997). In this methodology microcells containing human chromosomes are fused with mouse embryonic stem cells. Transferred chromosomes are stably retained, and adult chimeras exhibit proper tissue-specific expression.

As an alternative, an antibody or antibody fragment of the present invention may be derived from human antibody fragments isolated from a combinatorial immunoglobulin library. See, e.g., Barbas et al., METHODS: A Companion to Methods in Enzymology 2: 119 (1991), and Winter et al., Ann. Rev. Immunol. 12: 433 (1994), which are incorporated by reference. Many of the difficulties associated with generating monoclonal antibodies by B-cell immortalization can be overcome by engineering and expressing antibody fragments in E. coli, using phage display. To ensure the recovery of high affinity, monoclonal antibodies a combinatorial immunoglobulin library must contain a large repertoire size. A typical strategy utilizes mRNA obtained from lymphocytes or spleen cells of immunized mice to synthesize cDNA using reverse transcriptase. The heavy- and light-chain genes are amplified separately by PCR and ligated into phage cloning vectors. Two different libraries are produced, one containing the heavy-chain genes and one containing the light-chain genes. Phage DNA is isolated from each library, and the heavy- and light-chain sequences are ligated together and packaged to form a combinatorial library. Each phage contains a random pair of heavy- and light-chain cDNAs and upon infection of E. coli directs the expression of the antibody chains in infected cells. To identify an antibody that recognizes the antigen of interest, the phage library is plated, and the antibody molecules present in the plaques are transferred to filters. The filters are incubated with radioactively labeled antigen and then washed to remove excess unbound ligand. A radioactive spot on the autoradiogram identifies a plaque that contains an antibody that binds the antigen. Cloning and expression vectors that are useful for producing a human immunoglobulin phage library can be obtained, for example, from STRATAGENE Cloning Systems (La Jolla, Calif.).

General techniques for cloning murine immunoglobulin variable domains are described, for example, by the publication of Orlandi et al., *Proc. Nat'l Acad. Sci. USA* 86: 3833 (1989), which is incorporated by reference in its entirety. Techniques for constructing chimeric antibodies are well known to those of skill in the art. As an example, Leung et al., *Hybridoma* 13:469 (1994), describe how they produced an LL2 chimera by combining DNA sequences encoding the $V_\kappa$ and $V_H$ domains of LL2 monoclonal antibody, an anti-CD22 antibody, with respective human κ and $IgG_1$ constant region domains. This publication also provides the nucleotide sequences of the LL2 light and heavy chain variable regions, $V_\kappa$ and $V_H$, respectively. Techniques for producing humanized MAbs are described, for example, by Jones et al., *Nature* 321: 522 (1986), Riechmann et al., *Nature* 332: 323 (1988), Verhoeyen et al., *Science* 239: 1534 (1988), Carter et al., *Proc. Nat'l Acad. Sci. USA* 89: 4285 (1992), Sandhu, *Crit. Rev. Biotech.* 12: 437 (1992), and Singer et al., *J. Immun.* 150: 2844 (1993), each of which is hereby incorporated by reference.

A chimeric antibody is a recombinant protein that contains the variable domains including the CDRs derived from one species of animal, such as a rodent antibody, while the remainder of the antibody molecule; i.e., the constant domains, is derived from a human antibody. Accordingly, a chimeric monoclonal antibody can also be humanized by replacing the sequences of the murine FR in the variable domains of the chimeric MAb with one or more different human FR. Specifically, mouse CDRs are transferred from heavy and light variable chains of the mouse immunoglobulin into the corresponding variable domains of a human antibody. As simply transferring mouse CDRs into human FRs often results in a reduction or even loss of antibody affinity, additional modification might be required in order to restore the original affinity of the murine antibody. This can be accomplished by the replacement of one or more some human residues in the FR regions with their murine counterparts to obtain an antibody that possesses good binding affinity to its epitope. See, for example, Tempest et al., *Biotechnology* 9:266 (1991) and Verhoeyen et al., *Science* 239: 1534 (1988). Further, the affinity of humanized, chimeric and human MAbs to a specific epitope can be increased by mutagenesis of the CDRs, so that a lower dose of antibody may be as effective as a higher dose of a lower affinity MAb prior to mutagenesis. See for example, WO0029584A1

Another method for producing the antibodies of the present invention is by production in the milk of transgenic livestock. See, e.g., Colman, A., *Biochem. Soc. Symp.*, 63: 141-147, 1998; U.S. Pat. No. 5,827,690, both of which are incorporated in their entirety by reference. Two DNA constructs are prepared which contain, respectively, DNA segments encoding paired immunoglobulin heavy and light chains. The DNA segments are cloned into expression vectors which contain a promoter sequence that is preferentially expressed in mammary epithelial cells. Examples include, but are not limited to, promoters from rabbit, cow and sheep casein genes, the cow α-lactoglobulin gene, the sheep β-lactoglobulin gene and the mouse whey acid protein gene. Preferably, the inserted fragment is flanked on its 3' side by cognate genomic sequences from a mammary-specific gene. This provides a polyadenylation site and transcript-stabilizing sequences. The expression cassettes are coinjected into the pronuclei of fertilized, mammalian eggs, which are then implanted into the uterus of a recipient female and allowed to gestate. After birth, the progeny are screened for the presence of both transgenes by Southern analysis. In order for the antibody to be present, both heavy and light chain genes must be expressed concurrently in the same cell. Milk from transgenic females is analyzed for the presence and functionality of the antibody or antibody fragment using standard immunological methods known in the art. The antibody can be purified from the milk using standard methods known in the art.

Preparation of Chimeric, Humanized and Human Anti-CSAp Antibodies

Also contemplated in the present invention are human, humanized and chimeric anti-CSAp monoclonal antibodies used in combination with other human or reengineered (e.g., chimerized, humanized) antibodies, such as carcinoma associated antibodies including those expressed by colorectal, pancreatic and ovarian carcinomas. In a preferred embodiment, antibodies against CEA, MUC1, MUC 2, MUC3, MUC 4, PAM-4, KC4, BrE3, Le-Y (e.g., B3 antibody), EGFR, EGP-1, RS5 (GA733 antigen target, such as for antibodies to EGP-2, 17-1A, KS1-4, Ep-CAM), TAG-72, the A33 antibody-determinant, KS-1, A3 and HER2/neu are used for combination therapy with humanized, chimeric or human anti-CSAp antibodies. See, e.g., Mendez et al., *Nature Genetics*, 15: 146-156 (1997); U.S. Pat. No. 5,633,425, which are incorporated in their entirety by reference. The BrE3 antibody is described in Couto, J, Christian, R, Peterson, J, and Ceriani, R., *Cancer Res.* 1995; 55 (Suppl.23):5973s-5977s. The EGP-1 antibody is described in U.S. Provisional Application No. 60/360,229, some of the EGP-2 antibodies are cited in Birbenet et al., in Staib et al.; and Schwartzberg in the references cited at the end of this application. The KS-1 antibody is cited in Koda et al.; the A33 antibody is cited in Ritter et al. at end; Le(y) antibody B3 described in Di Carlo et al; A3 antibody is described in Tordsson et al., all listed in the references cited at the end of this application. Preferably, antibodies against marker antigens or receptors of gastrointestinal and ovarian carcinomas are well suited for use in combination with CSAp antibodies, and in particular with the Mu-9 antibodies. In a preferred embodiment, a gastrointestinal cancer is a colorectal cancer.

Also of use are antibodies against markers or products of oncogenes, or antibodies against angiogenesis factors, such as VEGF. VEGF antibodies are described in Thorpe et al., U.S. Pat. Nos. 6,342,221, 5,965,132 and 6,004,554, and are incorporated by reference in their entirety. Antibodies against certain immune response modulators, such as antibodies to CD40, are described in Todryk et al. and Turner et al., listed in the references cited at the end of this application. Other antibodies suitable for combination therapy include anti-necrosis antibodies as described in Epstein et al. (infra).

Cell lines and culture media used in the present invention include Mu-9 hybridoma cells and Sp2/0-Ag14 myeloma cells (ATCC, Rockville, Md.). The monoclonal hybridoma producing Mu-9 was obtained by fusing the spleen from a mouse that had been immunized with colon-specific antigen-p (CSAp) with SP2/0Ag14. These cells may be cultured in Hybridoma serum-free media (HSFM) (life Technologies, Grand Island, N.Y.) supplemented with 10% fetal bovine serum (FBS) (Hyclone Laboratories, Logan, Utah) and antibiotics (complete media). Alternatively, they may be cultured in Dulbecco's modified Eagle's Medium (DMEM) supplemented with 10% FCS (Gibco/BRL, Gaithersburg, Mass.) containing 10% of FCS and 75 µg/ml gantamicin (complete HSFM) or, where indicated, in HSFM containing only antibiotics. Selection of the transfectomas may be carried out in complete HSFM containing 500 units/ml of hygromycin (Calbiochem, San Diego, Calif.). All cell lines are preferably maintained at 37° C. in 5% $CO_2$.

Obtaining Vκ and $V_H$ Gene Segments

Isolation of the Vκ and $V_H$ gene segments can be accomplished by several means that are well-known in the art. Two such means include, but are not limited to, PCR cloning and cDNA library screening.

PCR cloning techniques are well-known in the art. In brief, however, PCR cloning of Vκ and $V_H$ gene fragments may be accomplished as follows. Poly A mRNA may be isolated from a Mu-9 hybridoma cell line using commercially available kits such as the Fast Track mRNA Isolation kit (Invitrogen, San Diego, Calif.). The first strand cDNA may then be reverse transcribed from poly A mRNA using a cDNA cycle kit (Invitrogen). In this process, poly A mRNA is annealed to a murine IgG CH1-specific primer or a murine Ck-specific primer. Examples of such primers include CH1B (5'-ACA GTC ACT GAG CTG G-3') and Ck3-BH1 (5'-GCC GGA TCC TGA CTG GAT GGT GGG AAG ATG GAT ACA-3'), respectively. The first strand cDNA may be used as templates to amplify the $V_H$ and Vκ sequences by PCR, as described by Orlandi et al. For the Vκ region, a primer pair such as VK1Back (5'-GAC ATT CAG CTG ACC CAG TCT CCA-3') and IgGKC3' (5'-CTC ACT GGA TGG TGG GAA GAT GGA TAC AGT TGG-3') may be used. For the $V_H$ region, a primer pair such as VH1Back (5'-AGG T(C/G)(A/C) A(A/G)C TGC AG(C/G) AGT C(A/T)G G-3') and CH1B may be used. After amplification, the Vκ and $V_H$ fragments may then be gel-purified and cloned into a cloning vector such as the TA cloning vector (Invitrogen) for sequence analyses by the dideoxytermination method. Sequences confirmed to be of immunoglobulin origin may then be used to construct chimeric expression vectors using methods described by Leung et al.

As a preferred alternative to isolating the Vκ and $V_H$ gene segments by PCR cloning, cDNA library screening may be utilized. cDNA screening methods also are well known in the art. In brief, however, a cDNA library may be constructed from the mRNA extracted from the murine Mu-9 hybridoma cells in pSPORT vector (Life Technologies). The first strand cDNA may be synthesized by priming ply A RNA from Mu-9 hybridoma with an oligo dT primer-NotI adaptor (Life Technologies). After the second strand synthesis and attachment of SalI adaptors, the cDNA pool may be size fractionated through a cDNA size fractionation column. Fractionated cDNA may then be ligated to pSPORT vector and subsequently transformed into *Escherichia coli* DH5α. A library may then be plated, transferred to filters, and amplified.

Screening of the cDNA library may be accomplished by hybridization with labeled probes specific for the heavy and light chains. For example [32-P]-labeled probes such as MUCH-1 (5'-AGA CTG CAG GAG AGC TGG GAA GGT GTG CAC-3') for heavy chain and MUCK-1 (5'-GAA GCA CAC GAC TGA GGC ACC TCC AGA TGT-3') for light chain. Clones that are positive on a first screening may be transferred to duplicate plates and screened a second time with the same probes.

RNA isolation, cDNA synthesis, and amplification can be carried out as follows. Total cell RNA can be prepared from a Mu-9 hybridoma cell line, using a total of about $10^7$ cells, according to Sambrook et al., (Molecular Cloning: A Laboratory Manual, Second ed., Cold Spring Harbor Press, 1989), which is incorporated by reference. First strand cDNA can be reverse transcribed from total RNA conventionally, such as by using the SuperScript preamplification system (Gibco/BRL, Gaithersburg, Md.). Briefly, in a reaction volume of 20 μl, 50 ng of random hexamer primers can be annealed to 5 μg of RNAs in the presence of 2 μl of 10× synthesis buffer [200 mM Tris-HCl (pH 8.4), 500 mM KCl, 25 mM $MgCl_2$, 1 mg/ml BSA], 1 μl of 10 mM dNTP mix, 2 μl of 0.1 M DTT, and 200 units of SuperScript reverse transcriptase. The elongation step is initially allowed to proceed at room temperature for 10 min followed by incubation at 42° C. for 50 min. The reaction can be terminated by heating the reaction mixture at 90° C. for 5 min.

Synthesizing and labeling the screening probes can be accomplished by well-known means. Depending on the detection systems utilized, probe labeling will vary. Many kits for this purpose are commercially available. One method for 32-P labeling of oligonucleotides includes the use of with [$\gamma$-$^{32}$P]ATP (Amersham Arlington Heights, Ill.) and T4 polynucleotide kinase (New England Biolabs, Beverly, Mass.), followed by column purification.

Preparation of a Chimeric Anti-CSAp Antibody

In general, to prepare chimeric anti-CSAp MAb, $V_H$ and V κchains of a CSAp antibody may be obtained by methods such as those described above and amplified by PCR. In a preferred embodiment, the chimeric anti-CSAp antibody is a Mu-9 antibody. The Vκ PCR products may be subcloned into a pBR327 based staging vector (VKpBR) as described by leung et al., Hybridoma, 13:469 (1994). The $V_H$ PCR products may be subcloned into a similar pBluescript-based staging vector (VHpBS). The fragments containing the Vκ and $V_H$ sequences, along with the promoter and signal peptide sequences, can be excised from the staging vectors using HindIII and BamHI restriction endonucleases. The Vκ fragments (about 600 bp) can be subcloned into a mammalian expression vector (for example, pKh) conventionally. pKh is a pSVhyg-based expression vector containing the genomic sequence of the human kappa constant region, an Ig enhancer, a kappa enhancer and the hygromycin-resistant gene. Similarly, the about 800 bp $V_H$ fragments can be subcloned into pG1g, a pSVgpt-based expression vector carrying the genomic sequence of the human IgG1 constant region, an Ig enhancer and the xanthine-guanine phosphoribosyl transferase (gpt) gene. The two plasmids may be co-transfected into mammalian cells, such as Sp2/0-Ag14 cells, by electroporation and selected for hygromycin resistance. Colonies surviving selection are expanded, and supernatant fluids monitored for production of cMu-9 mAb by an ELISA method. A transfection efficiency of about 1-10×$10^6$ cells is desirable. An antibody expression level of between 0.10 and 2.5 μg/ml can be expected with this system.

Alternately, the Vκ and $V_H$ expression cassettes can be assembled in the modified staging vectors, VKpBR2 and VHpBS2, excised as XbaI/BamHI and XhoI/BamHI fragments, respectively, and subcloned into a single expression vector, such as pdHL2, as described by Gilles et al. *J. Immunol. Methods* 125:191 (1989), Losman et al., *Clin. Cancer Res.* 5:3101 (1999) and in Losman et al., *Cancer*, 80:2660 (1997) for the expression in Sp2/0-Ag14 cells. Another vector that is useful in the present invention is the GS vector, as described in Barnes et al., *Cytotechnology* 32:109-123 (2000), which is preferably expressed in the NS0 cell line and CHO cells. Other appropriate mammalian expression systems are described in Werner et al., Arzneim.-Forsch./Drug Res. 48(II), Nr. 8, 870-880 (1998

The Vκ and $V_H$ sequences can be amplified by PCR as described by Orlandi et al., (Proc. Natl. Acad. Sci., U.S.A., 86: 3833 (1989)) which is incorporated by reference. Vk sequences may be amplified using the primers CK3BH and Vκ5-3 (Leung et al., BioTechniques, 15: 286 (1993), which is incorporated by reference), while $V_H$ sequences can be amplified using the primer CH1B which anneals to the CH1 region of murine IgG, and VHIBACK (Orlandi et al., 1989 above). The PCR reaction mixtures containing 10 µl of the first strand cDNA product, 9 µl of 10×PCR buffer [500 mM KCl, 100 mM Tris-HCl (pH 8.3), 15 mM $MgCl_2$, and 0.01% (w/v) gelatin] (Perkin Elmer Cetus, Norwalk, Conn.), can be subjected to 30 cycles of PCR. Each PCR cycle preferably consists of denaturation at 94° C. for 1 min, annealing at 50° C. for 1.5 min, and polymerization at 72° C. for 1.5 min. Amplified Vk and VH fragments can be purified on 2% agarose (BioRad, Richmond, Calif.).

Preparation of a Humanized Anti-CSAp Antibody

In a preferred embodiment, the humanized anti-CSAp antibody is a humanized Mu-9 antibody. Once the sequences for the hMu-9Vκ and $V_H$ domains are designed, CDR engrafting can be accomplished by gene synthesis using long synthetic DNA oligonucleotides as templates and short oligonucleotides as primers in a PCR reaction. In most cases, the DNA encoding the Vκ or VH domain will be approximately 350 bp long. By taking advantage of codon degeneracy, a unique restriction site may easily be introduced, without changing the encoded amino acids, at regions close to the middle of the V gene DNA sequence. For example, at DNA nucleotide positions 132-137 (amino acid positions 44-46) for the hMu-9 VH domain, a unique XbaI site can be introduced while maintaining the originally designed amino acid sequence (see the sequence in FIG. 4A). Two long non-overlapping single-stranded DNA oligonucleotides (~150 bp) upstream and downstream of the XbaI site can be generated by automated DNA oligonucleotide synthesizer (Cyclone Plus DNA Synthesizer, Milligen-Biosearch). As the yields of full length DNA oligonucleotides may be expected to be low, they can be amplified by two pairs of flanking oligonucleotides in a PCR reaction. The primers can be designed with the necessary restriction sites to facilitate subsequent sequence assembly and subcloning. Primers for the oligonucleotides should contain overlapping sequence at the XbaI site so that the resultant PCR products can be joined in-frame at the XbaI site to form a full length DNA sequence encoding the hMu-9 $V_H$ domain. The ligation of the PCR products for the oligos at the XbaI site and their subcloning into the PstII/ BstEII sites of the staging vector, VHpBS, can be completed in a single three-fragment ligation step. The subcloning of the correct sequence into VHpBS can be first analyzed by restriction digestion analysis and subsequently conformed by sequencing reaction according to Sanger et al., Proc. Natl. Acad. Sci. USA 74 5463 (1977).

The HindIII/BamHI fragment containing the Ig promoter, leader sequence and the hMu-9 $V_H$ sequence can be excised from the staging vector and subcloned to the corresponding sites in a pSVgpt-based vector, pG1 g, which contains the genomic sequence of the human IgG constant region, an Ig enhancer and a gpt selection marker, forming the final expression vector, hMu-9pG1g. Similar strategies can be employed for the construction of the hMu-9 Vκ sequence. The restriction site chosen for the ligation of the PCR products for the long oligonucleotides can be NruI in this case.

The DNA sequence containing the Ig promoter, leader sequence and the hMu-9 Vκ sequence can be excised from the staging vector VKpBR by treatment with BamHI/HindIII, and can be subcloned into the corresponding sites of a pSVhyg-based vector, pKh, which contains the genomic sequence of human kappa chain constant regions, a hygromycin selection marker, an Ig and a kappa enhancer, forming the final expression vector, hMu-9pKh.

The two plasmids can be co-transfected into an appropriate cell, e.g., myeloma Sp2/0-Ag14, colonies selected for hygromycin resistance, and supernatant fluids monitored for production of hMu-9 antibodies by, for example, an ELISA assay, as described below. Alternately, the Vκ and VH expression cassettes can be assembled in the modified staging vectors, VKpBR2 and VHpBS2, excised as XbaI/BamHI and XhoI/BamHI fragments, respectively, and subcloned into a single expression vector, such as pdHL2, as described by Gilles et al., J. Immunol. Methods 125:191 (1989), Losman et al., Clin. Cancer Res. 5:3101 (1999) and in Losman et al., Cancer, 80:2660 (1997) for the expression in Sp2/0-Ag14 cells. Another vector that is useful in the present invention is the GS vector, as described in Barnes et al., Cytotechnology 32:109-123 (2000), which is preferably expressed in the NS0 cell line and CHO cells. Other appropriate mammalian expression systems are described in Werner et al., Arzneim.-Forsch./Drug Res. 48(II), Nr. 8, 870-880 (1998).

Transfection, and assay for antibody secreting clones by ELISA, can be carried out as follows. About 10 µg of hMu-9pKh (light chain expression vector) and 20 µg of hMu-9pG1g (heavy chain expression vector) can be used for the transfection of $5×10^6$ SP2/0 myeloma cells by electroporation (BioRad, Richmond, Calif.) according to Co et al., J. Immunol., 148: 1149 (1992) which is incorporated by reference. Following transfection, cells may be grown in 96-well microtiter plates in complete HSFM medium (GIBCO, Gaithersburg, Md.) at 37° C., 5% $CO_2$. The selection process can be initiated after two days by the addition of hygromycin selection medium (Calbiochem, San Diego, Calif.) at a final concentration of 500 µg/ml of hygromycin. Colonies typically emerge 2-3 weeks post-electroporation. The cultures can then be expanded for further analysis.

Screening the Clones and Isolating Antibodies

Transfectoma clones that are positive for the secretion of chimeric or humanized heavy chain can be identified by ELISA assay. Briefly, supernatant samples (100 µl) from transfectoma cultures are added in triplicate to ELISA microtiter plates precoated with goat anti-human (GAH)-IgG, F(ab')$_2$ fragment-specific antibody (Jackson ImmunoResearch, West Grove, Pa.). Plates are incubated for 1 h at room temperature. Unbound proteins are removed by washing three times with wash buffer (PBS containing 0.05% polysorbate 20). Horseradish peroxidase (HRP) conjugated GAH-IgG, Fc fragment-specific antibodies (Jackson ImmunoResearch, West Grove, Pa.) are added to the wells, (100 µl of antibody stock diluted ×$10^4$, supplemented with the unconjugated antibody to a final concentration of 1.0 µg/ml). Following an incubation of 1 h, the plates are washed, typically three times. A reaction solution, [100 µl, containing 167 µg of orthophenylene-diamine (OPD) (Sigma, St. Louis, Mo.), 0.025% hydrogen peroxide in PBS], is added to the wells. Color is allowed to develop in the dark for 30 minutes. The reaction is stopped by the addition of 50 µl of 4 N HCl solution into each well before measuring absorbance at 490 nm in an automated ELISA reader (Bio-Tek instruments, Winooski, Vt.). Bound chimeric antibodies are than determined relative to an irrelevant chimeric antibody standard (obtainable from Scotgen, Ltd., Edinburg, Scotland).

Antibodies can be isolated from cell culture media as follows. Transfectoma cultures are adapted to serum-free medium. For production of chimeric antibody, cells are grown as a 500 ml culture in roller bottles using HSFM. Cultures are centrifuged and the supernatant filtered through a 0.2 micron membrane. The filtered medium is passed through a protein A column (1×3 cm) at a flow rate of 1 ml/min. The resin is then washed with about 10 column volumes of PBS and protein A-bound antibody is eluted from the column with 0.1 M glycine buffer (pH 3.5) containing 10 mM EDTA. Fractions of 1.0 ml are collected in tubes containing 10 μl of 3 M Tris (pH 8.6), and protein concentrations determined from the absorbancies at 280/260 nm. Peak fractions are pooled, dialyzed against PBS, and the antibody concentrated, for example, with the Centricon 30 (Amicon, Beverly, Mass.). The antibody concentration is determined by ELISA, as before, and its concentration adjusted to about 1 mg/ml using PBS. Sodium azide, 0.01% (w/v), is conveniently added to the sample as preservative.

The affinity of a chimeric, humanized or human anti-CSAp antibody may be evaluated using a direct binding assay or a competitive binding assay, as exemplified below.

Modifying/Optimizing the Recombinant Antibodies

As humanization sometimes results in a reduction or even loss of antibody affinity, additional modification might be required in order to restore the original affinity (See, for example, Tempest et al., Bio/Technology 9: 266 (1991); Verhoeyen et al., Science 239: 1534 (1988)), which are incorporated by reference. Knowing that cMu-9 exhibits a binding affinity comparable to that of its murine counterpart, defective designs, if any, in the original version of hMu-9 can be identified by mixing and matching the light and heavy chains of cMu-9 to those of the humanized version. Preferably, some human residues in the framework regions are replaced by their murine counterparts. Also preferred, a combination of framework sequences from 2 different human antibodies, such as EU and NEWM are used for $V_H$. For example, FR1-3 can come from EU and FR 4 from NEWM.

Other modifications, such as Asn-linked glycosylation sites, can be introduced into a chimerized, human, or humanized Mu-9 antibody by conventional oligonucleotide directed site-specific mutagenesis. Detailed protocols for oligonucleotide-directed mutagenesis and related techniques for mutagenesis of cloned DNA are well known. For example, see Sambrook et al. and Ausubel et al. above.

For example, to introduce an Asn in position 18 of hMu-9 Vκ (FIG. 4B), one may alter codon 18 from CGA for Arg to AAC. To accomplish this, a single stranded DNA template containing the antibody light chain sequence is prepared from a suitable strain of E. coli (e.g., dut$^-$, ung$^-$) in order to obtain a single strand DNA molecule containing a small number of uracils in place of thymidine. Such a DNA template can be obtained by M13 cloning or by in vitro transcription using a SP6 promoter. See, for example, Ausubel et al., eds., CURRENT PROTOCOLS IN MOLECULAR BIOLOGY, John Wiley & Sons, NY, 1987. An oligonucleotide containing the mutated sequence is synthesized conventionally, annealed to the single-stranded template and the product treated with T4 DNA polymerase and T4 DNA ligase to produce a double-stranded DNA molecule. Transformation of wild type E. (dut$^+$, ung$^+$) cells with the double-stranded DNA provides an efficient recovery of mutated DNA.

Alternatively, an Asn-linked glycosylation site can be introduced into an antibody light chain using an oligonucleotide containing the desired mutation as the primer and DNA clones of the variable regions for the Vk chain, or by using RNA from cells that produce the antibody of interest as a template. Also see, Huse, in ANTIBODY ENGINEERING: A PRACTICAL GUIDE, Boerrebaeck, ed., W. H. Freeman & Co., pp. 103-120, 1992. Site-directed mutagenesis can be performed, for example, using the TRANSFORMER™ kit (Clonetech, Palo Alto, Calif.) according to the manufacturer's instructions.

Alternatively, a glycosylation site can be introduced by synthesizing an antibody chain with mutually priming oligonucleotides, one such containing the desired mutation. See, for example, Uhlmann, Gene 71: 29 (1988); Wosnick et al., Gene 60: 115 (1988); Ausubel et al., above, which are incorporated by reference.

Although the general description above referred to the introduction of an Asn glycosylation site in position 18 of the light chain of an antibody, it will occur to the skilled artisan that it is possible to introduce Asn-linked glycosylation sites elsewhere in the light chain, or even in the heavy chain variable region.

Determining Antibody Binding Affinity

Comparative binding affinities of the isolated murine, human, humanized and chimeric Mu-9 antibodies thus isolated may be determined by direct radioimmunoassay. Mu-9 can be labeled with $^{131}$I or $^{125}$I using the chloramine T method (see, for example, Greenwood et al., Biochem. J., 89: 123 (1963) which is incorporated by reference). The specific activity of the iodinated antibody is typically adjusted to about 10 μCi/μg. Unlabeled and labeled antibodies are diluted to the appropriate concentrations using reaction medium (HSFM supplemented with 1% horse serum and 100 μg/ml gentamicin). The appropriate concentrations of both labeled and unlabeled antibodies are added together to the reaction tubes in a total volume of 100 μl. A culture of GW-39 tumor cells is sampled and the cell concentration determined. The culture is centrifuged and the collected cells washed once in reaction medium followed by resuspension in reaction medium to a final concentration of about $10^7$ cells/ml. All procedures are carried out in the cold at 4° C. The cell suspension, 100 μl, is added to the reaction tubes. The reaction is carried out at 4° C. for 2 h with periodic gentle shaking of the reaction tubes to resuspend the cells. Following the reaction period, 5 ml of wash buffer (PBS containing 1% BSA) is added to each tube. The suspension is centrifuged and the cell pellet washed a second time with another 5 ml of wash buffer. Following centrifugation, the amount of remaining radioactivity remaining in the cell pellet is determined in a gamma counter (Minaxi, Packard Instruments, Sterling, Va.).

III. Production of Antibody Fragments

Antibody fragments which recognize specific epitopes can be generated by known techniques. The antibody fragments are antigen binding portions of an antibody, such as F(ab')$_2$, Fab', Fab, Fv, sFv and the like. Other antibody fragments include, but are not limited to: the F(ab)'$_2$ fragments which can be produced by pepsin digestion of the antibody molecule and the Fab' fragments, which can be generated by reducing disulfide bridges of the F(ab')$_2$ fragments. Alternatively, Fab' expression libraries can be constructed (Huse et al., 1989, Science, 246:1274-1281) to allow rapid and easy identification of monoclonal Fab' fragments with the desired specificity. The present invention encompasses antibodies and antibody fragments.

A single chain Fv molecule (scFv) comprises a VL domain and a VH domain. The VL and VH domains associate to form a target binding site. These two domains are further covalently linked by a peptide linker (L). A scFv molecule is denoted as either VL-L-VH if the VL domain is the N-terminal part of the scFv molecule, or as VH-L-VL if the VH domain is the N-terminal part of the scFv molecule. Methods for making scFv molecules and designing suitable peptide linkers are described in U.S. Pat. Nos. 4,704,692, 4,946,778, R. Raag and M. Whitlow, "*Single Chain Fvs*." FASEB Vol 9:73-80 (1995) and R. E. Bird and B. W. Walker, "*Single Chain Antibody Variable Regions*," TIBTECH, Vol 9:132-137 (1991). These references are incorporated herein by reference.

To obtain high-affinity scFv, an scFv library with a large repertoire can be constructed by isolating V-genes from non-immunized human donors using PCR primers corresponding to all known $V_H$, $V_\kappa$ and $V_\lambda$ gene families. See, e.g., Vaughn et al., *Nat. Biotechnol.*, 14: 309-314 (1996). Following amplification, the $V_\kappa$ and $V_\lambda$ pools are combined to form one pool. These fragments are ligated into a phagemid vector. The scFv linker, (Gly-Gly-Gly-Gly-Ser)$_3$, is then ligated into the phagemid upstream of the $V_L$ fragment. The $V_H$ and linker-$V_L$ fragments are amplified and assembled on the $J_H$ region. The resulting $V_H$-linker-$V_L$ fragments are ligated into a phagemid vector. The phagemid library can be panned using filters, as described above, or using immunotubes (Nunc; Maxisorp). Similar results can be achieved by constructing a combinatorial immunoglobulin library from lymphocytes or spleen cells of immunized rabbits and by expressing the scFv constructs in *P. pastoris*. See, e.g., Ridder et al., *Biotechnology*, 13: 255-260 (1995). Additionally, following isolation of an appropriate scFv, antibody fragments with higher binding affinities and slower dissociation rates can be obtained through affinity maturation processes such as CDR3 mutagenesis and chain shuffling. See, e.g., Jackson et al., *Br. J. Cancer*, 78: 181-188 (1998); Osbourn et al., *Immunotechnology*, 2: 181-196 (1996).

An antibody fragment can be prepared by proteolytic hydrolysis of the full length antibody or by expression in *E. coli* or another host of the DNA coding for the fragment. An antibody fragment can be obtained by pepsin or papain digestion of full-length antibodies by conventional methods. For example, an antibody fragment can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using papain produces two monovalent Fab fragments and an Fc fragment directly. These methods are described, for example, by Goldenberg, U.S. Pat. Nos. 4,036,945 and 4,331,647 and references contained therein, which patents are incorporated herein in their entireties by reference. Also, see Nisonoff et al., *Arch Biochem. Biophys.* 89: 230 (1960); Porter, *Biochem. J.* 73: 119 (1959), Edelman et al., in METHODS IN ENZYMOLOGY VOL. 1, page 422 (Academic Press 1967), and Coligan at pages 2.8.1-2.8.10 and 2.10.-2.10.4.

Another form of an antibody fragment is a peptide coding for a single complementarity-determining region (CDR). A CDR is a segment of the variable region of an antibody that is complementary in structure to the epitope to which the antibody binds and is more variable than the rest of the variable region. Accordingly, a CDR is sometimes referred to as hypervariable region. A variable region comprises three CDRs. CDR peptides can be obtained by constructing genes encoding the CDR of an antibody of interest. Such genes are prepared, for example, by using the polymerase chain reaction to synthesize the variable region from RNA of antibody-producing cells. See, for example, Larrick et al., *Methods: A Companion to Methods in Enzymology* 2: 106 (1991); Courtenay-Luck, "Genetic Manipulation of Monoclonal Antibodies," in MONOCLONAL ANTIBODIES: PRODUCTION, ENGINEERING AND CLINICAL APPLICATION, Ritter et al. (eds.), pages 166-179 (Cambridge University Press 1995); and Ward et al., "Genetic Manipulation and Expression of Antibodies," in MONOCLONAL ANTIBODIES: PRINCIPLES AND APPLICATIONS, Birch et al., (eds.), pages 137-185 (Wiley-Liss, Inc. 1995).

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

Preparation of a Bispecific Antibody

The bsAbs can be prepared by techniques known in the art, for example, anti-CSAp Ab and an anti-peptide Ab are both separately digested with pepsin to their respective F(ab')$_2$s abd reduced with cystein to Fab' monomeric units. The Fab' of anti-CSAp antibody is reacted with the cross-linker bis(maleimido) hexane to produce Fab'-maleimide moieties. The anti-peptide Ab-Fab'-SH is purified and reacted with the anti-CSAp Fab'-maleimide to generate the Fab'×Fab' bi-specific Ab. Alternatively, the anti-peptide Fab'-SH fragment may be coupled with the anti-CSAp F(ab')$_2$ to generate a F(ab')$_2$×Fab' construct, or with anti-CSAp IgG to generate an IgG×Fab' bi-specific construct. In one embodiment, the IgG×Fab' construct can be prepared in a site-specific manner by attaching the antipeptide Fab' thiol group to anti-CSAp IgG heavy-chain carbohydrate which has been periodate-oxidized, and subsequently activated by reaction with a commercially available hydrazide-maleimide cross-linker. The component Abs used can be chimerized or humanized by known techniques. A chimeric antibody is a recombinant protein that contains the variable domains and complementary determining regions derived from a rodent antibody, while the remainder of the antibody molecule is derived from a human antibody. Humanized antibodies are recombinant proteins in which murine complementarity determining regions of a monoclonal antibody have been transferred from heavy and light variable chains of the murine immunoglobulin into a human variable domain.

A variety of recombinant methods can be used to produce bi-specific antibodies and antibody fragments. For example, bi-specific antibodies and antibody fragments can be produced in the milk of transgenic livestock. See, e.g., Colman, A., *Biochem. Soc. Symp.*, 63: 141-147, 1998; U.S. Pat. No. 5,827,690. Two DNA constructs are prepared which contain, respectively, DNA segments encoding paired immunoglobulin heavy and light chains. The fragments are cloned into expression vectors which contain a promoter sequence that is preferentially expressed in mammary epithelial cells. Examples include, but are not limited to, promoters from rabbit, cow and sheep casein genes, the cow α-lactoglobulin gene, the sheep β-lactoglobulin gene and the mouse whey acid protein gene. Preferably, the inserted fragment is flanked on its 3' side by cognate genomic sequences from a mammary-specific gene. This provides a polyadenylation site and transcript-stabilizing sequences. The expression cassettes are coinjected into the pronuclei of fertilized, mammalian eggs, which are then implanted into the uterus of a recipient female and allowed to gestate. After birth, the progeny are screened for the presence of both transgenes by Southern analysis. In order for the antibody to be present, both heavy and light chain genes must be expressed concurrently in the same cell. Milk from transgenic females is analyzed for the presence and functionality of the antibody or antibody fragment using standard immunological methods known in the art. The antibody can be purified from the milk using standard methods known in the art.

A chimeric Ab is constructed by ligating the cDNA fragment encoding the mouse light variable and heavy variable domains to fragment encoding the C domains from a human antibody. Because the C domains do not contribute to antigen binding, the chimeric antibody will retain the same antigen specificity as the original mouse Ab but will be closer to human antibodies in sequence. Chimeric Abs still contain some mouse sequences, however, and may still be immunogenic. A humanized Ab contains only those mouse amino acids necessary to recognize the antigen. This product is constructed by building into a human antibody framework the amino acids from mouse complementarity determining regions.

Other recent methods for producing bsAbs include engineered recombinant Abs which have additional cysteine residues so that they crosslink more strongly than the more common immunoglobulin isotypes. See, e.g., FitzGerald et al., Protein Eng. 10(10):1221-1225, 1997. Another approach is to engineer recombinant fusion proteins linking two or more different single-chain antibody or antibody fragment segments with the needed dual specificities. See, e.g., Coloma et al., Nature Biotech. 15:159-163, 1997. A variety of bi-specific fusion proteins can be produced using molecular engineering. In one form, the bi-specific fusion protein is monovalent, consisting of, for example, a scFv with a single binding site for one antigen and a Fab fragment with a single binding site for a second antigen. In another form, the bi-specific fusion protein is divalent, consisting of, for example, an IgG with two binding sites for one antigen and two scFv with two binding sites for a second antigen.

Functional bi-specific single-chain antibodies (bscAb), also called diabodies, can be produced in mammalian cells using recombinant methods. See, e.g., Mack et al., Proc. Natl. Acad. Sci., 92: 7021-7025, 1995. For example, bscAb are produced by joining two single-chain Fv fragments via a glycine-serine linker using recombinant methods. The V light-chain ($V_L$) and V heavy-chain ($V_H$) domains of two antibodies of interest are isolated using standard PCR methods. The $V_L$ and $V_H$ cDNA's obtained from each hybridoma are then joined to form a single-chain fragment in a two-step fusion PCR. The first PCR step introduces the $(Gly_4-Ser_1)_3$ linker, and the second step joins the $V_L$ and $V_H$ amplicons. Each single chain molecule is then cloned into a bacterial expression vector. Following amplification, one of the single-chain molecules is excised and sub-cloned into the other vector, containing the second single-chain molecule of interest. The resulting bscAb fragment is subcloned into an eukaryotic expression vector. Functional protein expression can be obtained by transfecting the vector into chinese hamster ovary cells. Bi-specific fusion proteins are prepared in a similar manner. Bi-specific single-chain antibodies and bi-specific fusion proteins are included within the scope of the present invention. Diabody, triabody and tetrabody bispecific fusion proteins produced in E. coli and yeast are described in U.S. Provisional Application Nos. 60/345,641, 60/328,835 and 60/342,103, and are incorporated herein by reference.

Bi-specific fusion proteins linking two or more different single-chain antibodies or antibody fragments are produced in similar manner.

Large quantities of bscAb and fusion proteins can be produced using Escherichia coli expression systems. See, e.g., Zhenping et al., Biotechnology, 14: 192-196, 1996. A functional bscAb can be produced by the coexpression in E. coli of two "cross-over" scFv fragments in which the $V_L$ and $V_H$ domains for the two fragments are present on different polypeptide chains. The V light-chain ($V_L$) and V heavy-chain ($V_H$) domains of two antibodies of interest are isolated using standard PCR methods. The cDNA's are then ligated into a bacterial expression vector such that C-terminus of the $V_L$ domain of the first antibody of interest is ligated via a linker to the N-terminus of the $V_H$ domain of the second antibody. Similarly, the C-terminus of the $V_L$ domain of the second antibody of interest is ligated via a linker to the N-terminus of the $V_H$ domain of the first antibody. The resulting dicistronic operon is placed under transcriptional control of a strong promoter, e.g., the E. coli alkaline phosphatase promoter which is inducible by phosphate starvation. Alternatively, single-chain fusion constructs have successfully been expressed in E. coli using the lac promoter and a medium consisting of 2% glycine and 1% Triton X-100. See, e.g., Yang et al., Appl. Environ. Microbiol., 64:2869-2874, 1998. An E. coli, heat-stable, enterotoxin II signal sequence is used to direct the peptides to the periplasmic space. After secretion, the two peptide chains associate to form a non-covalent heterodimer which possesses both antigen binding specificities. The bscAb is purified using standard procedures known in the art, e.g., Staphylococcal protein A chromatography.

Functional bscAb and fusion proteins also can be produced in the milk of transgenic livestock. See, e.g., Colman, A., Biochem. Soc. Symp., 63: 141-147, 1998; U.S. Pat. No. 5,827, 690. The bscAb fragment, obtained as described above, is cloned into an expression vector containing a promoter sequence that is preferentially expressed in mammary epithelial cells. Examples include, but are not limited to, promoters from rabbit, cow and sheep casein genes, the cow α-lactoglobulin gene, the sheep β-lactoglobulin gene and the mouse whey acid protein gene. Preferably, the inserted bscAb is flanked on its 3' side by cognate genomic sequences from a mammary-specific gene. This provides a polyadenylation site and transcript-stabilizing sequences. The expression cassette is then injected into the pronuclei of fertilized, mammalian eggs, which are then implanted into the uterus of a recipient female and allowed to gestate. After birth, the progeny are screened for the presence of the introduced DNA by Southern analysis. Milk from transgenic females is analyzed for the presence and functionality of the bscAb using standard immunological methods known in the art. The bscAb can be purified from the milk using standard methods known in the art. Transgenic production of bscAb in milk provides an efficient method for obtaining large quantities of bscAb.

Functional bscAb and fusion proteins also can be produced in transgenic plants. See, e.g., Fiedler et al., Biotech., 13: 1090-1093, 1995; Fiedler et al., Immunotechnology, 3: 205-216, 1997. Such production offers several advantages including low cost, large scale output and stable, long term storage. The bscAb fragment, obtained as described above, is cloned into an expression vector containing a promoter sequence and encoding a signal peptide sequence, to direct the protein to the endoplasmic recticulum. A variety of promoters can be utilized, allowing the practitioner to direct the expression product to particular locations within the plant. For example, ubiquitous expression in tobacco plants can be achieved by using the strong cauliflower mosaic virus 35S promoter, while organ specific expression is achieved via the seed specific legumin B4 promoter. The expression cassette is transformed according to standard methods known in the art. Transformation is verified by Southern analysis. Transgenic plants are analyzed for the presence and functionality of the bscAb using standard immunological methods known in the art. The bscAb can be purified from the plant tissues using standard methods known in the art.

Additionally, transgenic plants facilitate long term storage of bscAb and fusion proteins. Functionally active scFv proteins have been extracted from tobacco leaves after a week of storage at room temperature. Similarly, transgenic tobacco seeds stored for 1 year at room temperature show no loss of scFv protein or its antigen binding activity.

Functional bscAb and fusion proteins also can be produced in insect cells. See, e.g., Mahiouz et al., *J. Immunol. Methods,* 212: 149-160 (1998). Insect-based expression systems provide a means of producing large quantities of homogenous and properly folded bscAb. The baculovirus is a widely used expression vector for insect cells and has been successfully applied to recombinant antibody molecules. See, e.g., Miller, L. K., *Ann. Rev. Microbiol.,* 42: 177 (1988); Bei et al., *J. Immunol. Methods,* 186: 245 (1995). Alternatively, an inducible expression system can be utilized by generating a stable insect cell line containing the bscAb construct under the transcriptional control of an inducible promoter. See, e.g., Mahiouz et al., *J. Immunol. Methods,* 212: 149-160 (1998). The bscAb fragment, obtained as described above, is cloned into an expression vector containing the *Drosphila* metallothionein promoter and the human HLA-A2 leader sequence. The construct is then transfected into *D. melanogaster* SC-2 cells. Expression is induced by exposing the cells to elevated amounts of copper, zinc or cadmium. The presence and functionality of the bscAb is determined using standard immunological methods known in the art. Purified bscAb is obtained using standard methods known in the art.

Preferred bispecific antibodies of the instant invention are those which incorporate the Fv of MAb Mu-9 and the Fv of MAb 679 and their human, chimerized or humanized counterparts. Accordingly, an anti-CSAp antibody fragments are also contemplated in the present invention. Preferably, the anti-CSAp antibody fragment is a Mu-9 antibody fragment. Also preferred are bispecific antibodies which incorporate one or more of the CDRs of Mu-9.

IV. Antibodies for Treatment and Diagnosis/Detection

Humanized, Chimeric and Human Anti-CSAp Antibodies for Treatment and Diagnosis/Detection.

Contemplated in the present invention is the use of humanized, chimeric and human anti-CSAp antibodies and fragments thereof in therapeutic and diagnostic/detection methods. Preferably, the chimeric, humanized and human anti-CSAp antibodies and fragments thereof are chimeric, humanized or human Mu-9 antibodies. Still preferred, the chimeric, humanized and human Mu-9 antibodies and fragments thereof of the present invention are used in methods for treating malignancies. For example, a malignancy of particular interest in this patent is a cancer of the gastrointestinal system, more preferably of the colon and rectum, pancreas, as well as ovarian cancer.

The compositions for treatment contain at least one naked humanized, chimeric or human anti-CSAp antibody or fragment thereof alone or in combination with other anti-CSAp antibodies or antibody fragments thereof, such as other anti-CSAp humanized, chimeric or human antibodies. The present invention also contemplates treatment with at least one naked humanized, chimeric or human anti-CSAp antibody or fragment thereof in combination with other antibodies or antibody fragments thereof that are not anti-CSAp antibodies, whereby these other antibodies can be administered unconjugated (naked) or conjugated with a therapeutic compound. For example, other antibodies suitable for combination therapy include, but are not limited to, carcinoma-associated antibodies and fragments thereof such as antibodies against CEA, EGP-1, Ga 733 antigen target, such as for antibodies EGP-2, 17-1A, KS1-4 and Ep-CAM, MUC1, MUC2, MUC 3, MUC-4, PAM-4, KC4, TAG-72, EGFR, HER2/neu, BrE3, Le-Y, KS-1, A3, anti-necrosis antibodies, and the A33 antibody determinant. Suitable antibodies could also include those targeted against oncogene markers or products, or antibodies against tumor-vasculature markers, such as the angiogenesis factor, VEGF, and antibodies against certain immune response modulators, such as antibodies to CD40. Additionally, treatment can be effected with at least one humanized, chimeric or human anti-CSAp immunoconjugate or fragment thereof alone or in combination with other anti-CSAp antibodies or antibody fragments thereof, such as other anti-CSAp humanized, chimeric or human antibodies. Still preferred, compositions for treatment can contain at least one humanized, chimeric or human anti-CSAp immunoconjugate or fragment thereof in combination with other antibodies or antibody fragments thereof that are not anti-CSAp antibodies, these being either naked or conjugated to a therapeutic agent.

Similarly, conjugated and naked anti-CSAp humanized, chimeric or human antibodies may be used alone or may be administered with, but unconjugated to, the various diagnostic or therapeutic agents described herein. Also, naked or conjugated antibodies to the same or different epitope or antigen may be also combined with one or more of the antibodies of the present invention.

Accordingly, the present invention contemplates the administration of humanized, chimeric and human Mu-9 antibodies and fragments thereof alone, as a naked antibody, or administered as a multimodal therapy. Multimodal therapies of the present invention further include immunotherapy with naked or conjugated CSAp antibodies supplemented with administration of other antibodies in the form of naked antibodies, fusion proteins, or as immunoconjugates. For example, a humanized, chimeric or human Mu-9 antibody may be combined with another naked humanized, naked chimeric or naked human Mu-9 antibody, or a humanized, chimeric or human Mu-9 antibody immunoconjugate, such as a humanized, chimeric or human Mu-9 antibody conjugated to an isotope, one or more chemotherapeutic agents, cytokines, enzymes, enzyme-inhibitors, hormones or hormone antagonists, metals, toxins, or a combination thereof. A fusion protein of a humanized, chimeric or human Mu-9 antibody and a toxin or may also be used in this invention. Many different antibody combinations may be constructed, either as naked antibodies or as partly naked and partly conjugated with a therapeutic agent or immunomodulator, or merely in combination with another therapeutic agents, such as a cytotoxic drug or with radiation.

The compositions for treatment contain at least one humanized, chimeric or human monoclonal CSAp antibody or fragment thereof alone or in combination with other antibodies and fragments thereof, such as other naked or conjugated humanized, chimeric, or human antibodies, fusion proteins, or therapeutic agents. In particular, combination therapy with a fully human antibody is also contemplated and is produced by the methods as set forth above.

Naked or conjugated antibodies and fragments thereof to the same or different epitope or antigen may be also combined with one or more of the antibodies or fragments thereof of the present invention. For example, a humanized, chimeric or human naked Mu-9 antibody may be combined with another naked humanized, naked chimeric or naked human Mu-9 antibody, a humanized, chimeric or human naked Mu-9 antibody may be combined with a Mu-9 immunoconjugate, a naked Mu-9 antibody may be combined with a different antibody radioconjugate or an different naked antibody may be combined with a humanized, chimeric or human Mu-9 antibody conjugated to an isotope, or to one or more chemotherapeutic agents, cytokines, toxins, enzymes, enzyme inhibitors, hormones, hormone antagonists, or a combination thereof. A fusion protein of a humanized, chimeric or human Mu-9 antibody and a toxin or immunomodulator may also be used in this invention. Many different antibody combinations, targeting at least two different antigens may be constructed, either as naked antibodies or as partly naked and partly conjugated with a therapeutic agent or immunomodulator, or merely in combination with another therapeutic agents, such as a cytotoxic drug or with radiation.

Multimodal therapies of the present invention further include immunotherapy with naked Mu-9 antibodies or fragments thereof supplemented with administration of antibodies against antigens expressed by colorectal or ovarian carcinomas in the form of naked antibodies, fusion proteins, immunoconjugates, and fragments thereof. In a preferred embodiment, antibodies or fragments thereof for multimodal therapy include, but are not limited to, antibodies against CEA, EGP-1, EGP-2, TAG-72, MUC1, MUC2, MUC3, MUC4, KC4, PAM-4, EGFR, BrE3, Le-Y, KS-1, A3, the A33 antibody and HER2/neu antibodies and fragments thereof, as well as antibodies against angiogenesis factors (e.g., VEGF) or antibodies against oncogene markers or products, as well as antibodies against immunomodulators, (e.g., CD40). These antibodies include polyclonal, monoclonal, chimeric, human or humanized antibodies and fragments thereof that recognize at least one epitope on these antigenic determinants.

In another form of multimodal therapy, subjects receive naked antibodies or fragments thereof, and/or immunoconjugates or fragments thereof, in conjunction with standard cancer chemotherapy. 5-fluorouracil in combination with folinic acid, alone or in combination with irinotecan (CPT-11), is a regimen used to treat colorectal cancer. Other suitable combination chemotherapeutic regimens are well known, such as with oxaliplatin alone, or in combination with these other drugs, to those of skill in the art. In ovarian cancer, still other chemotherapeutic agents may be preferred, such as any one of the taxanes and platinum agents, Thio-TEPA and other alkylating agents (e.g., chlorambucil), as well as gemcitabine and other more recent classes of cytotoxic drugs. In a preferred multimodal therapy, both chemotherapeutic drugs and cytokines are co-administered with an antibody, immunoconjugate or fusion protein according to the present invention. The cytokines, chemotherapeutic drugs and antibody or immunoconjugate can be administered in any order, or together.

A variety of other chemotherapeutic agents may be used in for combination treatment or for making immunoconjugates. Such chemotherapeutic agents include, but are not limited to, adriamycin, dactinomycin, mitomycin, caminomycin, daunomycin, doxorubicin, tamoxifen, taxol and other taxanes, taxotere, vincristine, vinblastine, vinorelbine, etoposide (VP-16), 5-fluorouracil (5FU), cytosine arabinoside, cyclophohphamide, thiotepa, methotrexate, camptothecin, actinomycin-D, mitomycin C, cisplatin (CDDP), aminopterin, combretastatin(s), neomycin, podophyllotoxin(s), TNF-$\alpha$, $\alpha_2\beta_3$ antagonists, calcium ionophores, calcium-flux inducing agents and derivatives and prodrugs thereof. Anti-metabolites such as cytosine arabinoside, amethopterin; anthracyclines; vinca alkaloids and other alkaloids; antibiotics, demecolcine; etoposide; mithramycin; and other anti-tumor alkylating agents are also contemplated for use with the antibodies of the present invention.

In addition, a therapeutic composition of the present invention can contain a mixture or hybrid molecules of monoclonal naked Mu-9 antibodies or their fragments directed to different, non-blocking epitopes on the CSAp molecule. Accordingly, the present invention contemplates therapeutic compositions comprising a mixture of monoclonal Mu-9 antibodies or their fragments that bind at least two CSAp epitopes. Additionally, the therapeutic composition described herein may contain a mixture of Mu-9 antibodies and fragments thereof with varying CDR sequences.

Naked Antibody Therapy

A therapeutically effective amount of the naked chimeric, humanized or human anti-CSAp antibodies, or their fragments can be formulated in a pharmaceutically acceptable excipient. The efficacy of the naked Mu-9 antibodies can also be enhanced by supplementing naked antibodies with one or more other naked antibodies (such as against tumor-associated antigens, or also agonist or antagonist antibodies to immunomodulators, such as CD40 antigen or ligand), with one or more immunoconjugates of Mu-9, with one or more immunoconjugates of the antibodies against tumor-associated antigens other than CSAp, and conjugated with therapeutic agents, including drugs, toxins, cytokines, immunomodulators, hormones, hormone antagonists, enzymes, enzyme inhibitors, therapeutic radionuclides, etc., with one or more therapeutic agents, including drugs, toxins, cytokines, immunomodulators, hormones, enzymes, enzyme inhibitors, therapeutic radionuclides, etc., administered concurrently or sequentially or according to a prescribed dosing regimen, with the Mu-9 antibodies.

Humanized, Chimeric and Human Anti-CSAp Immunoconjugates

Alternatively, conjugates of the Mu-9 antibodies or fragments thereof of the present invention may be administered. For therapy, these conjugates preferably contain a cytotoxic agent. More preferably, the cytotoxic agent is a toxin. An immunoconjugate, as described herein, is a molecule comprising an antibody component and a therapeutic or diagnostic agent, including a peptide which may bear the diagnostic or therapeutic agent. An immunoconjugate retains the immunoreactivity of the antibody component, i.e., the antibody moiety has about the same or slightly reduced ability to bind the cognate antigen after conjugation as before conjugation.

A wide variety of diagnostic/detection and therapeutic reagents can be advantageously conjugated to the antibodies and fragments thereof, of the invention. The therapeutic agents recited here are those agents that also are useful for administration separately with the naked antibody as described above. Therapeutic agents include, for example, chemotherapeutic drugs such as vinca alkaloids and other alkaloids, anthracyclines, epidophyllotoxins, taxanes, antimetabolites, alkylating agents, antibiotics, COX-2 inhibitors, antimitotics, antiangiogenic and apoptotoic agents, particularly doxorubicin, methotrexate, taxol, CPT-11, camptothecans, and others from these and other classes of anticancer agents, and the like. Other useful cancer chemotherapeutic drugs for the preparation of immunoconjugates and antibody fusion proteins include nitrogen mustards, alkyl sulfonates, nitrosoureas, triazenes, folic acid analogs, COX-2 inhibitors, pyrimidine analogs, purine analogs, platinum coordination complexes, hormones, toxins (e.g., RNAse, *Psudomonas* exotoxin), and the like. Suitable chemotherapeutic agents are described in REMINGTON'S PHARMACEUTICAL SCIENCES, 19th Ed. (Mack Publishing Co. 1995), and in GOODMAN AND GILMAN'S THE PHARMACOLOGICAL BASIS OF THERAPEUTICS, 7th Ed. (MacMillan Publishing Co. 1985), as well as revised editions of these publications. Other suitable chemotherapeutic agents, such as experimental drugs, are known to those of skill in the art.

Additionally, a chelator such as DTPA, DOTA, TETA, or NOTA or a suitable peptide, to which a detectable label, such as a fluorescent molecule, or cytotoxic agent, such as a heavy metal or radionuclide, can be conjugated. For example, a therapeutically useful immunoconjugate can be obtained by conjugating a photoactive agent or dye to an antibody composite. Fluorescent compositions, such as fluorochrome, and other chromogens, or dyes, such as porphyrins sensitive to visible light, have been used to detect and to treat lesions by directing the suitable light to the lesion. In therapy, this has been termed photoradiation, phototherapy, or photodynamic therapy (Jori et al. (eds.), PHOTODYNAMIC THERAPY OF TUMORS AND OTHER DISEASES (Libreria Progetto 1985); van den Bergh, *Chem. Britain* 22:430 (1986)). Moreover, monoclonal antibodies have been coupled with photoactivated dyes for achieving phototherapy. Mew et al., *J. Immunol.* 130:1473 (1983); idem., *Cancer Res.* 45:4380 (1985); Oseroff et al., *Proc. Natl. Acad. Sci. USA* 83:8744 (1986); idem., *Photochem. Photobiol.* 46:83 (1987); Hasan et al., *Prog. Clin. Biol. Res.* 288:471 (1989); Tatsuta et al., *Lasers Surg. Med.* 9:422 (1989); Pelegin et al., *Cancer* 67:2529 (1991). However, these earlier studies did not include use of endoscopic therapy applications, especially with the use of antibody fragments or subfragments. Thus, the present invention contemplates the therapeutic use of immunoconjugates comprising photoactive agents or dyes.

A toxin, such as *Pseudomonas* exotoxin, may also be complexed to or form the therapeutic agent portion of an immunoconjugate of the Mu-9 antibody of the present invention, or when used in combination with the naked Mu-9 antibody or conjugates of the Mu-9 antibody, also complexed to the other, non-CSAp antibodies used in this invention. Other toxins suitably employed in the preparation of such conjugates or other fusion proteins, include ricin, abrin, ribonuclease (RNase), DNase I, *Staphylococcal* enterotoxin-A, pokeweed antiviral protein, gelonin, diphtherin toxin, *Pseudomonas* exotoxin, and *Pseudomonas* endotoxin. See, for example, Pastan et al., *Cell* 47:641 (1986), and Goldenberg, *CA—A Cancer Journal for Clinicians* 44:43 (1994). Additional toxins suitable for use in the present invention are known to those of skill in the art and are disclosed in U.S. Pat. No. 6,077,499, which is incorporated in its entirety by reference. These can be derived, for example, from animal, plant and microbial sources, or chemically or recombinantly engineered. The toxin can be a plant, microbial, or animal toxin, or a synthetic variation thereof.

An immunomodulator, such as a cytokine may also be conjugated to, or form the therapeutic agent portion of the anti-CSAp immunoconjugate, or be administered unconjugated to the chimeric, humanized or human anti-CSAp antibodies of the present invention. As used herein, the term "immunomodulator" includes cytokines, stem cell growth factors, lymphotoxins, such as tumor necrosis factor (TNF), and hematopoietic factors, such as interleukins (e.g., interleukin-1 (IL-1), IL-2, IL-3, IL-6, IL-10, IL-12 and IL-18), colony stimulating factors (e.g., granulocyte-colony stimulating factor (G-CSF) and granulocyte macrophage-colony stimulating factor (GM-CSF)), interferons (e.g., interferons-α, -β and -γ), the stem cell growth factor designated "S1 factor," erythropoietin and thrombopoietin. Examples of suitable immunomodulator moieties include IL-2, IL-6, IL-10, IL-12, IL-18, interferon-γ, TNF-α, and the like. Alternatively, subjects can receive naked Mu-9 antibodies and a separately administered cytokine, which can be administered before, concurrently or after administration of the naked Mu-9 antibodies. The Mu-9 antibody may also be conjugated to the immunomodulator. The immunomodulator may also be conjugated to a hybrid antibody consisting of one or more antibodies binding to different antigens. Such an antigen may also be an immunomodulator. For example, CD40 or other immunomodulators may be administered in combination with the anti-CSAp or anti-CSAp/non-CSAp antibody combination either together, before or after the antibody combinations are administered. The Mu-9 antibody may also be used in combination with, or conjugated to, as a fusion protein, an immunomodulating antibody, such as against CD40.

Furthermore, the present invention includes methods of diagnosing or detecting a malignancy in a subject. Diagnosis/detection may be accomplished by administering a diagnostically effective amount of a diagnostic/detection conjugate, formulated in a pharmaceutically acceptable excipient, and detecting said label. For example, radioactive and non-radioactive agents can be used as diagnostic agents. A suitable non-radioactive diagnostic agent is a contrast agent suitable for magnetic resonance imaging, a radiopaque compound for X-rays or computed tomography, or a contrast agent suitable for ultrasound. Magnetic imaging agents include, for example, non-radioactive metals, such as manganese, iron and gadolinium, complexed with metal-chelate combinations that include 2-benzyl-DTPA and its monomethyl and cyclohexyl analogs, when used along with the antibodies of the invention. See U.S. Ser. No. 09/921,290 filed on Oct. 10, 2001, which is incorporated in its entirety by reference. In a preferred embodiment, the contrast agent is an ultrasound-enhancing agent. Still preferred, the ultrasound-enhancing agent is a liposome. Radiopaque and contrast materials are used for enhancing X-rays and computed tomography, and include iodine compounds, barium compounds, gallium compounds, thallium compounds, etc. Specific compounds include barium, diatrizoate; ethiodized oil, gallium citrate, iocarmic acid, iocetamic acid, iodamide, iodipamide, iodoxamic acid, iogulamide, iohexyl, iopamidol, iopanoic acid, ioprocemic acid, iosefamic acid, ioseric acid, iosulamide meglumine, iosemetic acid, iotasul, iotetric acid, iothalamic acid, iotroxic acid, ioxaglic acid, ioxotrizoic acid, ipodate, meglumine, metrizamide, metrizoate, propyliodone, and thallous chloride.

Furthermore, a radiolabeled antibody or immunoconjugate may comprise a γ-emitting radioisotope or a positron-emitter useful for diagnostic imaging. Examples of diagnostic/detection agents include diverse labels, radionuclides, chelators, dyes, contrast agents, fluorescent compounds, chromagens, and other marker moieties. Radionuclides useful for positron emission tomography include, but are not limited to: F-18, Mn-51, Mn-52m, Fe-52, Co-55, Cu-62, Cu-64, Ga-68, As-72, Br-75, Br-76, Rb-82m, Sr-83, Y-86, Zr-89, Tc-94m, In-110, I-120, and I-124. Total decay energies of useful positron-emitting radionuclides are preferably <2,000 keV, more preferably under 1,000 keV, and most preferably <700 keV. Radionuclides useful as diagnostic agents utilizing gamma-ray detection include, but are not limited to: Cr-51, Co-57, Co-58, Fe-59, Cu-67, Ga-67, Se-75, Ru-97, Tc-99m, In-111, In-114m, I-123, I-125, I-131, Yb-169, Hg-197, and Tl-201. Decay energies of useful gamma-ray emitting radionuclides are preferably 20-2000 keV, more preferably 60-600 keV, and most preferably 100-300 keV.

Additionally, radionuclides suitable for treating a diseased tissue include, but are not limited to, P-32, P-33, Sc-47, Fe-59, Cu-64, Cu-67, Se-75, As-77, Sr-89, Y-90, Mo-99, Rh-105, Pd-109, Ag-111, I-125, I-131, Pr-142, Pr-143, Pm-149, Sm-153, Th-161, Ho-166, Er-169, Lu-177, Re-186, Re-188, Re-189, Ir-194, Au-198, Au-199, Pb-211, Pb-212, and Bi-213, Co-58, Ga-67, Br-80m, Tc-99m, Rh-103m, Pt-109, In-111, Sb-119, I-125, Ho-161, Os-189m, Ir-192, Dy-152, At-211, Bi-212, Ra-223, Rn-219, Po-215, Bi-211, Ac-225, Fr-221, At-217, Bi-213 and Fm-255.

Suitable diagnostic imaging isotopes are usually in the range of 20 to 2,000 keV, while suitable therapeutic radionuclides are usually in the range of 20 to 10,000 keV. See for example, U.S. patent application entitled "Labeling Targeting Agents with Gallium-68"—Inventors G. L. Griffiths and W. J. McBride, (U.S. Provisional Application No. 60/342,104), which discloses positron emitters, such as $^{18}$F, $^{68}$Ga, $^{94m}$Tc. and the like, for imaging purposes and which is incorporated in its entirety by reference.

Bispecific Antibody Therapy

The present invention also encompasses the use of the bsAb and a therapeutic agent associated with the linker moieties discussed above in intraoperative, intravascular, and endoscopic tumor and lesion detection, biopsy and therapy as described in U.S. Pat. No. 6,096,289, and incorporated herein by reference.

The antibodies and antibody fragments of the present invention can be employed not only for therapeutic or imaging purposes, but also as aids in performing research in vitro. For example, the bsAbs of the present invention can be used in vitro to ascertain if a targetable construct can form a stable complex with one or more bsAbs. Such an assay would aid the skilled artisan in identifying targetable constructs which form stable complexes with bsAbs. This would, in turn, allow the skilled artisan to identify targetable constructs which are likely to be superior as therapeutic and/or imaging agents.

The assay is advantageously performed by combining the targetable construct in question with at least two molar equivalents of a bsAb. Following incubation, the mixture is analyzed by size-exclusion HPLC to determine whether or not the construct has bound to the bsAb. Alternatively, the assay is performed using standard combinatorial methods wherein solutions of various bsAbs are deposited in a standard 96-well plate. To each well, is added solutions of targetable construct(s). Following incubation and analysis, one can readily determine which construct(s) bind(s) best to which bsAb(s).

It should be understood that the order of addition of the bsAb to the targetable construct is not crucial; that is, the bsAb may be added to the construct and vice versa. Likewise, neither the bsAb nor the construct needs to be in solution; that is, they may be added either in solution or neat, whichever is most convenient. Lastly, the method of analysis for binding is not crucial as long as binding is established. Thus, one may analyze for binding using standard analytical methods including, but not limited to, FABMS, high-field NMR or other appropriate method in conjunction with, or in place of, size-exclusion HPLC.

The present invention provides a bispecific antibody or antibody fragment having at least a binding region that specifically binds a targeted cell marker and at least one other binding region that specifically binds a targetable conjugate. The targetable conjugate comprises a carrier portion which comprises or bears at least one epitope recognized by at least one binding region of the bispecific antibody or antibody fragment.

For example, the anti-CSAp antibodies and fragments thereof, as well as other antibodies with different specificities and fragments thereof, for use in combination therapy, described herein, can also be made as multispecific antibodies (comprising at least one binding site to a CSAp epitope or antigen and at least one binding site to another epitope on CSAp or another antigen) and multivalent antibodies (comprising multiple binding sites to the same epitope or antigen).

A variety of recombinant methods can be used to produce bispecific antibodies and antibody fragments as described above.

In a preferred embodiment, the multivalent antibody is a Mu-9 antibody. A Mu-9 multivalent antibody is also contemplated in the present invention. This multivalent antibody is constructed by association of a first and a second polypeptide. The first polypeptide comprises a first single chain Fv molecule covalently linked to a first immunoglobulin-like domain which preferably is an immunoglobulin light chain variable region domain. The second polypeptide comprises a second single chain Fv molecule covalently linked to a second immunoglobulin-like domain which preferably is an immunoglobulin heavy chain variable region domain. Each of the first and second single chain Fv molecules forms a target binding site, and the first and second immunoglobulin-like domains associate to form a third target binding site.

A single chain Fv molecule with the VL-L-VH configuration, wherein L is a linker, may associate with another single chain Fv molecule with the VH-L-VL configuration to form a bivalent dimer. In this case, the VL domain of the first scFv and the VH domain of the second scFv molecule associate to form one target binding site, while the $V_H$ domain of the first scFv and the VL domain of the second scFv associate to form the other target binding site.

Another embodiment of the present invention is a Mu-9 bispecific, trivalent antibody comprising two heterologous polypeptide chains associated non-covalently to form three binding sites, two of which have affinity for one target and a third which has affinity for a hapten that can be made and attached to a carrier for a diagnostic and/or therapeutic agent. Preferably, the binding protein has two CSAp binding sites and one other antigen binding site. The bispecific, trivalent targeting agents have two different scFvs, one scFv contains two $V_H$ domains from one antibody connected by a short linker to the $V_L$ domain of another antibody and the second scFv contains two $V_L$ domains from the first antibody connected by a short linker to the $V_H$ domain of the other antibody. The methods for generating multivalent, multispecific agents from $V_H$ and $V_L$ domains provide that individual chains synthesized from a DNA plasmid in a host organism are composed entirely of $V_H$ domains (the $V_H$-chain) or entirely of $V_L$ domains (the $V_L$-chain) in such a way that any agent of multivalency and multispecificity can be produced by non-covalent association of one $V_H$-chain with one $V_L$-chain. For example, forming a trivalent, trispecific agent, the $V_H$-chain will consist of the amino acid sequences of three $V_H$ domains, each from an antibody of different specificity, joined by peptide linkers of variable lengths, and the $V_L$-chain will consist of complementary $V_L$ domains, joined by peptide linkers similar to those used for the $V_H$-chain. Since the $V_H$ and $V_L$ domains of antibodies associate in an anti-parallel fashion, the preferred method in this invention has the $V_L$ domains in the $V_L$-chain arranged in the reverse order of the $V_H$ domains in the $V_H$-chain.

Bispecific antibodies and fragments thereof of the present invention are useful in pretargeting methods and provide a preferred way to deliver two therapeutic agents or two diagnostic/detection agents to a subject. U.S. Ser. No. 09/382,186 discloses a method of pretargeting using a bispecific antibody, in which the bispecific antibody is labeled with $^{125}$I and delivered to a subject, followed by a divalent peptide labeled with $^{99m}$Tc. The delivery results in excellent tumor/normal tissue ratios for $^{131}$I and $^{99m}$Tc, thus showing the utility of two diagnostic radioisotopes. Any combination of known therapeutic agents or diagnostic agents can be used to label the antibodies and antibody fusion proteins. The binding specificity of the antibody component of the mAb conjugate, the efficacy of the therapeutic agent or diagnostic agent and the effector activity of the Fc portion of the antibody can be determined by standard testing of the conjugates.

Preparation of Humanized, Chimeric and Human Mu-9 Immunoconjugates

Any of the anti-CSAp antibodies or fragments thereof or antibody fusion proteins or fragments thereof of the present invention can be conjugated with one or more therapeutic or diagnostic agents. Generally, one therapeutic or diagnostic agent is attached to each antibody or antibody fragment but more than one therapeutic agent or diagnostic agent can be attached to the same antibody or antibody fragment. The antibody fusion proteins of the present invention comprise two or more antibodies or fragments thereof and each of the antibodies that compose this fusion protein can contain a therapeutic agent or diagnostic agent. In other words, the antibody fusion protein or fragment thereof can comprise at least one first anti-CSAp MAb or fragment thereof and at least one second MAb or fragment thereof that is not an anti-CSAp MAb. Preferably, the second MAb is a carcinoma-associated antibody, such as an antibody against CEA, EGP-1, EGP-2, MUC1, MUC2, MUC3, MUC4, PAM-4, KC4, TAG-72, EGFR, HER2/neu, BrE3, Le-Y, A3, KS-1, VEGF and other angiogenesis antibodies, oncogene antibodies, anti-necrosis antibodies, or the antibody A33. Additionally, one or more of the antibodies of the antibody fusion protein can have more than one therapeutic or diagnostic/detection agent attached. Further, the therapeutic agents do not need to be the same but can be different therapeutic agents; for example, one can attach a drug and a radioisotope to the same fusion protein. Particularly, an IgG can be radiolabeled with $^{131}$I and attached to a drug. The $^{131}$I can be incorporated into the tyrosine of the IgG and the drug attached to the epsilon amino group of the IgG lysines. Both therapeutic and diagnostic agents also can be attached to reduced SH groups and to the carbohydrate side chains.

Also preferred, the antibody fusion protein of the present invention comprises at least two anti-CSAp monoclonal antibodies or fragments thereof, and these may be to different epitopes of the CSAp antigen or of different human immunoglobulin backbone sequences (or IgGs).

A therapeutic or diagnostic agent can be attached at the hinge region of a reduced antibody component via disulfide bond formation. As an alternative, such peptides can be attached to the antibody component using a heterobifunctional cross-linker, such as N-succinyl 3-(2-pyridyldithio) proprionate (SPDP). Yu et al., *Int. J. Cancer* 56: 244 (1994). General techniques for such conjugation are well known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995). Alternatively, the therapeutic or diagnostic agent can be conjugated via a carbohydrate moiety in the Fc region of the antibody. The carbohydrate group can be used to increase the loading of the same peptide that is bound to a thiol group, or the carbohydrate moiety can be used to bind a different peptide.

Methods for conjugating peptides to antibody components via an antibody carbohydrate moiety are well known to those of skill in the art. See, for example, Shih et al., *Int. J. Cancer* 41: 832 (1988); Shih et al., *Int. J. Cancer* 46: 1101 (1990); and Shih et al., U.S. Pat. No. 5,057,313, all of which are incorporated in their entirety by reference. The general method involves reacting an antibody component having an oxidized carbohydrate portion with a carrier polymer that has at least one free amine function and that is loaded with a plurality of peptide. This reaction results in an initial Schiff base (imine) linkage, which can be stabilized by reduction to a secondary amine to form the final conjugate.

The Fc region is absent if the antibody used as the antibody component of the immunoconjugate is an antibody fragment. However, it is possible to introduce a carbohydrate moiety into the light chain variable region of a full-length antibody or antibody fragment. See, for example, Leung et al., *J. Immunol.* 154: 5919 (1995); Hansen et al, U.S. Pat. No. 5,443,953 (1995), Leung et al., U.S. Pat. No. 6,254,868, all of which are incorporated in their entirety by reference. The engineered carbohydrate moiety is used to attach the therapeutic or diagnostic agent.

V. Constructs Targetable to Antibodies

The targetable construct can be of diverse structure, but is selected not only to avoid eliciting an immune responses, but also for rapid in vivo clearance when used within the bsAb targeting method. Hydrophobic agents are best at eliciting strong immune responses, whereas hydrophilic agents are preferred for rapid in vivo clearance; thus, a balance between hydrophobic and hydrophilic needs to be established. This is accomplished, in part, by relying on the use of hydrophilic chelating agents to offset the inherent hydrophobicity of many organic moieties. Also, subunits of the targetable construct may be chosen which have opposite solution properties, for example, peptides, which contain amino acids, some of which are hydrophobic and some of which are hydrophilic. Aside from peptides, carbohydrates may be used.

Peptides having as few as two amino-acid residues may be used, preferably two to ten residues, if also coupled to other moieties such as chelating agents. The linker should be a low molecular weight conjugate, preferably having a molecular weight of less than 50,000 daltons, and advantageously less than about 20,000 daltons, 10,000 daltons or 5,000 daltons, including the metal ions in the chelates. For instance, the known peptide DTPA-Tyr-Lys(DTPA)-OH (wherein DTPA is diethylenetriaminepentaacetic acid) has been used to generate antibodies against the indium-DTPA portion of the molecule. However, by use of the non-indium-containing molecule, and appropriate screening steps, new Abs against the tyrosyl-lysine dipeptide can be made. More usually, the antigenic peptide will have four or more residues, such as the peptide DOTA-Phe-Lys(HSG)-Tyr-Lys(HSG)-NH$_2$, wherein DOTA is 1,4,7,10-tetraazacyclododecanetetraacetic acid and HSG is the histamine succinyl glycyl group of the formula:

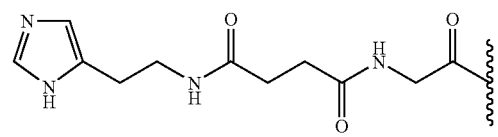

The non-metal-containing peptide may be used as an immunogen, with resultant Abs screened for reactivity against the Phe-Lys-Tyr-Lys backbone.

The invention also contemplates the incorporation of unnatural amino acids, e.g., D-amino acids, into the backbone structure to ensure that, when used with the final bsAb/linker system, the arm of the bsAb which recognizes the linker moiety is completely specific. The invention further contemplates other backbone structures such as those constructed from non-natural amino acids and peptoids.

The peptides to be used as immunogens are synthesized conveniently on an automated peptide synthesizer using a solid-phase support and standard techniques of repetitive orthogonal deprotection and coupling. Free amino groups in the peptide, that are to be used later for chelate conjugation, are advantageously blocked with standard protecting groups such as an acetyl group. Such protecting groups will be known to the skilled artisan. See Greene and Wuts *Protective Groups in Organic Synthesis,* 1999 (John Wiley and Sons, N.Y.). When the peptides are prepared for later use within the bsAb system, they are advantageously cleaved from the resins to generate the corresponding C-terminal amides, in order to inhibit in vivo carboxypeptidase activity.

The haptens of the immunogen comprise an immunogenic recognition moiety, for example, a chemical hapten. Using a chemical hapten, preferably the HSG hapten, high specificity of the linker for the antibody is exhibited. This occurs because antibodies raised to the HSG hapten are known and can be easily incorporated into the appropriate bispecific antibody. Thus, binding of the linker with the attached hapten would be highly specific for the antibody or antibody fragment.

Chelate Moieties

The presence of hydrophilic chelate moieties on the linker moieties helps to ensure rapid in vivo clearance. In addition to hydrophilicity, chelators are chosen for their metal-binding properties, and are changed at will since, at least for those linkers whose bsAb epitope is part of the peptide or is a non-chelate chemical hapten, recognition of the metal-chelate complex is no longer an issue.

Particularly useful metal-chelate combinations include 2-benzyl-DTPA and its monomethyl and cyclohexyl analogs, used with $^{47}Sc$, $^{52}Fe$, $^{55}Co$, $^{67}Ga$, $^{68}Ga$, $^{111}In$, $^{89}Zr$, $^{90}Y$, $^{161}Tb$, $^{177}Lu$, $^{212}Bi$, $^{213}Bi$, and $^{225}Ac$ for radio-imaging and RAIT. The same chelators, when complexed with non-radioactive metals, such as Mn, Fe and Gd can be used for MRI, when used along with the bsAbs of the invention. Macrocyclic chelators such as NOTA (1,4,7-triaza-cyclononane-N,N', N''-triacetic acid), DOTA, and TETA (p-bromoacetamido-benzyl-tetraethylaminetetraacetic acid) are of use with a variety of metals and radiometals, most particularly with radionuclides of Ga, Y and Cu, respectively.

DTPA and DOTA-type chelators, where the ligand includes hard base chelating functions such as carboxylate or amine groups, are most effective for chelating hard acid cations, especially Group IIa and Group IIIa metal cations. Such metal-chelate complexes can be made very stable by tailoring the ring size to the metal of interest. Other ring-type chelators such as macrocyclic polyethers are of interest for stably binding nuclides such as $^{223}Ra$ for RAIT. Porphyrin chelators may be used with numerous radiometals, and are also useful as certain cold metal complexes for bsAb-directed immunophototherapy. More than one type of chelator may be conjugated to a carrier to bind multiple metal ions, e.g., cold ions, diagnostic radionuclides and/or therapeutic radionuclides. Particularly useful therapeutic radionuclides include, but are not limited to, $^{32}P$, $^{33}P$, $^{47}Sc$, $^{64}Cu$, $^{67}Cu$, $^{67}Ga$, $^{90}Y$, $^{111}Ag$, $^{111}In$, $^{125}I$, $^{131}I$, $^{142}Pr$, $^{153}Sm$, $^{161}Tb$, $^{166}Dy$, $^{166}Ho$, $^{177}Lu$, $^{186}Re$, $^{188}Re$, $^{189}Re$, $^{212}Pb$, $^{212}Bi$, $^{213}Bi$, $^{211}At$, $^{223}Ra$ and $^{225}Ac$. Particularly useful diagnostic/detection radionuclides include, but are not limited to, $^{18}F$, $^{52}Fe$, $^{62}Cu$, $^{64}Cu$, $^{67}Cu$, $^{67}Ga$, $^{68}Ga$, $^{86}Y$, $^{89}Zr$, $^{94m}Tc$, $^{94}Tc$, $^{99m}Tc$, $^{111}In$, $^{123}I$, $^{124}I$, $^{125}I$, $^{131}I$, $^{154-158}Gd$ and $^{175}Lu$.

Chelators such as those disclosed in U.S. Pat. No. 5,753, 206, especially thiosemi-carbazonylglyoxylcysteine (Tscg-Cys) and thiosemicarbazinyl-acetylcysteine (Tsca-Cys) chelators are advantageously used to bind soft acid cations of Tc, Re, Bi and other transition metals, lanthanides and actinides that are tightly bound to soft base ligands, especially sulfur- or phosphorus-containing ligands. It can be useful to link more than one type of chelator to a peptide, e.g., a DTPA or similar chelator for, say In(III) cations, and a thiol-containing chelator, e.g., Tscg-Cys, for Tc cations. Because antibodies to a di-DTPA hapten are known (Barbet '395, supra) and are readily coupled to a targeting antibody to form a bsAb, it is possible to use a peptide hapten with cold diDTPA chelator and another chelator for binding a radioisotope, in a pretargeting protocol, for targeting the radioisotope. One example of such a peptide is Ac-Lys(DTPA)-Tyr-Lys(DTPA)-Lys (Tscg-Cys-)-NH$_2$. This peptide can be preloaded with In(III) and then labeled with 99-m-Tc cations, the In(III) ions being preferentially chelated by the DTPA and the Tc cations binding preferentially to the thiol-containing Tscg-Cys. Other hard acid chelators such as NOTA, DOTA, TETA and the like can be substituted for the DTPA groups, and Mabs specific to them can be produced using analogous techniques to those used to generate the anti-di-DTPA Mab.

It will be appreciated that two different hard acid or soft acid chelators can be incorporated into the linker, e.g., with different chelate ring sizes, to bind preferentially to two different hard acid or soft acid cations, due to the differing sizes of the cations, the geometries of the chelate rings and the preferred complex ion structures of the cations. This will permit two different metals, one or both of which may be radioactive or useful for MRI enhancement, to be incorporated into a linker for eventual capture by a pretargeted bsAb.

Preferred chelators include NOTA, DOTA and Tscg and combinations thereof. These chelators have been incorporated into a chelator-peptide conjugate motif as exemplified in the following constructs:

(a) DOTA-Phe-Lys(HSG)-D-Tyr-Lys(HSG)-NH$_2$;

(b) DOTA-Phe-Lys(HSG)-Tyr-Lys(HSG)-NH$_2$;

(c) Ac-Lys(HSG)D-Tyr-Lys(HSG)-Lys(Tscg-Cys)-NH$_2$;

(d)

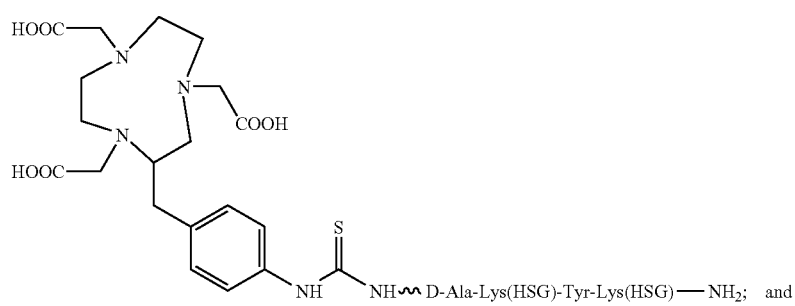

-continued (e)

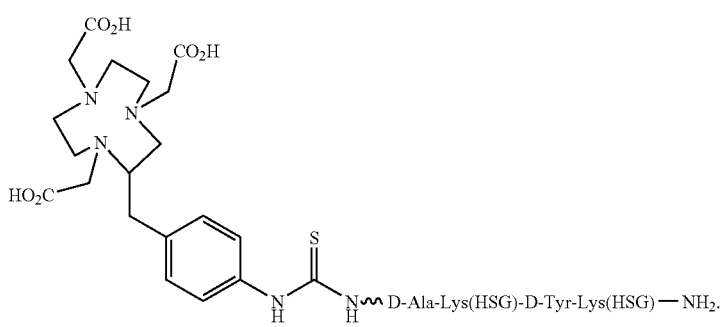 D-Ala-Lys(HSG)-D-Tyr-Lys(HSG)—NH$_2$.

The chelator-peptide conjugates (d) and (e), above, has been shown to bind $^{68}$Ga and is thus useful in positron emission tomography (PET) applications.

Chelators are coupled to the linker moieties using standard chemistries which are discussed more fully in the working Examples below. Briefly, the synthesis of the peptide Ac-Lys(HSG)D-Tyr-Lys(HSG)-Lys(Tscg-Cys-)-NH$_2$ was accomplished by first attaching Aloc-Lys(Fmoc)-OH to a Rink amide resin on the peptide synthesizer. The protecting group abbreviations "Aloc" and "Fmoc" used herein refer to the groups allyloxycarbonyl and fluorenylmethyloxy carbonyl. The Fmoc-Cys(Trt)-OH and TscG were then added to the side chain of the lysine using standard Fmoc automated synthesis protocols to form the following peptide: Aloc-Lys(Tscg-Cys(Trt)-rink resin. The Aloc group was then removed. The peptide synthesis was then continued on the synthesizer to make the following peptide: (Lys(Aloc)-D-Tyr-Lys(Aloc)-Lys(Tscg-Cys(Trt)-)-rink resin. Following N-terminus acylation, and removal of the side chain Aloc protecting groups. The resulting peptide was then treated with activated N-trityl-HSG-OH until the resin gave a negative test for amines using the Kaiser test. See Karacay et al. *Bioconjugate Chem.* 11:842-854 (2000). The synthesis of Ac-Lys(HSG)D-Tyr-Lys(HSG)-Lys(Tscg-Cys-)-NH$_2$, as well as the syntheses of DOTA-Phe-Lys(HSG)-D-Tyr-Lys(HSG)-NH$_2$; and DOTA-Phe-Lys(HSG)-Tyr-Lys(HSG)-NH$_2$ are described in greater detail below.

Preparation of Metal Chelates

Chelator-peptide conjugates may be stored for long periods as solids. They may be metered into unit doses for metal-binding reactions, and stored as unit doses either as solids, aqueous or semi-aqueous solutions, frozen solutions or lyophilized preparations. They may be labeled by well-known procedures. Typically, a hard acid cation is introduced as a solution of a convenient salt, and is taken up by the hard acid chelator and possibly by the soft acid chelator. However, later addition of soft acid cations leads to binding thereof by the soft acid chelator, displacing any hard acid cations which may be chelated therein. For example, even in the presence of an excess of cold $^{111}$InCl$_3$, labeling with 99m-Tc(V) glucoheptonate or with Tc cations generated in situ with stannous chloride and Na99m-TcO$_4$ proceeds quantitatively on the soft acid chelator. Other soft acid cations such as $^{186}$Re, $^{188}$Re, $^{213}$Bi and divalent or trivalent cations of Mn, Co, Ni, Pb, Cu, Cd, Au, Fe, Ag (monovalent), Zn and Hg, especially $^{64}$Cu and $^{67}$Cu, and the like, some of which are useful for radioimmunodiagnosis or radioimmunotherapy, can be loaded onto the linker peptide by analogous methods. Re cations also can be generated in situ from perrhenate and stannous ions or a prereduced rhenium glucoheptonate or other transchelator can be used. Because reduction of perrhenate requires more stannous ion (typically above 200 μg/mL final concentration) than is needed for the reduction of Tc, extra care needs to be taken to ensure that the higher levels of stannous ion do not reduce sensitive disulfide bonds such as those present in disulfide-cyclized peptides. During radiolabeling with rhenium, similar procedures are used as are used with the Tc-99m. A preferred method for the preparation of ReO metal complexes of the Tscg-Cys-ligands is by reacting the peptide with ReOCl$_3$(P(Ph$_3$)$_2$ but it is also possible to use other reduced species such as ReO(ethylenediamine)$_2$.

VI. Methods of Administration

It should be noted that much of the discussion presented herein below focuses on the use of the inventive bispecific antibodies and targetable constructs in the context of treating diseased tissue. The invention contemplates, however, the use of the inventive bispecific antibodies and targetable constructs in treating and/or imaging tissue and organs using the methods described in U.S. Pat. Nos. 6,126,916; 6,077,499; 6,010,680; 5,776,095; 5,776,094; 5,776,093; 5,772,981; 5,753,206; 5,746,996; 5,697,902; 5,328,679; 5,128,119; 5,101,827; and 4,735,210, so long as there is expression of CSAp in said tissues and organs. As used herein, the term "tissue" refers to diseased tissues, more specifically malignant tissues expressing CSAp, including but not limited to, malignant tissues of the colon, rectum, pancreas, and ovary.

The administration of a bsAb and a therapeutic agent associated with the linker moieties discussed above may be conducted by administering the bsAb at some time prior to administration of the therapeutic agent which is associated with the linker moiety. The doses and timing of the reagents can be readily devised by a skilled artisan, and are dependent on the specific nature of the reagents employed. If a bsAb-F(ab')$_2$ derivative is given first, then a waiting time of 24-72 hr before administration of the linker moiety would be appropriate. If an IgG-Fab' bsAb conjugate is the primary targeting vector, then a longer waiting period before administration of the linker moiety would be indicated, in the range of 3-10 days.

As used herein, the term "therapeutic agent" includes, but is not limited to a drug, prodrug and/or toxin. The terms "drug," "prodrug," and "toxin" are defined throughout the specification. A diagnostic agent is more often used to determine the kind of disease present, while a detection agent is more often used for localization and diagnosis. However, as described herein, the term diagnostic agent can also be used to refer to a detection agent.

After sufficient time has passed for the bsAb to target to the diseased tissue, the diagnostic/detection agent is administered. Subsequent to administration of the diagnostic/detection agent, imaging can be performed. Tumors can be detected in body cavities by means of directly or indirectly viewing various structures to which energy of the appropriate wavelength is delivered and then collected. Lesions at any body site can be viewed so long as nonionizing radiation or energy can be delivered and recaptured from these structures. For example, PET which is a high resolution, non-invasive, imaging technique can be used with the inventive antibodies for the visualization of human disease. In PET, 511 keV gamma photons produced during positron annihilation decay are detected.

The invention generally contemplates the use of diagnostic/detection agents which emit 25-600 keV gamma particles and/or positrons. Examples of such agents include, but are not limited to $^{18}$F, $^{52}$Fe, $^{62}$Cu, $^{64}$Cu, $^{67}$Cu, $^{67}$Ga, $^{68}$Ga, $^{86}$Y, $^{89}$Zr, $^{94m}$Tc, $^{94}$Tc, $^{99m}$Tc, $^{111}$In, $^{123}$I, $^{124}$I, $^{125}$I, $^{131}$I, $^{154-158}$Gd and $^{175}$Lu.

The present antibodies or antibody fragments can be used in a method of photodynamic therapy (PDT) as discussed in U.S. Pat. Nos. 6,096,289; 4,331,647; 4,818,709; 4,348,376; 4,361,544; 4,444,744; 5,851,527.

In PDT, a photosensitizer, e.g., a hematoporphyrin derivative such as dihematoporphyrin ether, is administered to a subject. Anti-tumor activity is initiated by the use of light, e.g., 630 nm. Alternate photosensitizers can be utilized, including those useful at longer wavelengths, where skin is less photosensitized by the sun. Examples of such photosensitizers include, but are not limited to, benzoporphyrin monoacid ring A (BPD-MA), tin etiopurpurin (SnET2), sulfonated aluminum phthalocyanine (AlSPc) and lutetium texaphyrin (Lutex).

Additionally, in PDT, a diagnostic agent is injected, for example, systemically, and laser-induced fluorescence can be used by endoscopes to detect sites of cancer which have accreted the light-activated agent. For example, this has been applied to fluorescence bronchoscopic disclosure of early lung tumors. Doiron et al. *Chest* 76:32 (1979). In another example, the antibodies and antibody fragments can be used in single photon emission. For example, a Tc-99m-labeled diagnostic/detection agent can be administered to a subject following administration of the inventive antibodies or antibody fragments. The subject is then scanned with a gamma camera which produces single-photon emission computed tomographic images and defines the lesion or tumor site.

Therapeutically useful immunoconjugates can be obtained by conjugating photoactive agents or dyes to an antibody composite. Fluorescent and other chromogens, or dyes, such as porphyrins sensitive to visible light, have been used to detect and to treat lesions by directing the suitable light to the lesion. In therapy, this has been termed photoradiation, phototherapy, or photodynamic therapy (Jori et al. (eds.), *Photodynamic Therapy of Tumors and Other Diseases* (Libreria Progetto 1985); van den Bergh, *Chem. Britain* 22:430 (1986)). Moreover, monoclonal antibodies have been coupled with photoactivated dyes for achieving phototherapy. Mew et al., *J. Immunol.* 130:1473 (1983); idem., *Cancer Res.* 45:4380 (1985); Oseroff et al., *Proc. Natl. Acad. Sci. USA* 83:8744 (1986); idem., *Photochem. Photobiol.* 46:83 (1987); Hasan et al., *Prog. Clin. Biol. Res.* 288:471 (1989); Tatsuta et al., *Lasers Surg Med.* 9:422 (1989); Pelegrin et al., *Cancer* 67:2529 (1991). However, these earlier studies did not include use of endoscopic therapy applications, especially with the use of antibody fragments or subfragments. Thus, the present invention contemplates the therapeutic use of immunoconjugates comprising photoactive agents or dyes.

The linker moiety may also be conjugated to an enzyme capable of activating a prodrug at the target site or improving the efficacy of a normal therapeutic by controlling the body's detoxification pathways. Following administration of the bsAb, an enzyme conjugated to the linker moiety, a low MW hapten recognized by the second arm of the bsAb, is administered. After the enzyme is pretargeted to the target site, a cytotoxic drug is injected, which is known to act at the target site. The drug may be one which is detoxified by the mammal's ordinary detoxification processes. For example, the drug may be converted into the potentially less toxic glucuronide in the liver. The detoxified intermediate can then be reconverted to its more toxic form by the pretargeted enzyme at the target site. Alternatively, an administered prodrug can be converted to an active drug by the pretargeted enzyme. The pretargeted enzyme improves the efficacy of the treatment by recycling the detoxified drug. This approach can be adopted for use with any enzyme-drug pair.

Certain cytotoxic drugs that are useful for anticancer therapy are relatively insoluble in serum. Some are also quite toxic in an unconjugated form, and their toxicity is considerably reduced by conversion to prodrugs. Conversion of a poorly soluble drug to a more soluble conjugate, e.g., a glucuronide, an ester of a hydrophilic acid or an amide of a hydrophilic amine, will improve its solubility in the aqueous phase of serum and its ability to pass through venous, arterial or capillary cell walls and to reach the interstitial fluid bathing the tumor. Cleavage of the prodrug deposits the less soluble drug at the target site. Many examples of such prodrug-to-drug conversions are disclosed in Hansen U.S. Pat. No. 5,851,527, incorporated herein in its entirety.

Conversion of certain toxic substances such as aromatic or alicyclic alcohols, thiols, phenols and amines to glucuronides in the liver is the body's method of detoxifying them and making them more easily excreted in the urine. One type of antitumor drug that can be converted to such a substrate is epirubicin, a 4-epimer of doxorubicin (Adriamycin), which is an anthracycline glycoside and has been shown to be a substrate for human beta-D-glucuronidase See, e.g., Arcamone *Cancer Res.* 45:5995 (1985). Other analogues with fewer polar groups are expected to be more lipophilic and show greater promise for such an approach. Other drugs or toxins with aromatic or alicyclic alcohol, thiol or amine groups are candidates for such conjugate formation. These drugs, or other prodrug forms thereof, are suitable candidates for the site-specific enhancement methods of the present invention.

The prodrug CPT-11 (irinotecan) is converted in vivo by carboxylesterase to the active metabolite SN-38. One application of the invention, therefore, is to use a bsAb targeted against a tumor and a hapten (e.g. di-DTPA) followed by injection of a di-DTPA-carboxylesterase conjugate. Once a suitable tumor-to-background localization ratio has been achieved, the CPT-11 is given and the tumor-localized carboxylesterase serves to convert CPT-11 to SN-38 at the tumor. Due to its poor solubility, the active SN-38 will remain in the vicinity of the tumor and, consequently, will exert an effect on adjacent tumor cells that are negative for the antigen being targeted. This is a further advantage of the method. Modified forms of carboxylesterases have been described and are within the scope of the invention. See, e.g., Potter et al., *Cancer Res.* 58:2646-2651 (1998) and Potter et al., *Cancer Res.* 58:3627-3632 (1998).

Etoposide is a widely used cancer drug that is detoxified to a major extent by formation of its glucuronide and is within the scope of the invention. See, e.g., Hande et al., *Cancer Res.*

48:1829-1834 (1988). Glucuronide conjugates can be prepared from cytotoxic drugs and can be injected as therapeutics for tumors pre-targeted with mAb-glucuronidase conjugates. See, e.g., Wang et al., *Cancer Res.* 52:4484-4491 (1992). Accordingly, such conjugates also can be used with the pre-targeting approach described here. Similarly, designed prodrugs based on derivatives of daunomycin and doxorubicin have been described for use with carboxylesterases and glucuronidases. See, e.g., Bakina et al., *J. Med. Chem.* 40:4013-4018 (1997). Other examples of prodrug/ enzyme pairs that can be used within the present invention include, but are not limited to, glucuronide prodrugs of hydroxy derivatives of phenol mustards and beta-glucuronidase; phenol mustards or CPT-11 and carboxypeptidase; methotrexate-substituted alpha-amino acids and carboxypeptidase A; penicillin or cephalosporin conjugates of drugs such as 6-mercaptopurine and doxorubicin and beta-lactamase; etoposide phosphate and alkaline phosphatase.

The enzyme capable of activating a prodrug at the target site or improving the efficacy of a normal therapeutic by controlling the body's detoxification pathways may alternatively be conjugated to the hapten. The enzyme-hapten conjugate is administered to the subject following administration of the pre-targeting bsAb and is directed to the target site. After the enzyme is localized at the target site, a cytotoxic drug is injected, which is known to act at the target site, or a prodrug form thereof which is converted to the drug in situ by the pretargeted enzyme. As discussed above, the drug is one which is detoxified to form an intermediate of lower toxicity, most commonly a glucuronide, using the mammal's ordinary detoxification processes. The detoxified intermediate, e.g., the glucuronide, is reconverted to its more toxic form by the pretargeted enzyme and thus has enhanced cytotoxicity at the target site. This results in a recycling of the drug. Similarly, an administered prodrug can be converted to an active drug through normal biological processes. The pretargeted enzyme improves the efficacy of the treatment by recycling the detoxified drug. This approach can be adopted for use with any enzyme-drug pair.

The invention further contemplates the use of the inventive bsAb and the diagnostic agent(s) in the context of Boron Neutron Capture Therapy (BNCT) protocols. BNCT is a binary system designed to deliver ionizing radiation to tumor cells by neutron irradiation of tumor-localized $^{10}$B atoms. BNCT is based on the nuclear reaction which occurs when a stable isotope, isotopically enriched $^{10}$B (present in 19.8% natural abundance), is irradiated with thermal neutrons to produce an alpha particle and a $^{7}$Li nucleus. These particles have a path length of about one cell diameter, resulting in high linear energy transfer. Just a few of the short-range 1.7 MeV alpha particles produced in this nuclear reaction are sufficient to target the cell nucleus and destroy it. Success with BNCT of cancer requires methods for localizing a high concentration of $^{10}$B at tumor sites, while leaving non-target organs essentially boron-free. Compositions and methods for treating tumors in subjects using pre-targeting bsAb for BNCT are described in co-pending patent application Ser. No. 09/205, 243, incorporated herein in its entirety and can easily be modified for the purposes of the present invention.

It should also be noted that a bispecific antibody or antibody fragment can be used in the present method, with at least one binding site specific to an antigen at a target site and at least one other binding site specific to the enzyme component of the antibody-enzyme conjugate. Such an antibody can bind the enzyme prior to injection, thereby obviating the need to covalently conjugate the enzyme to the antibody, or it can be injected and localized at the target site and, after non-targeted antibody has substantially cleared from the circulatory system of the mammal, enzyme can be injected in an amount and by a route which enables a sufficient amount of the enzyme to reach a localized antibody or antibody fragment and bind to it to form the antibody-enzyme conjugate in situ.

It should also be noted that the invention also contemplates the use of multivalent target-binding proteins which have at least three different target binding sites as described in patent application Ser. No. 09/911,610, and is incorporated herein by reference. Multivalent antibodies have been made by cross-linking several Fab-like fragments via chemical linkers. See U.S. Pat. Nos. 5,262,524; 5,091,542 and Landsdorp et al., *Europ. J. Immunol.* 16: 679-83 (1986). Multivalent antibodies also have been made by covalently linking several single chain Fv molecules (scFv) to form a single polypeptide. See U.S. Pat. No. 5,892,020. A multivalent antibody which is basically an aggregate of scFv molecules has been disclosed in U.S. Pat. Nos. 6,025,165 and 5,837,242. A trivalent target binding protein comprising three scFv molecules has been described in Krott et al. *Protein Engineering* 10(4): 423-433 (1997).

A clearing agent may be used which is given between doses of the bsAb and the linker moiety. The present inventors have discovered that a clearing agent of novel mechanistic action may be used with the invention, namely a glycosylated anti-idiotypic (anti-Id) Fab' fragment targeted against the disease targeting arm(s) of the bsAb. For example, anti-CSAp (Mu-9 Ab)×anti-peptide bsAb is given and allowed to accrete in disease targets to its maximum extent. To clear residual bsAb, an anti-idiotypic (anti-Id) Ab to Mu-9 is given, preferably as a glycosylated Fab' fragment. The clearing agent binds to the bsAb in a monovalent manner, while its appended glycosyl residues direct the entire complex to the liver, where rapid metabolism takes place. Then the therapeutic which is associated with the linker moiety is given to the subject. The anti-Id Ab to the Mu-9 arm of the bsAb has a high affinity and the clearance mechanism differs from other disclosed mechanisms (see Goodwin et al., ibid), as it does not involve cross-linking, because the anti-Id-Fab' is a monovalent moiety.

VII. Pharmaceutically Suitable Excipient

The humanized, chimeric or human anti-CSAp antibodies and fragments thereof to be delivered to a subject can consist of the antibody alone, immunoconjugate, fusion protein, or can comprise one or more pharmaceutically suitable excipients, one or more additional ingredients, or some combination of these. Preferably, the anti-CSAp antibody is a Mu-9 antibody.

The Mu-9 immunoconjugate, naked antibody, fusion protein, and fragments thereof of the present invention can be formulated according to known methods to prepare pharmaceutically useful compositions, whereby the immunoconjugate or naked antibody is combined in a mixture with a pharmaceutically suitable excipient. Sterile phosphate-buffered saline is one example of a pharmaceutically suitable excipient. Other suitable excipients are well known to those in the art. See, for example, Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The immunoconjugate, naked antibody, fusion protein, and fragments thereof of the present invention can be formulated for intravenous administration via, for example, bolus injection or continuous infusion. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

Additional pharmaceutical methods may be employed to control the duration of action of the therapeutic or diagnostic conjugate or naked antibody. Control release preparations can be prepared through the use of polymers to complex or adsorb the immunoconjugate or naked antibody. For example, biocompatible polymers include matrices of poly(ethylene-co-vinyl acetate) and matrices of a polyanhydride copolymer of a stearic acid dimer and sebacic acid. Sherwood et al., *Bio/Technology* 10: 1446 (1992). The rate of release of an immunoconjugate or antibody from such a matrix depends upon the molecular weight of the immunoconjugate or antibody, the amount of immunoconjugate, antibody within the matrix, and the size of dispersed particles. Saltzman et al., *Biophys. J.* 55:163 (1989); Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The immunoconjugate, antibody fusion proteins, or naked antibody may also be administered to a mammal subcutaneously or even by other parenteral routes. Moreover, the administration may be by continuous infusion or by single or multiple boluses. In general, the dosage of an administered immunoconjugate, fusion protein or naked antibody for humans will vary depending upon such factors as the patient's age, weight, height, sex, general medical condition and previous medical history. Typically, it is desirable to provide the recipient with a dosage of immunoconjugate, antibody fusion protein or naked antibody that is in the range of from about 1 mg/kg to 20 mg/kg as a single intravenous infusion, although a lower or higher dosage also may be administered as circumstances dictate. This dosage may be repeated as needed, for example, once per week for 4-10 weeks, preferably once per week for 8 weeks, and more preferably, once per week for 4 weeks. It may also be given less frequently, such as every other week for several months, or even less frequently, as may be the case for radioimmunoconjugates. The dosage may be given through various parenteral routes, with appropriate adjustment of the dose and schedule.

For purposes of therapy, the immunoconjugate, fusion protein, or naked antibody, and fragments thereof are administered to a subject in a therapeutically effective amount. A suitable subject for the present invention is a mammal, preferably a human but a non-human mammal such as a dog, cat or horse is also contemplated. An antibody preparation is said to be administered in a "therapeutically effective amount" if the amount administered is physiologically significant. An agent is physiologically significant if its presence results in a detectable change in the physiology of a recipient mammal.

For diagnostic purposes, the immunoconjugate, fusion protein, or naked antibody, and fragments thereof are administered to a subject in a diagnostically effective amount. An antibody preparation is said to be administered in a "diagnostically effective amount" if the amount administered is generally sufficient to diagnose or detect a condition, malignancy, disease or disorder in a subject, usually without any pharmacological effects on the host.

VIII. Expression Vectors

The present invention also embraces nucleic acids that encode chimeric, humanized or human anti-CSAp antibodies, fusion proteins and fragments thereof. Expression vectors that comprise such nucleic acids also are included in the invention. The DNA sequence encoding a humanized, chimeric or human Mu-9 antibody can be recombinantly engineered into a variety of known host vectors that provide for replication of the nucleic acid. These vectors can be designed, using known methods, to contain the elements necessary for directing transcription, translation, or both, of the nucleic acid in a cell to which it is delivered. Known methodology can be used to generate expression constructs that have a protein-coding sequence operably linked with appropriate transcriptional/translational control signals. These methods include in vitro recombinant DNA techniques and synthetic techniques. For example, see Sambrook et al., 1989, MOLECULAR CLONING: A LABORATORY MANUAL, Cold Spring Harbor Laboratory (New York); Ausubel et al., 1997, CURRENT PROTOCOLS IN MOLECULAR BIOLOGY, John Wiley & Sons (New York). Also provided, for in this invention is the delivery of a polynucleotide not associated with a vector.

Vectors suitable for use in the instant invention can be viral or non-viral. Particular examples of viral vectors include adenovirus, AAV, herpes simplex virus, lentivirus, and retrovirus vectors. An example of a non-viral vector is a plasmid. In a preferred embodiment, the vector is a plasmid.

An expression vector, as described herein, is a polynucleotide comprising a gene that is expressed in a host cell. Typically, gene expression is placed under the control of certain regulatory elements, including constitutive or inducible promoters, tissue-specific regulatory elements, and enhancers. Such a gene is said to be "operably linked to" the regulatory elements.

Preferably, the expression vector of the instant invention comprises the DNA sequence encoding a humanized, chimeric or human Mu-9 antibody, which includes both the heavy and the light chain variable and constant regions. However, two expression vectors may be used, with one comprising the heavy chain variable and constant regions and the other comprising the light chain variable and constant regions. Still preferred, the expression vector further comprises a promoter, a DNA sequence encoding a secretion signal peptide, a genomic sequence encoding a human IgG1 heavy chain constant region, an Ig enhancer element and at least one DNA sequence encoding a selection marker.

The representative embodiments described below are simply used to illustrate the invention. Those skilled in these arts will recognize that variations of the present materials fall within the broad generic scope of the claimed invention. The contents of all references mentioned herein are incorporated by reference.

IX. EXAMPLES

Example 1

Synthesis of Ac-Lys(HSG)-D-Tyr-Lys(HSG)-Lys (Tscg-Cys-)-NH$_2$ (IMP 243)

The peptide was synthesized as described by Karacay et. al. *Bioconjugate Chem.* 11:842-854 (2000) except D-tyrosine was used in place of the L-tyrosine and the N-trityl-HSG-OH was used in place of the DTPA. The final coupling of the N-trityl-HSG-OH was carried out using a ten fold excess of N-trityl-HSG-OH relative to the peptide on the resin. The N-trityl-HSG-OH (0.28 M in NMP) was activated using one equivalent (relative to HSG) of N-hydroxybenzotriazole, one equivalent of berizotrazole-1-yl-oxy-tris-(dimethylamino) phosphonium hexafluorophosphate (BOP) and two equivalents of diisopropylethylamine. The activated substrate was mixed with the resin for 15 hr at room temperature.

Example 2

Tc-99m Kit Formulation Comprising IMP 243

A formulation buffer was prepared which contained 22.093 g hydroxypropyl-β-cyclodextrin, 0.45 g 2,4-dihydroxybenzoic acid, 0.257 g acetic acid sodium salt, and 10.889 g α-D-glucoheptonic acid sodium salt dissolved in 170 mL nitrogen degassed water. The solution was adjusted to pH 5.3 with a few drops of 1 M NaOH then further diluted to a total volume of 220 mL. A stannous buffer solution was prepared by diluting 0.2 mL of $SnCl_2$ (200 mg/mL) with 3.8 mL of the formulation buffer. The peptide Ac-Lys(HSG)-D-Tyr-Lys(HSG)-Lys(Tscg-Cys-)-$NH_2$ (0.0026 g), was dissolved in 78 mL of the buffer solution and mixed with 0.52 mL of the stannous buffer. The peptide solution was then filtered through a 0.22 □m Millex GV filter in 1.5 mL aliquots into 3 mL lyophilization vials. The filled vials were frozen immediately, lyophilized and crimp sealed under vacuum.

Pertechnetate solution (27 mCi) in 1.5 mL of saline was added to the kit. The kit was incubated at room temperature for 10 min and heated in a boiling water bath for 25 min. The kit was cooled to room temperature before use.

Example 3

Peptides for Carrying Therapeutic/Imaging Radioisotopes to Tumors via Bispecific Antibody Tumor Pretargeting DOTA-Phe-Lys(HSG)-Tyr-Lys(HSG)-$NH_2$ (MP 237) was synthesized to deliver therapeutic radioisotopes such as $^{90}Y$ or $^{177}Lu$ to tumors via bispecific antibody tumor pretargeting. The bispecific antibody is composed of one portion which binds to an antigen on the tumor and another portion which binds to the HSG peptide. The antibody which binds the HSG peptide is 679. This system can also be used to deliver imaging isotopes such as $^{111}In$-111.

Synthesis of IMP 237

IMP 237 was synthesized on Sieber Amide resin (NovaBiochem) using standard Fmoc based solid phase peptide synthesis to assemble the peptide backbone with the following protected amino acids, in order: Fmoc-Lys(Aloc)-OH, Fmoc-Tyr(But)-OH, Fmoc-Lys(Aloc)-OH, Fmoc-Phe-OH, (Reagents from Advanced Chemtech) tri-t-butyl DOTA (Macrocyclics). The side lysine side chains were then deprotected with $Pd[P(Ph)_3]_4$ by the method of Dangles et. al. *J. Org. Chem.* 52:4984-4993 (1987). The HSG ligands were then added as Trityl HSG (synthesis described below) using the BOP/HBTU double coupling procedure used to attach the amino acids. The peptide was cleaved from the resin and the protecting groups were removed by treatment with TFA. The peptide was purified by HPLC to afford 0.6079 g of peptide from 1.823 g of Fmoc-Lys(Aloc)-Tyr(But)-Lys(Aloc)-NH-Sieber amide resin.

Synthesis of N-Trityl-HSG-OH

Glycine t-butyl ester hydrochloride (15.263 g, $9.1 \times 10^{-2}$ mol) and 19.760 g $Na_2CO_3$ were mixed, then suspended in 50 mL $H_2O$ and cooled in an ice bath. Succinic anhydride (9.142 g, $9.14 \times 10^{-2}$ mol) was then added to the reaction solution which was allowed to warn slowly to room temperature and stir for 18 hr. Citric acid (39.911 g) was dissolved in 50 mL $H_2O$ and slowly added to the reaction solution and then extracted with 2×150 mL EtOAc. The organic extracts were dried over $Na_2SO_4$, filtered and concentrated to afford 25.709 g of a white solid.

The crude product (25.709 g) was dissolved in 125 mL dioxane, cooled in a room temperature water bath and mixed with 11.244 g of N-hydroxysuccinimide. Diisopropylcarbodiimide 15.0 mL was added to the reaction solution which was allowed to stir for one hour. Histamine dihydrochloride (18.402 g, $1.00 \times 10^{-1}$ mol) was then dissolved in 100 mL DMF and 35 mL diisopropylethylamine. The histamine mixture was added to the reaction solution which was stirred at room temperature for 21 hr. The reaction was quenched with 100 mL water and filtered to remove a precipitate. The solvents were removed under hi-vacuum on the rotary evaporator. The crude product was dissolved in 300 mL dichloromethane and extracted with 100 mL saturated $NaHCO_3$. The organic layer was dried over $Na_2SO_4$ and concentrated to afford 34.19 g of crude product as a yellow oil.

The crude product (34.19 g) was dissolved in 50 mL chloroform and mixed with 31 mL diisopropylethylamine. Triphenylmethyl chloride (25.415 g) was dissolved in 50 ml chloroform and added dropwise to the stirred reaction solution which was cooled in an ice bath. The reaction was stirred for 45 min and then quenched with 100 mL $H_2O$. The layers were separated and the organic solution was dried over $Na_2SO_4$ and concentrated to form a green gum. The gum was triturated with 100 mL $Et_2O$ to form a yellow precipitate which was washed with 3×590 mL portions of $Et_2O$. The solid was vacuum dried to afford 30.641 g (59.5% overall yield) of N-trityl-HSG-t-butyl ester.

N-trityl-HSG-t-butyl ester (20.620 g, $3.64 \times 10^{-2}$ mol) was dissolved in a solution of 30 mL chloroform and 35 mL glacial acetic acid. The reaction was cooled in an ice bath and 15 mL of $BF_3 \cdot Et_2O$ was slowly added to the reaction solution. The reaction was allowed to warn slowly to room temperature and mix for 5 hr. The reaction was quenched by pouring into 200 mL 1M NaOH and the product was extracted with 200 mL chloroform. The organic layer was dried over $Na_2SO_4$ and concentrated to afford a crude gum which was triturated with 100 mL $Et_2O$ to form a precipitate. The crude precipitate was poured into 400 mL 0.5 M pH 7.5 phosphate buffer and extracted with 2×200 mL EtOAc. The aqueous layer was acidified to pH 3.5 with 1 M HCl and extracted with 2×200 mL chloroform. A precipitate formed and was collected by filtration (8.58 g). The precipitate was the desired product by HPLC comparison to a previous sample (ESMS MH+511).

Radiolabeling $^{90}Y$ Kit Preparation

DOTA-Phe-Lys(HSG)-Tyr-Lys(HSG)-$NH_2$ was dissolved in 0.25 M $NH_4Ac$/10% HPCD buffer at concentrations of 9, 18, 35, 70 and 140 µg/mL. The solutions were sterile filtered through a 0.22 µm Millex GV filter in one µL aliquots into acid washed lyophilization vials. The filled vials were frozen immediately on filling and lyophilized. When the lyophilization cycle was complete the vials were sealed under vacuum and crimp sealed upon removal from the lyophilizer.

The $^{90}Y$ (~400 µCi/kit) was diluted to 1 mL in deionized water and added to the lyophilized kits. The kits were heated in a boiling water bath for 15 min, the vials were cooled to room temperature and the labeled peptides were evaluated by reverse phase HPLC (HPLC conditions: Waters Nova-Pak C-18, 8×100 mm RCM column eluted at 3 mL/min with a linear gradient from 100% (0.1% TFA in $H_2O$) to 100% (90% $CH_3CN$, 0.1% TFA, 10% $H_2O$)). The HPLC analysis revealed that the minimum concentration of peptide needed for complete labeling, with this formulation, was 35 μg/mL. The reverse phase HPLC trace showed a sharp $^{90}Y$ labeled peptide peak. The labeled peptide was completely bound when mixed with excess 679 IgG by size exclusion HPLC.

Labeling with $^{111}In$

The $^{111}In$ (~300 μCi/kit) was diluted to 0.5 mL in deionized water and added to the lyophilized kits. The kits were heated in a boiling water bath for 15 min, the vials were cooled and 0.5 mL of $2.56×10^{-5}$ M In in 0.5 M acetate buffer was added and the kits were again heated in the boiling water bath for 15 min. The labeled peptide vials were cooled to room temperature and evaluated by reverse phase HPLC (HPLC conditions: Waters Nova-Pak C-18, 8×100 mm RCM column eluted at 3 mL/min with a linear gradient from 100% (0.1% TFA in $H_2O$) to 100% (90% $CH_3CN$, 0.1% TFA, 10% $H_2O$)). The HPLC analysis revealed that the minimum concentration of peptide needed for labeling (4.7% loose $^{111}In$), with this formulation, was 35 μg/mL. The reverse phase HPLC trace showed a sharp $^{111}In$ labeled peptide peak. The labeled peptide was completely bound when mixed with excess 679 IgG by size exclusion HPLC.

In-Vivo Studies

Nude mice bearing GW-39 human colonic xenograft tumors (100-500 mg) were injected with the bispecific antibody hMN-14×m679 ($1.5×10^{-10}$ mol). The antibody was allowed to clear for 24 hr before the $^{111}In$ labeled peptide (8.8 μCi, $1.5×10^{-11}$ mol) was injected. The animals were sacrificed at 3, 24, 48 hr post injection.

The results of the biodistribution studies of the peptide in the mice pretargeted with hMN-14×m679 are shown in Table 1. The tumor to non-tumor ratios of the peptides in the pretargeting study are show in Table 2.

TABLE 1

Pretargeting With $^{111}In$ Labeled Peptide 24 hr After Injection of hMN-14 x m679 % Injected/g Tissue

| Tissue | 3 hr After $^{111}In$ IMP 237 | 24 hr After $^{111}In$ IMP 237 | 48 hr After $^{111}In$ IMP 237 |
|---|---|---|---|
| GW-39 | 7.25 ± 2.79 | 8.38 ± 1.70 | 5.39 ± 1.46 |
| Liver | 0.58 ± 0.13 | 0.62 ± 0.09 | 0.61 ± 0.16 |
| Spleen | 0.50 ± 0.14 | 0.71 ± 0.16 | 0.57 ± 0.15 |
| Kidney | 3.59 ± 0.75 | 2.24 ± 0.40 | 1.27 ± 0.33 |
| Lungs | 1.19 ± 0.26 | 0.44 ± 0.10 | 0.22 ± 0.06 |
| Blood | 2.42 ± 0.61 | 0.73 ± 0.17 | 0.17 ± 0.06 |
| Stomach | 0.18 ± 0.03 | 0.09 ± 0.02 | 0.07 ± 0.02 |
| Sm. Int. | 0.65 ± 0.74 | 0.18 ± 0.03 | 0.11 ± 0.02 |
| Lg. Int. | 0.30 ± 0.07 | 0.17 ± 0.03 | 0.13 ± 0.03 |

TABLE 2

Pretargeting With $^{111}In$ Labeled Peptides 24 hr After Injection of hMN-14 x m679 Tumor/Non-Tumor Tissue Ratios

| Tissue | 3 hr After $^{111}In$ IMP 237 | 24 hr After $^{111}In$ IMP 237 | 48 hr After $^{111}In$ IMP 237 |
|---|---|---|---|
| Liver | 12.6 ± 4.44 | 13.6 ± 2.83 | 8.88 ± 1.78 |
| Spleen | 15.1 ± 6.32 | 12.1 ± 2.86 | 9.50 ± 1.62 |
| Kidney | 2.04 ± 0.74 | 3.84 ± 1.04 | 4.25 ± 0.19 |
| Lungs | 6.11 ± 1.96 | 19.6 ± 5.91 | 25.4 ± 6.00 |
| Blood | 3.04 ± 1.13 | 11.9 ± 3.20 | 31.9 ± 4.79 |
| Stomach | 40.5 ± 16.5 | 104. ± 39.6 | 83.3 ± 16.5 |
| Sm. Int. | 18.9 ± 12.6 | 47.5 ± 10.3 | 49.5 ± 7.83 |
| Lg. Int. | 25.2 ± 10.6 | 50.1 ± 16.7 | 43.7 ± 9.35 |

Serum Stability of DOTA-Phe-Lys(HSG)-Tyr-Lys(HSG)-NH2 (IMP 237) and DOTA-Phe-Lys(HSG)-D-Tyr-Lys(HSG)-NH2 (IMP 241)

Peptide Labeling and HPLC Analysis

The peptides, IMP 237 and IMP 241, were labeled according to the procedure described by Karacay et. al. *Bioconjugate Chem.* 11:842-854 (2000). The peptide, IMP 241 (0.0019 g), was dissolved in 587 μl 0.5 M $NH_4Cl$, pH 5.5. A 1.7 μL aliquot of the peptide solution was diluted with 165 μl 0.5 M $NH_4Cl$, pH 5.5. The $^{111}In$ (1.8 mCi) in 10 μL was added to the peptide solution and the mixture was heated in a boiling water bath for 30 min.

The labeled peptide was analyzed by HPLC using a Waters 8×100 mm radial-pak, nova-pak C-18 RCM cartridge column. The column was eluted at 3 mL/min with a linear gradient which started with 100% of 0.1% TFA in water and went to 100% of 0.1% TFA in 90% acetonitrile and 10% water over 10 min. There was about 6% loose $^{111}In$ in this labeling which came out at the void volume of the column (1.6 min). There were also some $^{111}In$ labeled peaks at 5 min and 6.6 to 8 min. The $^{111}In$ labeled peptide was eluted at 8.8 min as a single peak. The HPLC profile of $^{111}In$ IMP 237 was nearly identical to $^{111}In$ IMP 241.

Serum Stability

An aliquot (30 μL) of $^{111}In$ IMP 241 was placed in 300 μL of fresh mouse serum and placed in a 37° C. incubator. The peptide was monitored as described above by HPLC.

An aliquot (24 μL) of $^{111}In$ IMP 237 was placed in 230 μL of fresh mouse serum and placed in a 37° C. incubator. The peptide was monitored as described above by HPLC.

The analysis showed that the $^{11}In$ IMP 241 may have decomposed slightly (~5%) after heating 22 hr in mouse serum at 37° C. The $^{111}In$ IMP 237 was about 70% converted to the shorter retention time peak after incubation for 22 hr at 37° C.

Conclusion

The D-tyrosine in the IMP 241 peptide slows the decomposition of the peptide in mouse serum compared to IMP 237.

In Vivo Stability of IMP 237 and IMP 241 Compared

The in vivo stabilities of $^{111}In$ IMP 237 and $^{111}In$ IMP 241 were compared by examining (by HPLC) urine samples from mice at 30 and 60 min. The peptides, IMP 241 and IMP 237, were $^{111}In$-111 labeled as described above.

The labeled peptides were injected into Balb/c mice which were sacrificed at 30 min and 60 min post injection of the peptides using one mouse per time point. The attached HPLC traces indicate that $^{111}In$ IMP 241 was excreted intact while $^{111}In$ IMP 237 was almost completely metabolized to a new $^{111}In$ labeled peptide.

Conclusion

The replacement of Tyr with D-Tyr in the peptide backbone minimized metabolism of the peptide in-vivo.

Additional In Vivo Studies

Nude mice bearing GW-39 human colonic xenograft tumors (100-500 mg) were injected with the bispecific antibody mMu9×m679 ($1.5 \times 10^{-10}$ mol). The antibody was allowed to clear for 48 hr before the $^{111}$In labeled peptides (8.8 µCi, $1.5 \times 10^{-11}$ mol) were injected. The animals were sacrificed at 3, 24, 48 hr post injection.

The results of the biodistribution studies of the peptides in the mice pretargeted with mMU9×m679 are shown in Table 3. The tumor to non-tumor ratios of the peptides in the pretargeting study are show in Table 4. The data in Table 5 shows the biodistribution of the peptides in mice that were not pretreated with the bispecific antibody.

Example 4

PCR Cloning of the Mu-9 Variable Regions

Poly A mRNA was isolated from Mu-9 hybridoma cell line ($\approx 3 \times 10^7$ cells) using the Fast Track mRNA Isolation kit (Invitrogen, San Diego, Calif.). The first strand cDNA was reverse transcribed from poly A mRNA using the cDNA cycle kit (Invitrogen). Briefly, 1 µg of poly A mRNA was annealed to murine IgG CH1-specific primer, CH1B (5' ACA GTC ACT GAG CTG G 3'), or murine Ck-specific primer, Ck3-BH1 (5' GCC GGA TCC TCA CTG GAT GGT GGG AAG ATG GAT ACA 3'), at a final concentration of 1 µM at 42° for

TABLE 3

Pretargeting With $^{111}$In Labeled Peptides 48 hr After Injection of mMU9 x m679 % Injected/g Tissue

| Tissue | 3 hr After $^{111}$In Peptide | | 24 hr After $^{111}$In Peptide | | 48 hr After $^{111}$In Peptide | |
| --- | --- | --- | --- | --- | --- | --- |
| | IMP 237 | IMP 241 | IMP 237 | IMP 241 | IMP 237 | IMP 241 |
| GW-39 | 18.3 ± 7.17 | 26.7 ± 14.1 | 16.7 ± 8.22 | 14.8 ± 4.56 | 12.9 ± 1.10 | [12.3 ± 2.11 |
| Liver | 0.41 ± 0.10 | 0.66 ± 0.34 | 0.32 ± 0.08 | 0.32 ± 0.09 | 0.28 ± 0.09 | 0.32 ± 0.21 |
| Spleen | 0.34 ± 0.12 | 0.63 ± 0.38 | 0.34 ± 0.12 | 0.25 ± 0.07 | 0.28 ± 0.07 | 0.31 ± 0.22 |
| Kidney | 3.62 ± 0.71 | 4.28 ± 0.77 | 2.51 ± 0.54 | 2.34 ± 0.70 | 1.78 ± 0.38 | 1.17 ± 0.43 |
| Lungs | 0.61 ± 0.15 | 1.03 ± 0.65 | 0.22 ± 0.07 | 0.21 ± 0.07 | 0.12 ± 0.04 | 0.14 ± 0.08 |
| Blood | 1.16 ± 0.48 | 1.78 ± 1.49 | 0.21 ± 0.13 | 0.15 ± 0.05 | 0.08 ± 0.03 | 0.10 ± 0.09 |
| Stomach | 0.12 ± 0.04 | 0.21 ± 0.09 | 0.05 ± 0.01 | 0.05 ± 0.02 | 0.04 ± 0.01 | 0.03 ± 0.02 |
| Sm. Int. | 0.23 ± 0.04 | 0.50 ± 0.27 | 0.12 ± 0.02 | 0.09 ± 0.06 | 0.11 ± 0.08 | 0.07 ± 0.06 |
| Lg. Int. | 0.34 ± 0.16 | 0.38 ± 0.15 | 0.15 ± 0.07 | 0.10 ± 0.02 | 0.12 ± 0.07 | 0.09 ± 0.05 |

TABLE 4

Pretargeting With $^{111}$In Labeled Peptides 48 hr After Injection of mMU9 x m679 Tumor/Non-Tumor Tissue Ratios

| Tissue | 3 hr After $^{111}$In Peptide | | 24 hr After $^{111}$In Peptide | | 48 hr After $^{111}$In Peptide | |
| --- | --- | --- | --- | --- | --- | --- |
| | IMP 237 | IMP 241 | IMP 237 | IMP 241 | IMP 237 | IMP 241 |
| Liver | 45.6 ± 17.8 | 41.8 ± 19.6 | 49.8 ± 16.6 | 47.1 ± 8.68 | 49.1 ± 13.6 | 45.1 ± 13.9 |
| Spleen | 56.8 ± 23.8 | 43.5 ± 9.77 | 47.4 ± 14.7 | 59.6 ± 13.0 | 47.35 ± 10.6 | 50.2 ± 19.0 |
| Kidney | 5.13 ± 2.18 | 6.05 ± 2.41 | 6.43 ± 2.24 | 6.58 ± 2.42 | 7.43 ± 1.02 | 11.2 ± 2.61 |
| Lungs | 30.5 ± 10.6 | 28.4 ± 12.8 | 76.4 ± 34.1 | 72.7 ± 21.9 | 115. ± 36.6 | 102. ± 37.1 |
| Blood | 18.6 ± 12.0 | 19.0 ± 11.8 | 86.9 ± 36.2 | 108. ± 41.0 | 187. ± 76.3 | 181. ± 86.6 |
| Stomach | 156. ± 86.1 | 126. ± 49.6 | 303. ± 95.9 | 328. ± 96.7 | 344. ± 101. | 456. ± 193. |
| Sm. Int. | 80.7 ± 29.0 | 59.0 ± 31.0 | 143. ± 60.7 | 193. ± 83.7 | 153. ± 67.7 | 217. ± 73.5 |
| Lg. Int. | 56.3 ± 19.7 | 78.6 ± 54.4 | 116. ± 36.9 | 155. ± 42.4 | 133. ± 47.6 | 153. ± 43.1 |

TABLE 5

Biodistribution of $^{111}$In Labeled Peptides Alone

| Tissue | 30 min After In-111 Peptide | | 3 hr After In-111 Peptide | | 24 hr After In-111 Peptide | |
| --- | --- | --- | --- | --- | --- | --- |
| | IMP 237 | IMP 241 | IMP 237 | IMP 241 | IMP 237 | IMP 241 |
| GW-39 | 2.99 ± 1.11 | 2.73 ± 0.37 | 0.17 ± 0.05 | 0.31 ± 0.12 | 0.11 ± 0.02 | 0.11 ± 0.08 |
| Liver | 0.48 ± 0.06 | 0.50 ± 0.09 | 0.15 ± 0.02 | 1.07 ± 1.61 | 0.15 ± 0.01 | 0.09 ± 0.04 |
| Spleen | 0.42 ± 0.08 | 0.43 ± 0.22 | 0.09 ± 0.04 | 0.13 ± 0.05 | 0.13 ± 0.02 | 0.08 ± 0.03 |
| Kidney | 5.85 ± 0.37 | 7.31 ± 0.53 | 3.55 ± 0.44 | 3.21 ± 0.45 | 2.18 ± 0.24 | 2.61 ± 0.51 |
| Lungs | 1.26 ± 0.24 | 1.12 ± 0.26 | 0.13 ± 0.02 | 0.15 ± 0.06 | 0.06 ± 0.00 | 0.07 ± 0.06 |
| Blood | 1.62 ± 0.34 | 1.59 ± 0.29 | 0.12 ± 0.02 | 0.02 ± 0.01 | 0.03 ± 0.01 | 0.00 ± 0.00 |
| Stomach | 0.59 ± 0.32 | 0.52 ± 0.16 | 0.04 ± 0.01 | 0.07 ± 0.03 | 0.03 ± 0.01 | 0.04 ± 0.04 |
| Sm. Int. | 0.55 ± 0.13 | 2.52 ± 3.73 | 0.09 ± 0.01 | 0.17 ± 0.08 | 0.08 ± 0.01 | 0.04 ± 0.01 |
| Lg. Int. | 0.33 ± 0.05 | 0.30 ± 0.07 | 0.33 ± 0.15 | 0.32 ± 0.14 | 0.05 ± 0.01 | 0.07 ± 0.03 |

60 minutes in the presence of 1 µl of RNAse inhibitor (10 U/µl), 4.0 µl of 5× reverse transcriptase buffer (500 mM Tris-HCL, pH 8.2, 200 mM KCl, 50 mM MgCl$_2$, and 2.5 mM spermidine), 1 µl of 100 mM dNTPs, 1 µl of 80 mM sodium pyrophosphate, and 5 U of AMV reverse transcriptase. The RNA-cDNA hybrids were then denatured at 95° C. for 2 minutes. The first strand cDNAs were then used as templates to amplify the VH and Vκ sequences by PCR as described by Orlandi et al., Proc. Natl. Acad. Sci. USA 1989, 86: 3833. The Vκ region was amplified using primers VK1BACK (5'-GAC ATT CAG CTG ACC CAG TCT CCA 3') and IgKC3' (5'-CTC ACT GGA TGG TGG GAA GAT GGA TAC AGT TGG 3'). The VH region was amplified using primers VH1BACK (5' AGG T(C/G)(A/C) A(A/G)C TGC AG(C/G) AGT C(A/T)G G 3') and CH1B. The PCR reaction mixtures containing 10 µl of the first strand cDNA product, 10 µl of 10×PCR buffer (15 mM MgCl$_2$, 500 mM KCl, 100 mM Tris-HCl, pH 8.3, and 0.01% (w/v) gelatin), 1 µM of each primer, 16 µl of dNTPs, and 5 U of AmpliTaq DNA polymerase (Perkin-Elmer, Applied Biosystems Division, Foster City, Calif.) were subjected to 30 cycles of PCR (denaturation at 94° C. for 1 minute, annealing at 45° C. for 1 minute and polymerization at 72° C. for 1 minute for 5 cycles, combined with denaturation at 94° C. for 1 minute, annealing at 55° C. for 1 minute, and polymerization at 72° C. for 1 minute for 25 cycles). The amplified Vk and VH fragments were gel-purified and cloned into the TA cloning vector (Invitrogen) for sequence analyses by the dideoxytermination method. Sequences confirmed to be of immunoglobulin origin were then used to construct chimeric expression vectors using methods described by Leung et al., Hybridoma 1994, 13: 469.

Nucleotide sequencing of multiple clones confirmed the isolation of one Vκ (MU9Vκ1) and one V$_H$ (Mu9 V$_H$) sequence (FIG. 1A) The chimeric Mu-9 (cMu-9-1) constructed from the V$_H$ and Vκ1 cloned by this RT-PCR method did not demonstrate any binding to CSAp antigen, suggesting the possible existence of other "functional" V-region sequence(s) that might be overlooked by RT-PCR cloning procedures.

Example 5

Cloning the Mu-9 Variable Regions by cDNA Library Screening

The cDNA library was constructed from the murine Mu-9 hybridoma in pSPORT vector (Life Technologies). The first strand cDNA was synthesized by pairing poly A mRNA from murine Mu-9 hybridoma with an oligo dT primer-NotI adaptor (Life Technologies). After the second strand synthesis and attachment of SalI adaptors, the cDNA pool was size fractionated through a cDNA size fractionation column. The fractionated cDNA was ligated to pSPORT vector and then transformed into *Escherichia coli* DH5α. The library was plated onto LB-amp (100 µg/ml) plates, colonies transferred to Nytran filters (Schleicher and Schuell, Keene, N.H.), and then amplified on LB-chloramphenicol plates. The amplified colonies were treated successively with 0.5 N NaOH/1.5 M NaCl for 5 minutes; 1 M Tris-HCl, pH 8.0, for 5 minutes; 0.1 M Tris-HCl, pH 7.5/2×SSC for 5 minutes; and finally with 2×SSC for 5-10 minutes. The DNA was immobilized on the filters by baking at 80° C. for 30 minutes. The filters were incubated in prehybridization buffer containing 6×SSC, 5×Denhardt's (0.1% Ficoll, 0.1% polyvinylpyrrolidone, and 0.1% bovine serum albumin), 0.5% SDS, 0.05% sodium pyrophosphate, and 100 µg/ml herring sperm DNA (Life Technologies) for 2 hours at 50° C. Hybridization with the $^{32}$P-labeled probes (MUCH-1 (5'-AGA CTG CAG GAG AGC TGG GAA GGT GTG CAC 3') specific for murine heavy chain and MUCk-1 (5'-GAA GCA CAC GAC TGA GGC ACC TCC AGA TGT 3') specific for murine light chain) at 10$^6$ cpm/ml was done overnight at their respective Tms in the prehybridization solution supplemented with 10% (w/v) dextran sulfate (Pharmacia Biotech, Piscataway, N.J.). The filters were washed four times in 0.2×SSC, 0.1% SDS at 37° C. for 10 minutes, twice at 42° C. for 15 minutes, and once at 50° C. for 15 minutes until the radioactivities on the filters were constant as determined with a Geiger counter. After a final rinse in 2×SSC, the wet filters were exposed to Kodak XAR-5 film (Rochester, N.Y.) at 70° C. The clones that were positive on the first screening were transferred to duplicate LB-amp plates. Duplicate Nytran filters were hybridized to the same probes as described above. Only clones that positively hybridized on both the filters were picked for further screening. For the tertiary screening, the MUCH-1-positive colonies were screened in duplicate with VHCDR3Mu9 (specific for the V$_H$ sequenced cloned by RT-PCR in Example 4) and MUCk-1-positive colonies were screened with VKCDR1Mu9 and VKCDR3Mu9 (specific for the CDR1 and CDR3 coding sequences of Vκ-1 cloned by RT-PCR in Example 4).

All clones (25) that were confirmed to be positive with MUCH-1 were also positive with VHCDR3Mu9, indicating that there was only one type of heavy chain sequence expressed in the hybridoma. Ten clones that positively hybridized with the VHCDR3Mu9 were sequenced and found to be identical to the RT-PCR cloned Mu-9VH, the sequence of which is disclosed in FIG. 1A.

Of the 34 clones that were positive for MUCk-1 in both primary and secondary screenings only 14 hybridized to the Mu9 Vκ1-specific probes, VKCDR1Mu-9 and VKCDR3Mu9. Sequence analyses revealed that these clones were identical to the Mu9Vk1. Of the remaining 20 clones that were negative for the Mu9Vk1-specific probes, 8 were subjected to DNA sequencing. Seven of these clones encoded a kappa light chain sequence with a Vk domain that was different from Mu9Vk1 and designated as Mu9Vk2, the sequence of which is disclosed in FIG. 1B. The chimeric Mu-9 (cMu-9-2) constructed from the V$_H$ and Vk2 and expressed in Sp2/0 cells showed comparable binding affinity to CSAp antigen as that of murine Mu-9 (see Example 8 and 9 for details).

Example 6

Probe Labeling for cDNA Library Screening

Oligonucleotides were synthesized on an automated 392 DNA/RNA synthesized (Applied Biosystems) and then purified on a PD 10 column (Pharmacia Biotech). The purified oligonucleotides were labeled with [γ-$^{32}$P]ATP (Amersham, Arlington Heights, Ill.) using T4 polynucleotide kinase (New England Biolabs, Beverly, Mass.). A typical reaction mixture contained in a final volume of 20 µl was as follows: 50 µmol oligonucleotide, 60 µCi of [γ-$^{32}$P]ATP (6000 Ci/mmol), and 2 µl of 10× kinase buffer (New England Biolabs). The reaction mixture was incubated at 37° C. for 1 hour, and the reaction was terminated with 20 µl of 0.1 M EDTA. The unincorporated [γ-$^{32}$P]ATP was separated from the labeled oligonucleotide on a TE-10 Chromaspin column (Clonetech, Palo Alto, Calif.). The labeled probe was used at $10^6$ cpm/m. for hybridization.

Example 7

Transfection of SP2/0 Cells

The putative $V_K$ and VH sequences for Mu-9 were subcloned into the light (pKh or PKh*) and heavy chain (pG1g) expression vectors, respectively, as describe by Leung et al., supra. pKh* is essentially identical to the pKh, except that is has a XhoI/PacI linker introduced into the BstXI site of the pKh. Because Mu-9 VK2 obtained by cDNA screening contained an internal BstXI site, it was subcloned into pKh*, which could then be linearized with either XhoI or PacI for transfection.

Approximately 10 and 30 µg of linearized light (Mu-9-1 pKh or Mu-9-2pKh*) and heavy (Mu-9pG1g) chain expression vectors were cotransfected into SP2/0 cells by electroporation. Transfected cells were grown in 96-well cell culture plates in complete medium for 2 days and then selected by the addition of hygromycin at a final concentration of 500 U/ml. Typically, the colonies began to emerge 2-3 weeks after electroporation and were assayed for antibody secretion by enzyme-linked immunosorbent assay (ELISA). The chimeric antibodies were purified from the culture supernatant by affinity chromatography on Protein A-Sepharose 4B column. The purified antibodies (5-µg) were analyzed by SDS-PAGE on a 4-20% gradient gel under reducing conditions.

Example 8

Mu-9 Direct Binding Assay

ELISA microtiter plates were coated with a void volume fraction of GW-39 tumor extracts (which contains the CSAp antigen) eluted from a Sepharose 4B-CL column and left overnight at 4° C. The next day, the nonspecific binding was blocked with phosphate-buffered saline (PBS) containing 1% BSA and 0.05% Tween 20. Chimeric antibody supernatant (100 µl) or purified antibody (0-1 µg/ml) was added and incubated at room temperature for 1 hour. Unbound proteins were removed by washing six times with wash buffer (PBS containing 0.05% Tween 20). Purified murine Mu-9 protein was used as the standard. The bound antibodies were allowed to react with peroxidase-conjugated goat anti-human IgG, Fc fragment-specific (Jackson ImmunoResearch, West Grove Pa.) and peroxidase conjugated goat anti-mouse IgG, Fc fragment-specific antibodies (Jackson ImmunoResearch). After washing the plate six times with wash buffer, 100 µl of OPD substrate solution (10 mg of orthophenylenediamine dihydrochloride (Sigma, St. Louis, Mo.) in 25 ml of 0.32×PBS and 0.12% $H_2O_2$) was added to each well. The color was developed in the dark for 1 hour, the reaction was stopped with 50 µl of 4N $H_2SO_4$, and the absorbance at 490 nm was measured in a Dynatech plate reader (Dynatech Labs, Sussex, UK).

Direct binding of a cMu-9 (cMu-9-2) to CSAp antigen occurred, as shown in FIG. 5(a). The binding profile of cMu-9-2 was virtually superimposable on that of the murine Mu-9. These data demonstrated that the immunoreactivity of cMu-9-2 is comparable to that of murine Mu-9. The DNA and amino acid sequences of the functional cMu-9 VK and $V_H$ are shown in FIGS. 2A and 2B, respectively.

Example 9

Competitive Binding Assay

Murine Mu-9 IgG was conjugated with horseradish peroxidase (HRP) (Sigma). The peroxidase-conjugated Mu-9 was first tested for binding on microwells coated with CSAp antigen, and the optimum concentration was determined to be 0.2 µg/ml. Peroxidase-conjugated Mu-9 was mixed with various concentrations of either murine or chimeric Mu-9 (0-50 µg/ml) before addition to the antigen-coated wells. Binding of the peroxidase-conjugated Mu-9 to the antigen in the presence of the competing antibodies was measured at 490 nm after the addition of the substrate as described earlier.

FIG. 5(b) displays the results of the competitive binding assay. Murine Mu-9 and cMu-9-2 competed equally well with the binding of HRP-conjugated Mu-9 to the CSAp antigen. These data demonstrated that the immunoreactivity of cMu-9-2 is comparable to that of murine Mu-9.

Example 10

Choice of Human Frameworks and Sequence Design for the Humanization of Mu-9 Monoclonal Antibody By comparing the variable (V) region framework (FR) sequences of Mu9 to that of human antibodies in the Kabat data base, the FRs of Mu9VH and VK were found to exhibit the highest degree of sequence homology to that of the human antibodies, EU VH and WOL VK, respectively. In FIGS. 3A and 3B, the amino acid sequences of the Mu9VH and VK Abs are aligned and compared with the corresponding human sequences. Therefore, the FRs of EU VH and WOL VK were selected as the human frameworks onto which the CDRs for Mu-9VH and VK were grafted, respectively. The FR4 sequence of NEWM, however, rather than that of EU, was used for the humanization of Mu9 heavy chain (FIG. 3A). A few amino acid residues in Mu9 FRs that are close to the putative CDRs were maintained in hMu9 based on the guideline described previously (Qu et al., Clin. Cancer Rec. 5:3095s-3100s (1999)). These residues are L37, V58 and Q100 of VK (FIG. 3B) and Y27, T30, K38, R40, I48, K66, A67, K74, T93, R94 and G103 of VH (FIG. 3A). The gene sequences of hMu9VH and VK were then designed and shown with the amino acid sequences in FIGS. 4A and 4B, respectively.

Example 11

PCR/Gene Synthesis of the Humanized V Genes

The strategy as described by Leung et al. (Leung et al., 1994)) was used to construct the designed VK and VH genes for hMu-9 using a combination of long oligonucleotide syntheses and PCR. Each variable chain was constructed in two parts, a 5'- and 3'-half, designated as "A" and "B," respectively. Each half was produced by PCR amplification of a single strand synthetic oligonucleotide template with two short flanking primers, using Taq polymerase. The amplified fragments were first cloned into the pCR4 TA cloning vector from Invitrogen (Carlsbad, Calif.) and subjected to DNA sequencing. The templates and primer pairs are listed as follows:

| Template | Primers | PCR product |
|---|---|---|
| Oligo G | Oligo 14/Oligo 15 | hMu9VHA |
| Oligo H | Oligo 16/Oligo 17 | hMu9VHB |
| Oligo J | Oligo 18/Oligo 19 | hMu9VkA |
| Oligo K | Oligo 20/Oligo 21 | hMu9VkB |

Heavy Chain

For constructing the full-length DNA of the hMu9V$_H$ sequence, Oligo G (102 mer) and H (179 mer) were synthesized on an automated RNA/DNA synthesizer (Applied Biosystems). Oligo G sequence represents the minus strand of hMu9VH domain complementary to nt 19 to 120:

5'-AGGTCTCTGT TTTACCCAGG TAATAACATA CTCAGTGAAG

GTGTATCCAG AAGCCTTGCA GGAGACCTTC ACTGAGCTCC

CAGGCTTTTT CACCTCAGCT CC-3'

Oligo H sequence represents the nt 147 to 325 of hMu9VH domain:

5'-GATTTATCCT GGAAGTGGTA GTACTTCCTA CAATGAAAAG

TTCAAGGGCA AGGCCACAAT CACTGCTGAC AAATCCACTA

ACACAGCCTA CATGGAGCTC AGCAGCCTGA GATCTGAGGA

CACTGCGTTC TATTTCTGTA CAAGAGAGGA TCTTGGGGGC

CAAGGGTCTC TGGTCACCG-3'

Oligo G and H were cleaved from the support and deprotected by treatment with concentrated ammonium hydroxide. After samples were vacuum-tried and resuspended in 100 µl of water, incomplete oligomers (less than 100-mer) were removed by centrifugation through a ChromaSpin-100 column (Clontech, Palo Alto, Calif.). All flanking primers were prepared similarly, except ChromaSpin-30 columns were used to remove synthesis by-products. 1 µl of ChromaSpin column purified Oligo G was PCR amplified in a reaction volume of 100 µl containing 10 µl of 10×PCR buffer [500 mM KCl, 100 mM Tris-HCl (pH 8.3), 15 mM MgCl$_2$, and 0.01% (w/v) gelatin] (Perkin Elmer Cetus, Norwalk, Conn.), 250 µM of each dNTP, 200 nM of Oligo14 (5'-GTGCAGCTGC AGCAGTCAGG AGCTGAGGTG-3') and Oligo 15 (5'-ACTCTAGACC CTGTCCAGGT CTCTGTTTTA CCCAG-GTAAT AACATA-3'), and 5 units of Taq DNA polymerase (Perkin Elmer Cetus). This reaction mixture was subjected to 30 cycles of PCR reaction consisting of denaturation at 94° C. for 1 min, annealing at 50° C. for 1.5 min, and polymerization at 72° C. for 1.5 min. Oligo H was PCR-amplified by the primer pair Oligo 16 (5'-GGTCTAGAGT GGATTGGAGA GATTTATCCT GGAAGTGGTA GTACTT-3') and Oligo 17 (5'-TGAAGAGACG GTGACCAGAG ACCCTTGGCC CCCAAGATCC TCTCTTGTAC AGAAATAGAA CGC-3') under similar condition. Resulting PCR fragments, VHA and VHB were purified on 2% agarose (BioRad, Richmond, Calif.). Unique restriction sites were designed at the ends of each fragment to facilitate joining through DNA ligation. The amplified VHA fragment contained a PstI restriction site, CTGCAG, at its 5'-end and a XbaI restriction site, TCTAGA, at the 3'-end. The amplified VHB fragment contained a XbaI restriction site at its 5'-end and a BstEII restriction site, GGT-CACC, at the 3'-end. Assembly of the full-length VH chain was accomplished by restriction enzyme digestion of each fragment with the appropriate 5'- and 3'-enzymes and ligation into the VHpBS vector (Leung et al., Hybridoma, 13:469 (1994)) previously digested with PstI and BstEII. The resulting ligated product contains the A fragment ligated to the PstI site, the B fragment to the BstEII site, and the A and B fragments joined together at the XbaI site (FIG. 4A). Upon confirmation of a correct open reading frame by DNA sequencing, the intact VH gene sequence along with the promoter and the secretion signal peptide coding sequence was removed from VHpBS as a HindIII to BamHI fragment and ligated into the VHpG1g expression vector (Leung et al., Hybridoma, 13:469 (1994)), resulting in hMu9VHpG1g.

Light Chain

For the construction of Vκ, the long oligonucleotide templates synthesized were Oligo J (130 mer) representing the minus strand of hMu9Vκ domain complementary to nt 21 to 150:

5'-CCTTGGAGCC TGGCCTGGTT TCTGCAGGTA CCATTCTAAA

TAGGTGTTGC CATTACTATG CACAATGCTC TGACTAGACC

TGCAAGACAG AGTGGCTCGC TCTCCAGGAC TGAGGGACAG

GGTGCCTGGG-3' and Oligo K (150 mer) representing the nt 151 to 300 of hMu9Vκ domain:

5'-CTCCTGATCT ACAAAGTTTC CAACCGATTT TCCGGAGTCC

CAGACAGGTT CAGTGGCTCT GGATCAGGGA CAGATTTCAC

ACTTACTATC AGCAGACTGG AGCCTGAGGA TTTTGCTGTG

TATTACTGCT TTCAAGGTTC ACGTGTTCCG-3'

These oligos were PCR-amplified by their respective primer pairs as listed:

Oligo 18
5'-GATATCCAGC TGACCCAATC CCCAGGCACC CTGTCCCTCA

GTCCTGGAG-3'

Oligo 19
5'-AGATCAGGAG CCTTGGAGCC TGGCCTGGTT TCTGCA-3'

Oligo 20
5'-TACCTGCAGA AACCAGGCCA GGCTCCAAGG CTCCTGATCT

ACAAAGTTTC CAACCG-3'

Oligo 21
5'-TTAATCTCCA CCTTGGTCCC CCCTCCGAAC GTGTACGGAA

CACGTGAACC TTGAAAGCAG TAATACA-3'

The same construction method as done for VH was carried out for Vκ, with the following modifications: the 5'-end restriction site of the A fragments was PvuII (CAGCTG) and the 3'-end restriction site of B fragments was BglII (AG-ATCT). These fragments were joined together upon ligation into the VKpBR vector at a common PstI site (CTGCAG), resulting in full-length Vκ sequence (FIG. 4B) and confirmed by DNA sequencing. The assembled Vκ gene was subcloned as HindIII-BamHI restriction fragment into the light expression vector, resulting in hMu9VKpKh.

Example 12

Transfection, Expression and Binding Activity Assays for hMu9

The methods for expression and binding activity assays for hMu9 were same as described for cMu9. Approximately 10 and 30 μg of linearized hMu9VkpKh and hMu9VHpG1g were co-transfected into SP2/0 cells by electroporation. Transfected cells were grown in 96-well cell culture plates in complete medium for 2 days and then selected by the addition of hygromycin at a final concentration of 500 U/ml. Typically, the colonies began to emerge 2-3 weeks after electroporation and were assayed for antibody secretion by enzyme-linked immunosorbent assay (ELISA). The chimeric antibodies were purified from the culture supernatant by affinity chromatography on Protein A-Sepharose 4B column. The purified antibodies (5 μg) were analyzed by SDS-PAGE on a 4-20% gradient gel under reducing conditions.

Direct binding assay showed that the purified hMu-9 bound to CSAp antigen. The binding affinity of hMu-9 was compared in a competitive binding assay as described in Example 6. FIG. 6 displays the results of the competitive binding assay. hMu-9 or murine Mu-9 competed equally well with the binding of HRP-conjugated Mu-9 to the CSAp antigen. These data demonstrated that the immunoreactivity of hMu-9 is comparable to that of murine Mu-9.

Example 13

Therapy of a Patient with $^{90}$Y-Labeled Humanized Mu-9 Antibody

A 62-year-old man, with a history of Dukes' C rectal carcinoma that was resected 3 years earlier, at which time radiation therapy followed by 5-fluorouracil/folinic acid chemotherapy were given, began showing a rise in his plasma CEA titer over the last 6 months, reaching a level of 30 ng/mL. The patient, who was seeing his oncologist twice annually, learned of this result and underwent various diagnostic procedures because of a suspected recurrence. It was found, by computed tomorgraphy, that there were two metastases present in his liver, one being 3 cm in diameter in his right lobe, and the other being somewhat smaller in the left lobe, close to the interlobe ligament. The patient opted not to undergo chemotherapy, and was then given a dose of 25 mCi $^{90}$Y conjugated to the humanized Mu-9 antibody, given at a protein dose of 50 mg by intravenous infusion over a period of 2 hours. This therapy was then repeated two months later. The patients had a drop of his white blood cells and platelets, measured 2-4 weeks after the last therapy infusion, but recuperated at the 8-week post-therapy evaluation. The computed tomography findings at 3 months post-therapy revealed 40% shrinkage of the major tumor metastasis of the right liver lobe, and a lesser reduction in the left-lobe tumor. At this time, the patient's blood CEA dropped to 15 ng/mL. At the 6-month follow-up, his tumor lesions had been reduced, in two-diameter CT-measurements, by about 70 percent, his plasma CEA was at 8 ng/mL, and his general condition was fine, with no apparent toxicity or adverse events related to the therapy. The patient is now 9 months post-therapy with no change in the size of his liver metastases and a stable serum CEA titer at about 5-8 ng/mL. He is being followed every 3 months, so that if the disease begins to grow, he is scheduled to receive another course of this radioimmunotherapy, followed by a course of naked Mu-9 antibody, at a weekly dose of 300 mg/m$^2$, once weekly for 6 weeks, concomitantly with a therapy course of irinotecan (CPT-11).

VII. REFERENCES

All references cited, as well as references cited by the references cited herein, are hereby incorporated herein by reference in their entireties.

Additional references of interest, as well as references cited therein, include the following, and are hereby incorporated herein by reference in their entireties:

Bamias, A., and Epenetos, A. A. Two-step strategies for the diagnosis and treatment of cancer with bioconjugates. *Antibody, Immunoconjugates, Radiopharm.* 1992; 5: 385-395.

Barbet, J., Peltier, P., Bardet, S., Vuillez, J P., Bachelot, I., Denet, S., Olivier, P., Lecia, F., Corcuff, B., Huglo, D., Proye, C., Rouvier, E., Meyer, P., Chatal, J. F. Radioimmunodetection of medullary thyroid carcinoma using indium-111 bivalent hapten and anti-CEA×anti-DTPA-indium bispecifc antibody. *J. Nucl. Med.* 1998; 39:1172-1178.

Bos, E S., Kuijpers, W H A., Meesters-Winters, M., Pham, D T., deHaan, A S., van Doormalen, Am., Kasperson, F. M., vanBoeckel, C A A and Gouegeon-Bertrand, F. In vitro evaluation of DNA-DNA hybridization as a two-step approach in radioimmunotherapy of cancer. *Cancer Res.* 1994; 54:3479-3486.

Carr et al., WO00/34317.

Di Carlo, A., Mariano, A., D'Alessandro, V., Belli, G., Romano, G., Macchia, V. Evaluation of epidermal growth factor receptor, carcinoembryonic antigen and Lewis carbohydrate antigens in human colorectal and liver neoplasias. *Oncol. Rep.* 2001; 8:387-392.

Epstein et al. U.S. Pat. Nos. 5,019,368; 5,882,626; 6,017,514; and the patents and references cited therein.

Gautherot, E., Bouhou, J., LeDoussal, J-M., Manetti, C., Martin, M., Rouvier, E., Barbet, J. Therapy for colon carcinoma xenografts with bi-specific antibody-targeted, iodine-131-labeled bivalent hapten. *Cancer* suppl. 1997; 80: 2618-2623.

Gautherot, E., Bouhou, J., Loucif, E., Manetti, C., Martin, M., LeDoussal, J. M., Rouvier, E., Barbet, J. Radioimmunotherapy of LS174T colon carcinoma in nude mice using an iodine-131-labeled bivalent hapten combined with an anti-CEA×anti-indium-DTPA bi-specific antibody. *J. Nucl. Med.* Suppl. 1997; 38: 7p.

Goodwin, D. A., Meares, C F., McCall, M J., McTigue, M., Chaovapong, W. Pre-targeted immunoscintigraphy of murine tumors with indium-111-labeled bifunctional haptens. *J. Nucl. Med.* 1988; 29:226-234.

Greenwood, F. C. and Hunter, W. M. The preparation of I-131 labeled human growth hormone of high specific radioactivity. *Biochem.* 1963; 89:114-123.

Hawkins, G. A., McCabe, R. P., Kim, C.-H., Subramanian, R., Bredehorst, R., McCullers, G. A., Vogel, C.-W., Harma, M. G. Jr., and Pomata, N. Delivery of radionuclides to pretargeted monoclonal antibodies using dihydrofolate reductase and methotrexate in an affinity system. *Cancer Res.* 1993; 53: 2368-2373. Infusa, H., Adachi, T., Kiyokawa, T., Nakatani, Y., et al., Ley glycolipid-recognizing monoclonal antibody inhibits procoagulant activity and metastasis of uman adenocarcinoma. *Int. J. Oncol.,* 2001; 19:941-946.

Koda, K., Glassy, M. C., McKnight, M. E., Yasutomi, J., Saito, N., Dan, M., Nakajima, N. Immunotherapy for recurrent colorectal cancers with human monoclonal antibody SK-1. *Anticancer Res.* 2001; 21:621-627.

Kranenborg, M.h., Boerman, O. C., Oosterwijk-Wakka, j., weijert, M., Corstens, F., Oosterwijk, E. Development and characterization of anti-renal cell carcinoma×antichelate bi-specific monoclonal antibodies for two-phase targeting of renal cell carcinoma. *Cancer Res.* (suppl) 1995; 55: 5864s-5867s.

Losman M. J., Qu Z., Krishnan I. S., Wang J., Hansen H. J., Goldenberg D. M., Leung S. O. *Clin. Cancer Res.* 1999; 5(10 Suppl.):3101s-3105s.

Maeta, M. Saito, H. Oka, S., Tsujitani, S., Ikeguchi, M., Kaibara, N. Mutated p53 in tumors, mutant p53 and p53-specific antibodies in the circulation in patients with gastric cancer. *J. Exp. Clin. Cancer Res.* 2000; 19:489-95.

Penefsky, H. S. A centrifuged column procedure for the measurement of ligand binding by beef heart F1. Part G. *Methods Enzymol.* 1979; 56:527-530.

Ritter, G., Cohen, L. S., Williams, C., Jr., Richards, E. C., Old, L. J., Welt S. Serological analysis of human anti-human antibody responses in colon cancer patients treated with repeated doses of humanized monoclonal antibody A33. *Cancer Res.* 2001; 61:6851-6859.

Schuhmacher, J., Klivenyi, G., Matys, R., Stadler, M., Regiert, T., Hauser, H., Doll, J., Maier-Borst, W., Zoller, M. Multistep tumor targeting in nude mice using bi-specific antibodies and a gallium chelate suitable for immunocintigraphy with positron emission tomography. *Cancer Res.* 1995; 55, 115-123.

Schwartzberg, L. S. Clinical experience with edrecolomab: a monoclonal antibody therapy for colorectal carcinoma. *Crit. Rev. Oncol. Hematol.* 2001; 40:17-24.

Sharkey, R M., Karacay, Griffiths, G L., Behr, T M., Blumenthal, R D., Mattes, M J., Hansen, H J., Goldenberg. Development of a streptavidin-anti-carcinoembryonic antigen antibody, radiolabeled biotin pretargeting method for radioimmunotherapy of colorectal cancer. Studies in a human colon cancer xenograft model. *Bioconjugate Chem* 1997; 8:595-604.

Staib, L., Birebent, B., Somasundaram, R., Purev, E., Braumuller, H., et al. Immunogenicity of recombinant GA733-2E antigen (CO17-1A, EGP, Dsi4, KSA, Ep-CAM) in gastro-intestinal carcinoma patients. *Int. J. Cancer* 2001; 92:79-87.

Stickney, D R., Anderson, L D., Slater, J B., Ahlem, C N., Kirk, G A., Schweighardt, S A and Frincke, J M. Bifunctional antibody: a binary radiopharmaceutical delivery system for imaging colorectal carcinoma *Cancer Res.* 1991; 51: 6650-6655.

Thorpe et al., U.S. Pat. Nos. 6,342,221; 6,004,554; and patents and references cited therein.

Todryk, S. M., Turr, A. L., Green, M. H., Smallwood, J. A., Halanek, N., Dalgleish, A. G., Glennie, M. J. CD40 ligation for immunotherapy of solid tumours. *J. Immunol Methods* 2001; 248:139-147.

Tordsson, J., Lavasani, S., Ohlsson, L., Karlstrom, P., Svedberg, H., Abrahmsen, L., Brodin, T. A3—a novel colon and pancreatic cancer reactive antibody from a primate phage library selected using intact tumour cells. *Int. J. Cancer* 2000; 87:559-568.

Turner, J. G., Rakhmilevich, A. L. Burdelya, L., Neal., Z., Imboden, M., Sondel, P. M., Yu, H. Anti-CD40 antibody induces antitumor and antimetastatic effects: the role of NK cells. *J. Immunol.* 2001; 166:89-94.

What is claimed is:

1. A DNA sequence comprising a nucleic acid encoding an anti-CSAp antibody or an immunoreactive fragment thereof, wherein the anti-CSAP antibody or fragment thereof is a humanized or chimeric Mu-9 antibody fragment that comprises the light chain CDR sequences CDR1 (RSSQSIVHSNGNTYLE, SEQ ID NO:1), CDR2 (KVSNRFS, SEQ ID NO:2) and CDR3 (FQGSRVPYT, SEQ ID NO:3) and the heavy chain CDR sequences CDR1 (EYVIT, SEQ ID NO:4), CDR2 (EIYPGSGSTSYNEKFK, SEQ ID NO:5) and CDR3 (EDL).

2. A method of treating cancer comprising:
   a. obtaining a DNA sequence according to claim 1;
   b. expressing a humanized or chimeric Mu-9 antibody or fragment thereof from the DNA sequence, wherein said antibody or fragment thereof comprises the light chain CDR sequences CDR1 (RSSQSIVHSNGNTYLE, SEQ ID NO:1), CDR2 (KVSNRFS, SEQ ID NO:2) and CDR3 (FQGSRVPYT, SEQ ID NO:3) and the heavy chain CDR sequences CDR1 (EYVIT, SEQ ID NO:4), CDR2 (EIYPGSGSTSYNEKFK, SEQ ID NO:5) and CDR3 (EDL); and
   c. administering the humanized or chimeric Mu-9 antibody or fragment thereof to a subject with a cancer that expresses CSAp antigen.

3. A method of treating cancer comprising:
   administering a chimeric or humanized Mu-9 anti-CSAp antibody or fragment thereof to a subject with a cancer that expresses CSAp antigen, wherein said antibody or fragment thereof comprises the light chain CDR sequences CDR1 (RSSQSIVHSNGNTYLE, SEQ ID NO:1), CDR2 (KVSNRFS, SEQ ID NO:2) and CDR3 (FQGSRVPYT, SEQ ID NO:3) and the heavy chain CDR sequences CDR1 (EYVIT, SEQ ID NO:4), CDR2 (EIYPGSGSTSYNEKFK, SEQ ID NO:5) and CDR3 (EDL).

4. The method of claim 3, wherein the chimeric or humanized Mu-9 anti-CSAp antibody or fragment is a fusion protein.

5. The method of claim 3, wherein the humanized Mu-9 antibody or fragment thereof comprises the amino acid sequences of hMu-9VH (SEQ ID NO:38) and hMu-9VK (SEQ ID NO:40).

6. The method of claim 5, wherein the humanized Mu-9 antibody or fragment thereof comprises an asparagine residue in place of the arginine residue at position 18 of the hMu-9VK sequence (SEQ ID NO:40).

7. The method of claim 3, wherein the chimeric Mu-9 antibody or fragment thereof comprises the amino acid sequences of cMu-9VH (SEQ ID NO:34) and cMU-9Vk (SEQ ID NO:36).

8. The method of claim 3, wherein the chimeric or humanized Mu-9 anti-CSAp antibody or fragment thereof is a naked antibody or fragment.

9. The method of claim 8, wherein the naked chimeric or humanized Mu-9 anti-CSAp antibody or fragment thereof is administered to a subject in combination with radiation therapy, chemotherapy, surgery or a non-CSAp antibody or fragment thereof.

10. The method of claim 3, wherein the chimeric or humanized Mu-9 anti-CSAp antibody or fragment thereof is conjugated to at least one therapeutic agent.

11. The method of claim 10, wherein the at least one therapeutic agent is selected from the group consisting of a radionuclide, boron atoms, gadolinium atoms, uranium atoms, an immunomodulator, a cytokine, a hormone, a hormone antagonist, an enzyme, an enzyme inhibitor, a photoactive therapeutic agent, a drug, a cytotoxic agent, a toxin, an angiogenesis inhibitor and a second antibody or fragment thereof.

12. The method of claim 11, wherein the radionuclide has an energy between 20 and 10,000 keV.

13. The method of claim 11, wherein the radionuclide is selected from the group consisting of Ac-225, Ag-111, As-77, At-211, At-217, Au-198, Au-199, Bi-211, Bi-212, Bi-213, Br-80m, Co-58, Cu-64, Cu-67, Dy-152, Er-169, Fe-59, Fm-255, Fr-221, Ga-67, Ho-161, Ho-166, I-125, I-131, In-111, Ir-192, Ir-194, Lu-177, Mo-99, Os-189m, P-32, P-33, Pb-211, Pb-212 Pd-109, Pm-149, Po-215, Pr-142, Pr-143, Pt-109, Ra-223, Re-186, Re-188, Re-189, Rh-103m, Rh-105, Rn-219, Sb-119, Sc-47, Se-75, Sm-153, Sr-89, Tc-99m, Th-161 and Y-90.

14. The method of claim 11, wherein the angiogenesis inhibitor is selected from the group consisting of angiostatin, endostatin, vasculostatin, canstatin and maspin.

15. The method of claim 11, wherein the drug is selected from the group consisting of adriamycin, dactinomycin, mitomycin, carminomycin, daunomycin, doxorubicin, gemcitabine, tamoxifen, taxol, taxane, taxotere, vincristine, vinblastine, vinorelbine, etoposide (VP-16), 5-fluorouracil (5FU), CPT-11, cytosine arabinoside, cyclophosphamide, thiotepa, methotrexate, camptothecin, actinomycin-D, mitomycin C, cisplatin (CDDP), oxaliplatin, aminopterin, combretastatin, neomycin, podophyllotoxin, TNF-α, a calcium ionophore, a calcium-flux inducing agent, amethopterin, anthracycline, vinca alkaloid, demecolcine and mithramycin.

16. The method of claim 11, wherein the toxin is selected from the group consisting of ricin, abrin, ribonuclease, alpha toxin, saporin, DNase I, ribonuclease, *Staphylococcal* enterotoxin-A, pokeweed antiviral protein, gelonin, diphtheria toxin, *Pseudomonas* exotoxin and *Pseudomonas* endotoxin.

17. The method of claim 11, wherein the chimeric or humanized Mu-9 anti-CSAp antibody or fragment thereof is conjugated to a second antibody or fragment thereof to form a bispecific antibody or bispecific antibody fragment.

18. The method of claim 11, wherein the chimeric or humanized Mu-9 anti-CSAp antibody or fragment thereof is conjugated to a second chimeric or humanized anti-CSAp antibody or fragment thereof.

19. The method of claim 17, wherein the second antibody or fragment thereof binds to a hapten on a targetable conjugate.

20. The method of claim 17, wherein the second antibody or fragment thereof binds to an antigen selected from the group consisting of CEA, EGP-1, EGP-2, MUC-1, MUC-2, MUC-3, MUC-4, PAM-4, KC4, TAG-72, EGFR, HER2/neu, BrE3, Le-Y, A3, KS-1, CD40, VEGF and the antigen bound by the antibody A33.

21. The method of claim 19, further comprising:
   a. allowing a sufficient amount of time after administration of the bispecific antibody for bispecific antibody that is not bound to the cancer to clear from circulation;
   b. administering to the subject a targetable conjugate comprising at least one hapten that binds to the second antibody or fragment thereof and at least one therapeutic agent.

22. The method of claim 21, further comprising:
   c. prior to the administration of said targetable conjugate, administering to the subject a clearing composition to clear bispecific antibody that is not bound to the cancer from circulation.

23. The method of claim 3, wherein the cancer is a carcinoma, a gastrointestinal cancer, a colorectal cancer, a pancreatic cancer or an ovarian cancer.

\* \* \* \* \*

```
                       SEQUENCE LISTING

<160> NUMBER OF SEQ ID NOS: 41

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Ser Ser Gln Ser Ile Val His Ser Asn Gly Asn Thr Tyr Leu Glu
1               5                   10                  15

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Val Ser Asn Arg Phe Ser
1               5

<210> SEQ ID NO 3
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 3

Phe Gln Gly Ser Arg Val Pro Tyr Thr
  1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Glu Tyr Val Ile Thr
  1               5

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Glu Ile Tyr Pro Gly Ser Gly Ser Thr Ser Tyr Asn Glu Lys Phe Lys
  1               5                  10                  15

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Phe Lys Tyr Lys
  1

<210> SEQ ID NO 7
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 7
acagtcactg agctgg                                                      16

<210> SEQ ID NO 8
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 8
gccggatcct gactggatgg tgggaagatg gataca                                36

<210> SEQ ID NO 9
<211> LENGTH: 24
<212> TYPE: DNA
<213> ORGANISM: Artificial Sequence
```

```
<220> FEATURE:
<223> OTHER INFORMATION: Description of Artificial Sequence: Primer

<400> SEQUENCE: 9
gacattcagc tgacccagtc tcca                                          24

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 10
ctcactggat ggtgggaaga tggatacagt tgg                                33

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 11
aggtsmarct gcagsagtcw gg                                            22

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Probe

<400> SEQUENCE: 12
agactgcagg agagctggga aggtgtgcac                                    30

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Probe

<400> SEQUENCE: 13
gaagcacacg actgaggcac ctccagatgt                                    30

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Gly-Ser
      linker

<400> SEQUENCE: 14

Gly Gly Gly Gly Ser Gly Gly Gly Gly Ser Gly Gly Gly Gly Ser
 1               5                  10                  15

<210> SEQ ID NO 15
<211> LENGTH: 109
<212> TYPE: PRT
<213> ORGANISM: Homo sapiens

<400> SEQUENCE: 15

Glu Ile Val Leu Thr Gln Ser Pro Gly Thr Leu Ser Leu Ser Pro Gly
 1               5                  10                  15
```

```
Glu Arg Ala Thr Leu Ser Cys Arg Ala Ser Gln Ser Val Ser Ser Gly
             20                  25                  30

Tyr Leu Gly Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Leu Gly
             85                  90                  95

Arg Thr Phe Gly Gln Gly Thr Lys Val Glu Ile Lys Arg
            100                 105

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Thiosemicarbazonylglyoxylcysteine (Tscg-Cys)

<400> SEQUENCE: 16

Lys Tyr Lys Lys Xaa
 1               5

<210> SEQ ID NO 17
<211> LENGTH: 102
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
aggtctctgt tttacccagg taataacata ctcagtgaag gtgtatccag aagccttgca      60
ggagaccttc actgagctcc caggcttttt cacctcagct cc                        102

<210> SEQ ID NO 18
<211> LENGTH: 179
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gatttatcct ggaagtggta gtacttccta caatgaaaag ttcaagggca aggccacaat      60
cactgctgac aaatccacta acacagccta catggagctc agcagcctga gatctgagga    120
cactgcgttc tatttctgta caagagagga tcttgggggc caagggtctc tggtcaccg     179

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
```
gtgcagctgc agcagtcagg agctgaggtg                                30

<210> SEQ ID NO 20
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
actctagacc ctgtccaggt ctctgtttta cccaggtaat aacata            46

<210> SEQ ID NO 21
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ggtctagagt ggattggaga gatttatcct ggaagtggta gtactt            46

<210> SEQ ID NO 22
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
tgaagagacg gtgaccagag acccttggcc cccaagatcc tctcttgtac agaaatagaa   60
cgc                                                                63

<210> SEQ ID NO 23
<211> LENGTH: 130
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ccttggagcc tggcctggtt tctgcaggta ccattctaaa taggtgttgc cattactatg   60
cacaatgctc tgactagacc tgcaagacag agtggctcgc tctccaggac tgagggacag  120
ggtgcctggg                                                         130

<210> SEQ ID NO 24
<211> LENGTH: 150
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ctcctgatct acaaagtttc caaccgattt tccggagtcc cagacaggtt cagtggctct   60
ggatcaggga cagatttcac acttactatc agcagactgg agcctgagga ttttgctgtg  120
tattactgct ttcaaggttc acgtgttccg                                   150

<210> SEQ ID NO 25
<211> LENGTH: 49
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 25
gatatccagc tgacccaatc cccaggcacc ctgtccctca gtcctggag        49

<210> SEQ ID NO 26
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 26
agatcaggag ccttggagcc tggcctggtt tctgca        36

<210> SEQ ID NO 27
<211> LENGTH: 56
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 27
tacctgcaga aaccaggcca ggctccaagg ctcctgatct acaaagtttc caaccg        56

<210> SEQ ID NO 28
<211> LENGTH: 67
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 28
ttaatctcca ccttggtccc ccctccgaac gtgtacggaa cacgtgaacc ttgaaagcag        60
taataca        67

<210> SEQ ID NO 29
<211> LENGTH: 335
<212> TYPE: DNA
<213> ORGANISM: Murine sp.
<220> FEATURE:
<221> NAME/KEY: CDS
<222> LOCATION: (3)..(335)

<400> SEQUENCE: 29

```
ag gtg cag ctg cag gag tca gga cct gag ctg gtg aag cct ggg gct        47
   Val Gln Leu Gln Glu Ser Gly Pro Glu Leu Val Lys Pro Gly Ala
   1               5                  10                  15 tca gtg aag atg tcc tgc agg gct tct gga tac acc ttc act gag tat        95
Ser Val Lys Met Ser Cys Arg Ala Ser Gly Tyr Thr Phe Thr Glu Tyr
                20                  25                  30 gtt att acc tgg gta aaa cag aga act gga cag ggc ctt gag tgg att       143
Val Ile Thr Trp Val Lys Gln Arg Thr Gly Gln Gly Leu Glu Trp Ile
            35                  40                  45 gga gag att tat cct gga agt ggt agt act tcc tac aat gaa aag ttc       191
Gly Glu Ile Tyr Pro Gly Ser Gly Ser Thr Ser Tyr Asn Glu Lys Phe
        50                  55                  60
```

```
aag ggc aag gcc aca ctg act gca gac aaa tcc tcc aac aca gcc tac      239
Lys Gly Lys Ala Thr Leu Thr Ala Asp Lys Ser Ser Asn Thr Ala Tyr
 65                  70                  75 atg cac ctc agc agc ctg aca tct gag gac tct gcg gtc tat ttc tgt      287
Met His Leu Ser Ser Leu Thr Ser Glu Asp Ser Ala Val Tyr Phe Cys
 80                  85                  90                  95 aca aga gag gat ctt ggg ggc caa ggg act ctg gtc act gtc tct tca      335
Thr Arg Glu Asp Leu Gly Gly Gln Gly Thr Leu Val Thr Val Ser Ser
                100                 105                 110

<210> SEQ ID NO 30
<211> LENGTH: 111
<212> TYPE: PRT
<213> ORGANISM: Murine sp.

<400> SEQUENCE: 30

Val Gln Leu Gln Glu Ser Gly Pro Glu Leu Val Lys Pro Gly Ala Ser
 1               5                  10                  15

Val Lys Met Ser Cys Arg Ala Ser Gly Tyr Thr Phe Thr Glu Tyr Val
                20                  25                  30

Ile Thr Trp Val Lys Gln Arg Thr Gly Gln Gly Leu Glu Trp Ile Gly
            35                  40                  45

Glu Ile Tyr Pro Gly Ser Gly Ser Thr Ser Tyr Asn Glu Lys Phe Lys
        50                  55                  60

Gly Lys Ala Thr Leu Thr Ala Asp Lys Ser Ser Asn Thr Ala Tyr Met
 65                  70                  75                  80

His Leu Ser Ser Leu Thr Ser Glu Asp Ser Ala Val Tyr Phe Cys Thr
                85                  90                  95

Arg Glu Asp Leu Gly Gly Gln Gly Thr Leu Val Thr Val Ser Ser
                100                 105                 110

<210> SEQ ID NO 31
<211> LENGTH: 336
<212> TYPE: DNA
<213> ORGANISM: Murine sp.
<220> FEATURE:
<221> NAME/KEY: CDS
<222> LOCATION: (1)..(336)

<400> SEQUENCE: 31 gct gtt ttg atg acc caa act cca ctc tcc ctg cct gtc agt ctt gga       48
Ala Val Leu Met Thr Gln Thr Pro Leu Ser Leu Pro Val Ser Leu Gly
 1               5                  10                  15 gat caa gcc tcc atc tct tgc aga tct agt cag agc att gtc cat agt       96
Asp Gln Ala Ser Ile Ser Cys Arg Ser Ser Gln Ser Ile Val His Ser
                20                  25                  30 aat ggc aac acc tat tta gaa tgg tac ctg cag aaa cca ggc cag tct      144
Asn Gly Asn Thr Tyr Leu Glu Trp Tyr Leu Gln Lys Pro Gly Gln Ser
            35                  40                  45 cca aag ctc ctg atc tac aaa gtt tcc aac cga ttt tct ggg gtc cca      192
Pro Lys Leu Leu Ile Tyr Lys Val Ser Asn Arg Phe Ser Gly Val Pro
        50                  55                  60 gac agg ttc agt ggc act gga tca ggg aca gat ttc aca gtc agg atc      240
Asp Arg Phe Ser Gly Thr Gly Ser Gly Thr Asp Phe Thr Val Arg Ile
 65                  70                  75                  80 agc aga gtg gag gct gag gat ctg gga ctt tat tac tgc ttt caa ggt      288
Ser Arg Val Glu Ala Glu Asp Leu Gly Leu Tyr Tyr Cys Phe Gln Gly
                85                  90                  95 tca cgt gtt ccg tac acg ttc gga ggg ggg acc aag ctg gaa ata aaa      336
Ser Arg Val Pro Tyr Thr Phe Gly Gly Gly Thr Lys Leu Glu Ile Lys
                100                 105                 110
```

<210> SEQ ID NO 32
<211> LENGTH: 112
<212> TYPE: PRT
<213> ORGANISM: Murine sp.

<400> SEQUENCE: 32

Ala Val Leu Met Thr Gln Thr Pro Leu Ser Leu Pro Val Ser Leu Gly
 1               5                  10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Thr Gly Ser Gly Thr Asp Phe Thr Val Arg Ile
65                  70                  75                  80

Ser Arg Val Glu Ala Glu Asp Leu Gly Leu Tyr Tyr Cys Phe Gln Gly
                85                  90                  95

Ser Arg Val Pro Tyr Thr Phe Gly Gly Gly Thr Lys Leu Glu Ile Lys
            100                 105                 110

<210> SEQ ID NO 33
<211> LENGTH: 336
<212> TYPE: DNA
<213> ORGANISM: Artificial Sequence
<220> FEATURE:
<223> OTHER INFORMATION: Description of Artificial Sequence: cMu9VH DNA
      sequence
<220> FEATURE:
<221> NAME/KEY: CDS
<222> LOCATION: (1)..(336)

<400> SEQUENCE: 33 cag gtc caa ctg cag gag tca gga cct gag ctg gtg aag cct ggg gct      48
Gln Val Gln Leu Gln Glu Ser Gly Pro Glu Leu Val Lys Pro Gly Ala
 1               5                  10                  15 tca gtg aag atg tcc tgc agg gct tct gga tac acc ttc act gag tat      96
Ser Val Lys Met Ser Cys Arg Ala Ser Gly Tyr Thr Phe Thr Glu Tyr
            20                  25                  30 gtt att acc tgg gta aaa cag aga act gga cag ggc ctt gag tgg att     144
Val Ile Thr Trp Val Lys Gln Arg Thr Gly Gln Gly Leu Glu Trp Ile
        35                  40                  45 gga gag att tat cct gga agt ggt agt act tcc tac aat gaa aag ttc     192
Gly Glu Ile Tyr Pro Gly Ser Gly Ser Thr Ser Tyr Asn Glu Lys Phe
    50                  55                  60 aag ggc aag gcc aca ctg act gca gac aaa tcc tcc aac aca gcc tac     240
Lys Gly Lys Ala Thr Leu Thr Ala Asp Lys Ser Ser Asn Thr Ala Tyr
65                  70                  75                  80 atg cac ctc agc agc ctg aca tct gag gac tct gcg gtc tat ttc tgt     288
Met His Leu Ser Ser Leu Thr Ser Glu Asp Ser Ala Val Tyr Phe Cys
                85                  90                  95 aca aga gag gat ctt ggg ggc caa ggg act ctg gtc acc gtc tcc tca     336
Thr Arg Glu Asp Leu Gly Gly Gln Gly Thr Leu Val Thr Val Ser Ser
            100                 105                 110

<210> SEQ ID NO 34
<211> LENGTH: 112
<212> TYPE: PRT
<213> ORGANISM: Artificial Sequence
<220> FEATURE:

<223> OTHER INFORMATION: Description of Artificial Sequence: cMu9VH
       amino acid sequence

<400> SEQUENCE: 34

Gln Val Gln Leu Gln Glu Ser Gly Pro Glu Leu Val Lys Pro Gly Ala
  1               5                  10                  15

Ser Val Lys Met Ser Cys Arg Ala Ser Gly Tyr Thr Phe Thr Glu Tyr
             20                  25                  30

Val Ile Thr Trp Val Lys Gln Arg Thr Gly Gln Gly Leu Glu Trp Ile
         35                  40                  45

Gly Glu Ile Tyr Pro Gly Ser Gly Ser Thr Ser Tyr Asn Glu Lys Phe
     50                  55                  60

Lys Gly Lys Ala Thr Leu Thr Ala Asp Lys Ser Ser Asn Thr Ala Tyr
 65                  70                  75                  80

Met His Leu Ser Ser Leu Thr Ser Glu Asp Ser Ala Val Tyr Phe Cys
                 85                  90                  95

Thr Arg Glu Asp Leu Gly Gly Gly Gly Thr Leu Val Thr Val Ser Ser
            100                 105                 110

<210> SEQ ID NO 35
<211> LENGTH: 339
<212> TYPE: DNA
<213> ORGANISM: Artificial Sequence
<220> FEATURE:
<223> OTHER INFORMATION: Description of Artificial Sequence: cMu9Vk DNA
       sequence
<220> FEATURE:
<221> NAME/KEY: CDS
<222> LOCATION: (1)..(339)

<400> SEQUENCE: 35 gac atc ctg cag acc caa act cca ctc tcc ctg cct gtc agt ctt gga      48
Asp Ile Leu Gln Thr Gln Thr Pro Leu Ser Leu Pro Val Ser Leu Gly
  1               5                  10                  15 gat caa gcc tcc atc tct tgc aga tct agt cag agc att gtc cat agt      96
Asp Gln Ala Ser Ile Ser Cys Arg Ser Ser Gln Ser Ile Val His Ser
             20                  25                  30 aat ggc aac acc tat tta gaa tgg tac ctg cag aaa cca ggc cag tct     144
Asn Gly Asn Thr Tyr Leu Glu Trp Tyr Leu Gln Lys Pro Gly Gln Ser
         35                  40                  45 cca aag ctc ctg atc tac aaa gtt tcc aac cga ttt tct ggg gtc cca     192
Pro Lys Leu Leu Ile Tyr Lys Val Ser Asn Arg Phe Ser Gly Val Pro
     50                  55                  60 gac agg ttc agt ggc act gga tca ggg aca gat ttc aca gtc agg atc     240
Asp Arg Phe Ser Gly Thr Gly Ser Gly Thr Asp Phe Thr Val Arg Ile
 65                  70                  75                  80 agc aga gtg gag gct gag gat ctg gga ctt tat tac tgc ttt caa ggt     288
Ser Arg Val Glu Ala Glu Asp Leu Gly Leu Tyr Tyr Cys Phe Gln Gly
                 85                  90                  95 tca cgt gtt ccg tac acg ttc gga ggg ggg acc aag ctg gag atc aaa     336
Ser Arg Val Pro Tyr Thr Phe Gly Gly Gly Thr Lys Leu Glu Ile Lys
            100                 105                 110 cgt                                                                  339
Arg

<210> SEQ ID NO 36
<211> LENGTH: 113
<212> TYPE: PRT
<213> ORGANISM: Artificial Sequence
<220> FEATURE:
<223> OTHER INFORMATION: Description of Artificial Sequence: cMu9Vk
       amino acid sequence

```
<400> SEQUENCE: 36

Asp Ile Leu Gln Thr Gln Thr Pro Leu Ser Leu Pro Val Ser Leu Gly
  1               5                  10                  15

Asp Gln Ala Ser Ile Ser Cys Arg Ser Ser Gln Ser Ile Val His Ser
             20                  25                  30

Asn Gly Asn Thr Tyr Leu Glu Trp Tyr Leu Gln Lys Pro Gly Gln Ser
         35                  40                  45

Pro Lys Leu Leu Ile Tyr Lys Val Ser Asn Arg Phe Ser Gly Val Pro
     50                  55                  60

Asp Arg Phe Ser Gly Thr Gly Ser Gly Thr Asp Phe Thr Val Arg Ile
 65                  70                  75                  80

Ser Arg Val Glu Ala Glu Asp Leu Gly Leu Tyr Tyr Cys Phe Gln Gly
                 85                  90                  95

Ser Arg Val Pro Tyr Thr Phe Gly Gly Gly Thr Lys Leu Glu Ile Lys
            100                 105                 110

Arg

<210> SEQ ID NO 37
<211> LENGTH: 336
<212> TYPE: DNA
<213> ORGANISM: Artificial Sequence
<220> FEATURE:
<223> OTHER INFORMATION: Description of Artificial Sequence: hMu9VH DNA
      sequence
<220> FEATURE:
<221> NAME/KEY: CDS
<222> LOCATION: (1)..(336)

<400> SEQUENCE: 37 cag gtc caa ctg cag cag tca gga gct gag gtg aaa aag cct ggg agc    48
Gln Val Gln Leu Gln Gln Ser Gly Ala Glu Val Lys Lys Pro Gly Ser
  1               5                  10                  15 tca gtg aag gtc tcc tgc aag gct tct gga tac acc ttc act gag tat    96
Ser Val Lys Val Ser Cys Lys Ala Ser Gly Tyr Thr Phe Thr Glu Tyr
             20                  25                  30 gtt att acc tgg gta aaa cag aga cct gga cag ggt cta gag tgg att   144
Val Ile Thr Trp Val Lys Gln Arg Pro Gly Gln Gly Leu Glu Trp Ile
         35                  40                  45 gga gag att tat cct gga agt ggt agt act tcc tac aat gaa aag ttc   192
Gly Glu Ile Tyr Pro Gly Ser Gly Ser Thr Ser Tyr Asn Glu Lys Phe
     50                  55                  60 aag ggc aag gcc aca atc act gct gac aaa tcc act aac aca gcc tac   240
Lys Gly Lys Ala Thr Ile Thr Ala Asp Lys Ser Thr Asn Thr Ala Tyr
 65                  70                  75                  80 atg gag ctc agc agc ctg aga tct gag gac act gcg ttc tat ttc tgt   288
Met Glu Leu Ser Ser Leu Arg Ser Glu Asp Thr Ala Phe Tyr Phe Cys
                 85                  90                  95 aca aga gag gat ctt ggg ggc caa ggg tct ctg gtc acc gtc tcc tca   336
Thr Arg Glu Asp Leu Gly Gly Gln Gly Ser Leu Val Thr Val Ser Ser
            100                 105                 110

<210> SEQ ID NO 38
<211> LENGTH: 112
<212> TYPE: PRT
<213> ORGANISM: Artificial Sequence
<220> FEATURE:
<223> OTHER INFORMATION: Description of Artificial Sequence: hMu9VH
      amino acid sequence

<400> SEQUENCE: 38
```

```
Gln Val Gln Leu Gln Gln Ser Gly Ala Glu Val Lys Lys Pro Gly Ser
 1               5                  10                  15

Ser Val Lys Val Ser Cys Lys Ala Ser Gly Tyr Thr Phe Thr Glu Tyr
             20                  25                  30

Val Ile Thr Trp Val Lys Gln Arg Pro Gly Gln Gly Leu Glu Trp Ile
         35                  40                  45

Gly Glu Ile Tyr Pro Gly Ser Gly Ser Thr Tyr Asn Glu Lys Phe
     50                  55                  60

Lys Gly Lys Ala Thr Ile Thr Ala Asp Lys Ser Thr Asn Thr Ala Tyr
 65                  70                  75                  80

Met Glu Leu Ser Ser Leu Arg Ser Glu Asp Thr Ala Phe Tyr Phe Cys
                 85                  90                  95

Thr Arg Glu Asp Leu Gly Gly Gln Gly Ser Leu Val Thr Val Ser Ser
100                 105                 110
```

<210> SEQ ID NO 39
<211> LENGTH: 339
<212> TYPE: DNA
<213> ORGANISM: Artificial Sequence
<220> FEATURE:
<223> OTHER INFORMATION: Description of Artificial Sequence: hMu9Vk DNA
      sequence
<220> FEATURE:
<221> NAME/KEY: CDS
<222> LOCATION: (1)..(339)

<400> SEQUENCE: 39

```
gac atc cag ctg acc caa tcc cca ggc acc ctg tcc ctc agt cct gga      48
Asp Ile Gln Leu Thr Gln Ser Pro Gly Thr Leu Ser Leu Ser Pro Gly
 1               5                  10                  15 gag cga gcc act ctg tct tgc agg tct agt cag agc att gtg cat agt      96
Glu Arg Ala Thr Leu Ser Cys Arg Ser Ser Gln Ser Ile Val His Ser
             20                  25                  30 aat ggc aac acc tat tta gaa tgg tac ctg cag aaa cca ggc cag gct     144
Asn Gly Asn Thr Tyr Leu Glu Trp Tyr Leu Gln Lys Pro Gly Gln Ala
         35                  40                  45 cca agg ctc ctg atc tac aaa gtt tcc aac cga ttt tcc gga gtc cca     192
Pro Arg Leu Leu Ile Tyr Lys Val Ser Asn Arg Phe Ser Gly Val Pro
     50                  55                  60 gac agg ttc agt ggc tct gga tca ggg aca gat ttc aca ctt act atc     240
Asp Arg Phe Ser Gly Ser Gly Ser Gly Thr Asp Phe Thr Leu Thr Ile
 65                  70                  75                  80 agc aga ctg gag cct gag gat ttt gct gtg tat tac tgc ttt caa ggt     288
Ser Arg Leu Glu Pro Glu Asp Phe Ala Val Tyr Tyr Cys Phe Gln Gly
                 85                  90                  95 tca cgt gtt ccg tac acg ttc gga ggg ggg acc aag gtg gag atc aaa     336
Ser Arg Val Pro Tyr Thr Phe Gly Gly Gly Thr Lys Val Glu Ile Lys
            100                 105                 110 cgt                                                                  339
Arg
```

<210> SEQ ID NO 40
<211> LENGTH: 113
<212> TYPE: PRT
<213> ORGANISM: Artificial Sequence
<220> FEATURE:
<223> OTHER INFORMATION: Description of Artificial Sequence: hMu9Vk
      amino acid sequence

<400> SEQUENCE: 40

```
Asp Ile Gln Leu Thr Gln Ser Pro Gly Thr Leu Ser Leu Ser Pro Gly
 1               5                  10                  15
```

```
Glu Arg Ala Thr Leu Ser Cys Arg Ser Ser Gln Ser Ile Val His Ser
             20                  25                  30

Asn Gly Asn Thr Tyr Leu Glu Trp Tyr Leu Gln Lys Pro Gly Gln Ala
             35                  40                  45

Pro Arg Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Thr Ile
 65                  70                  75                  80

Ser Arg Leu Glu Pro Glu Asp Phe Ala Val Tyr Tyr Cys Phe Gln Gly
                 85                  90                  95

Ser Arg Val Pro Tyr Thr Phe Gly Gly Gly Thr Lys Val Glu Ile Lys
             100                 105                 110

Arg

<210> SEQ ID NO 41
<211> LENGTH: 127
<212> TYPE: PRT
<213> ORGANISM: Homo sapiens

<400> SEQUENCE: 41

Pro Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Arg Ser
             20                  25                  30

Ala Ile Ile Trp Val Arg Gln Ala Pro Gly Gln Gly Leu Glu Trp Met
         35                      40                  45

Gly Gly Ile Val Pro Met Phe Gly Pro Pro Asn Tyr Ala Gln Lys Phe
     50                  55                      60

Gln Gly Arg Val Thr Ile Thr Ala Asp Glu Ser Thr Asn Thr Ala Tyr
 65                  70                  75                  80

Met Glu Leu Ser Ser Leu Arg Ser Glu Asp Thr Ala Phe Tyr Phe Cys
                 85                  90                  95

Ala Gly Gly Tyr Gly Ile Tyr Ser Pro Glu Glu Tyr Asn Gly Gly Leu
             100                 105                 110

Val Thr Val Ser Trp Gly Gln Gly Ser Leu Val Thr Val Ser Ser
             115                 120                 125
```